United States Patent [19]

Sano

[11] Patent Number: 5,701,897
[45] Date of Patent: Dec. 30, 1997

[54] ULTRASONIC DIAGNOSIS APPARATUS AND IMAGE DISPLAYING SYSTEM

[75] Inventor: Akihiro Sano, Otawara, Japan

[73] Assignee: Kabushiki Kaisha Toshiba, Kanagawa-ken, Japan

[21] Appl. No.: 583,501

[22] Filed: Jan. 5, 1996

Related U.S. Application Data

[62] Division of Ser. No. 130,834, Oct. 4, 1993, Pat. No. 5,622, 174.

[30] Foreign Application Priority Data

| Oct. 2, 1992 | [JP] | Japan | 4-265052 |
| Mar. 31, 1993 | [JP] | Japan | 5-074448 |
| Apr. 1, 1993 | [JP] | Japan | 5-075965 |
| Apr. 7, 1993 | [JP] | Japan | 5-080931 |

[51] Int. Cl.$^6$ .................................................. A61B 8/06
[52] U.S. Cl. ........................... 128/661.09; 128/660.05
[58] Field of Search ........................ 128/660.01, 660.07, 128/660.05, 661.02, 661.07–661.1

[56] References Cited

U.S. PATENT DOCUMENTS

| 4,790,322 | 12/1988 | Iinuma . |
| 5,097,836 | 3/1992 | Yamada et al. . |
| 5,107,840 | 4/1992 | Bonnefous .................. 128/661.08 |
| 5,148,809 | 9/1992 | Biegeleisen-Knight et al. . |
| 5,152,290 | 10/1992 | Freeland . |
| 5,190,044 | 3/1993 | Kawasaki et al. . |
| 5,211,169 | 5/1993 | Freeland . |
| 5,224,481 | 7/1993 | Ishihara et al. . |
| 5,285,788 | 2/1994 | Arenson et al. . |
| 5,325,859 | 7/1994 | Ishihara et al. . |
| 5,355,887 | 10/1994 | Iizuka et al. . |
| 5,360,006 | 11/1994 | Geiser et al. .................. 128/653.1 |
| 5,435,310 | 7/1995 | Sheehan et al. .................. 128/653.1 |
| 5,469,850 | 11/1995 | Iizuka et al. .................. 128/660.07 |
| 5,513,640 | 5/1996 | Yamazahi et al. .............. 128/660.05 X |

FOREIGN PATENT DOCUMENTS 2-193650   7/1990   Japan .

OTHER PUBLICATIONS

W.N. McDicken et al., "Colour Doppler Velocity Imaging of the Mycoardium", Ultrasound in Med. & Biol., vol. 18, Nos. 6/7, pp. 651–654, 1992.

Primary Examiner—Francis Jaworski
Attorney, Agent, or Firm—Finnegan, Henderson, Farabow, Garrett & Dunner, L.L.P.

[57] ABSTRACT

There is provided an ultrasonic diagnosis apparatus in which a region containing an organ of an object being examined is diagnosed by means of ultrasonic beams, the organ being in motion, the apparatus comprising: an element for scanning the region by the ultrasonic beams to obtain ultrasonic echo signals having Doppler shift; an element for calculating movement velocities every sampling volume on the basis of the ultrasonic echo signals; and an element for displaying in color the movement velocities.

24 Claims, 84 Drawing Sheets

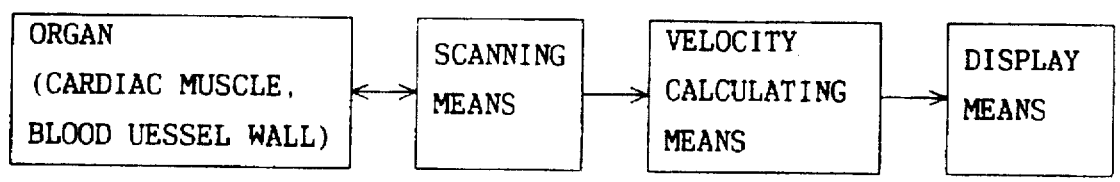
F I G. 3

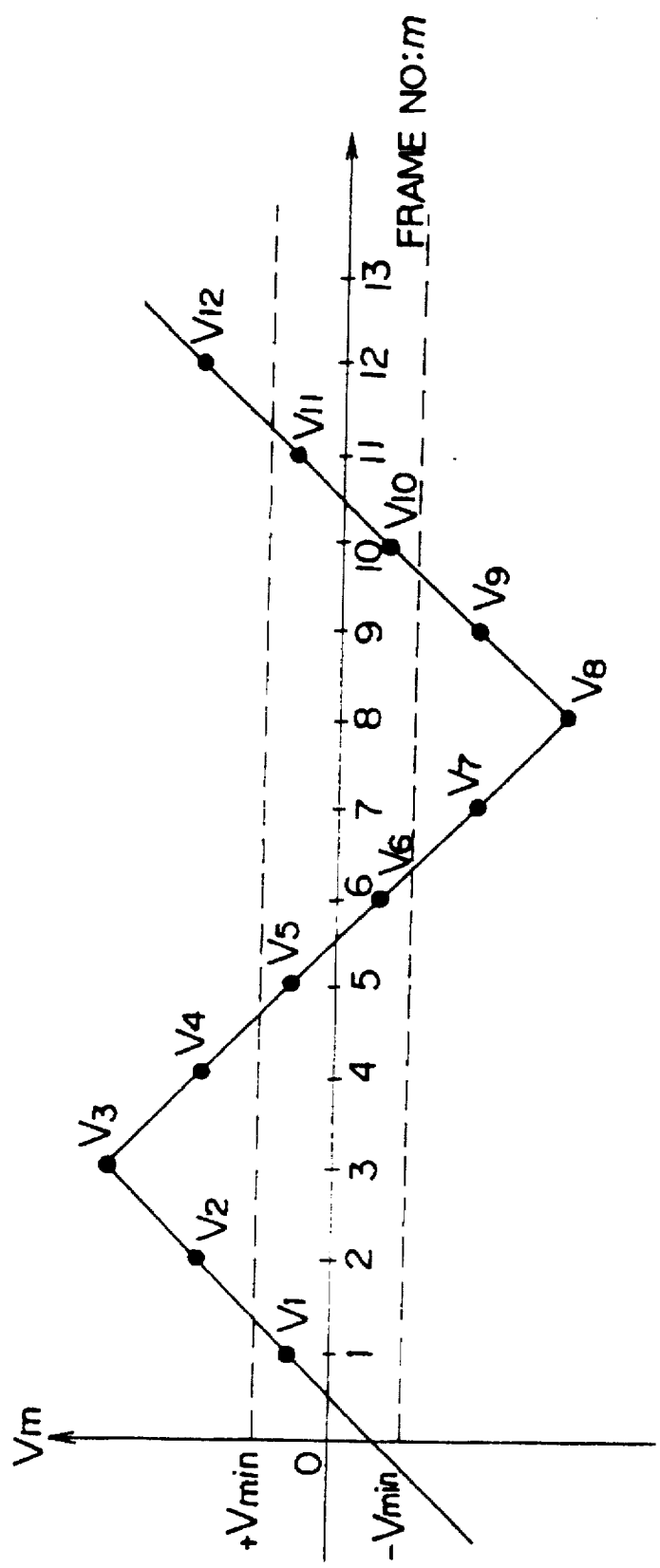
F I G. 41

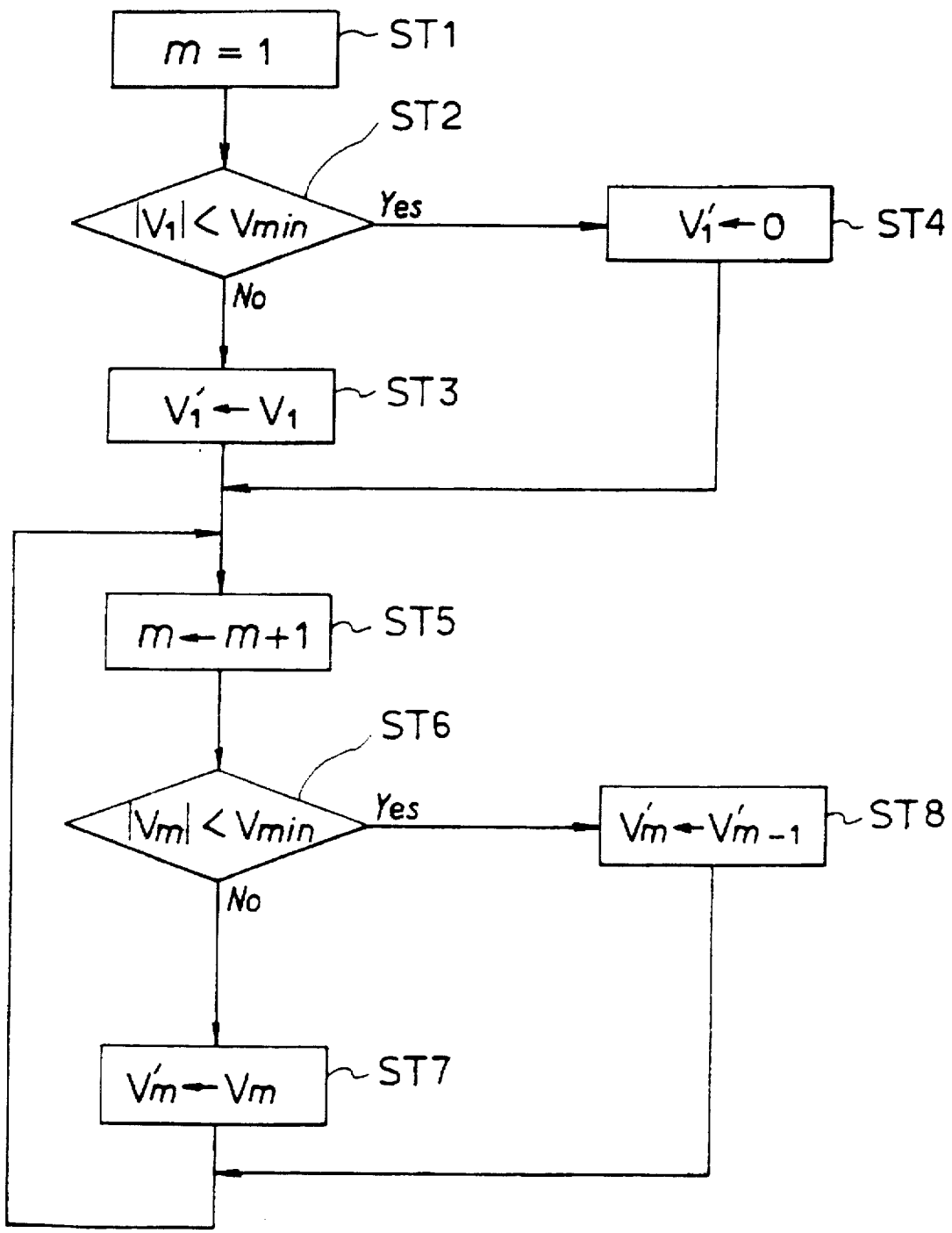
F I G. 42

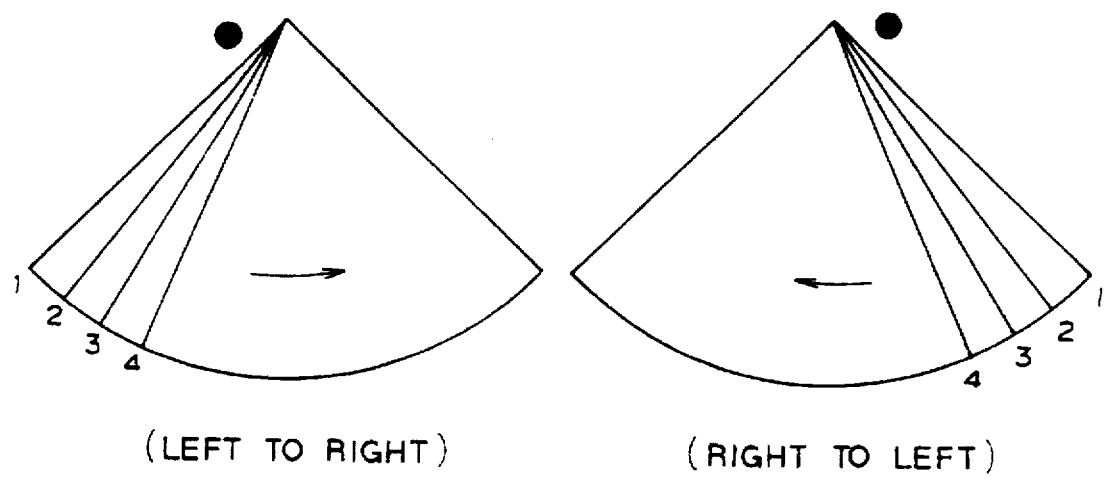
(LEFT TO RIGHT)    (RIGHT TO LEFT)
F I G. 50A    F I G. 50B

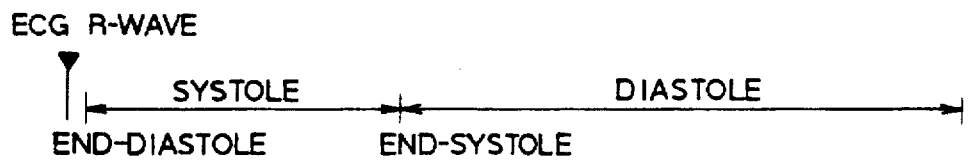
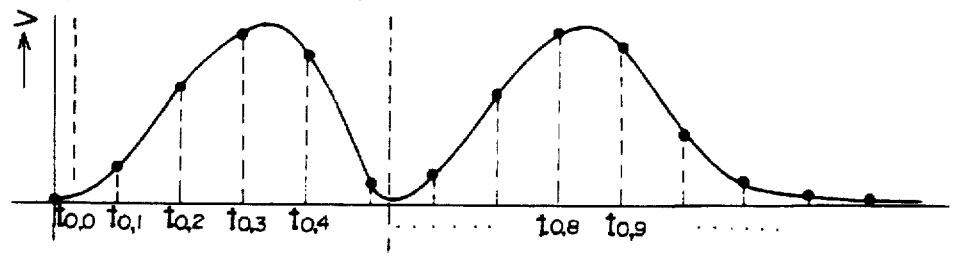
FIG. 51A  1st HEAT BEAT: $\Delta t = 0$
FIG. 51B  2nd HEAT BEAT: $\Delta t = \frac{1}{4}T$
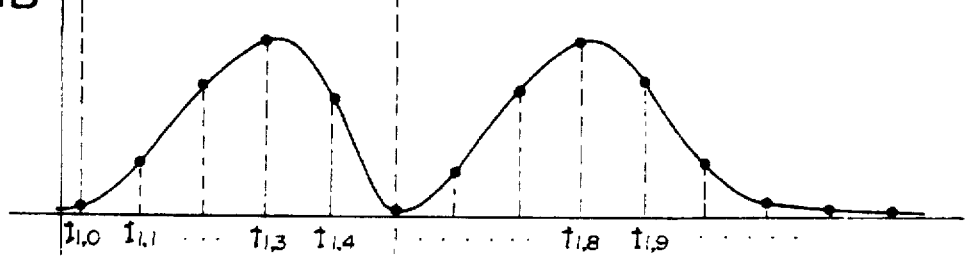
FIG. 51C  3rd HEAT BEAT: $\Delta t = \frac{2}{4}T$
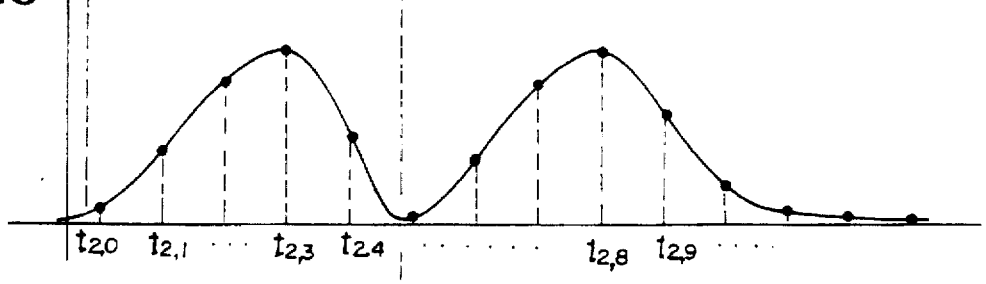
FIG. 51D  4th HEAT BEAT: $\Delta t = \frac{3}{4}T$
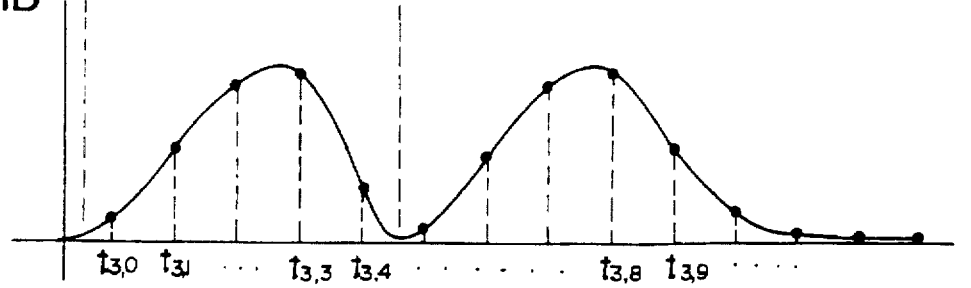

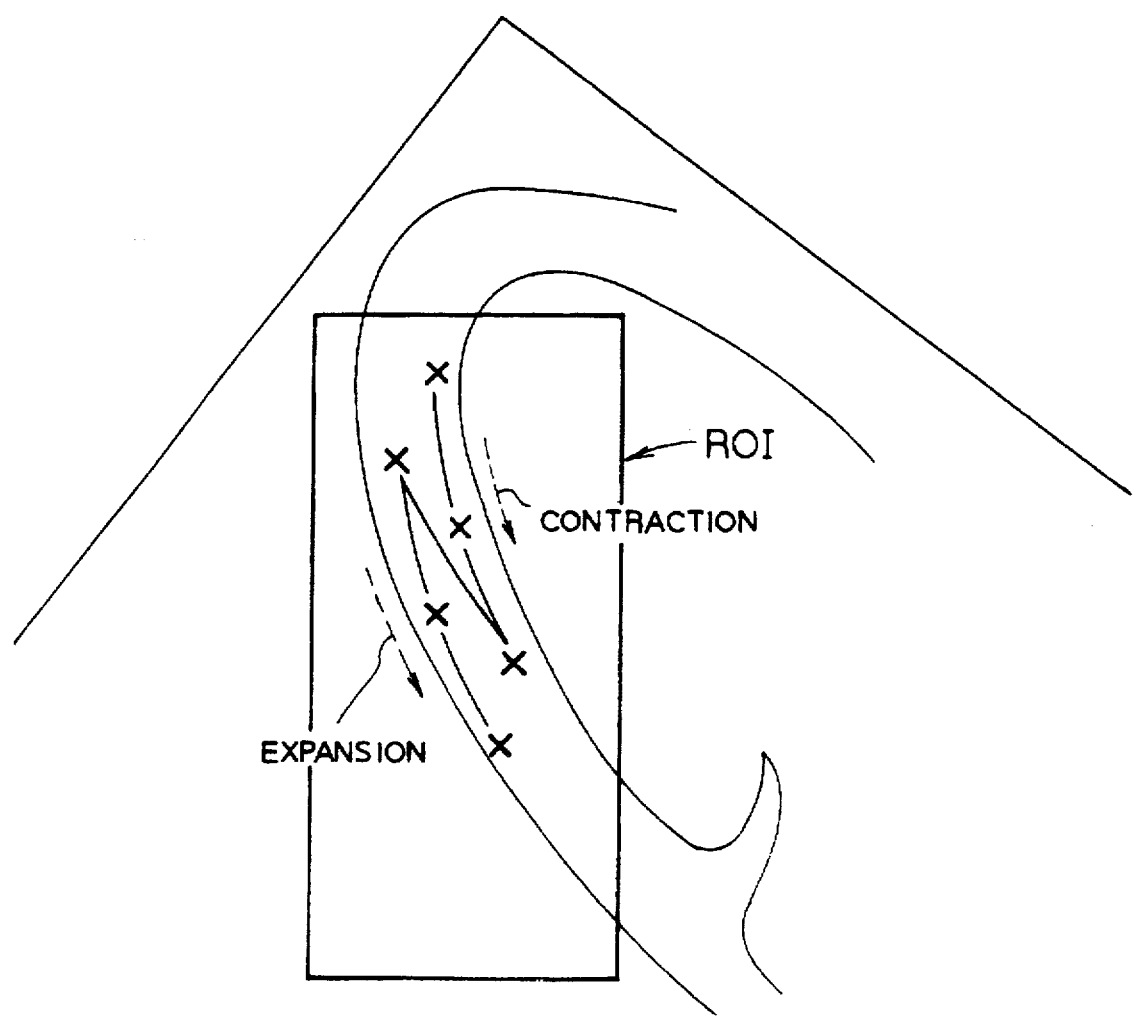
F I G. 56

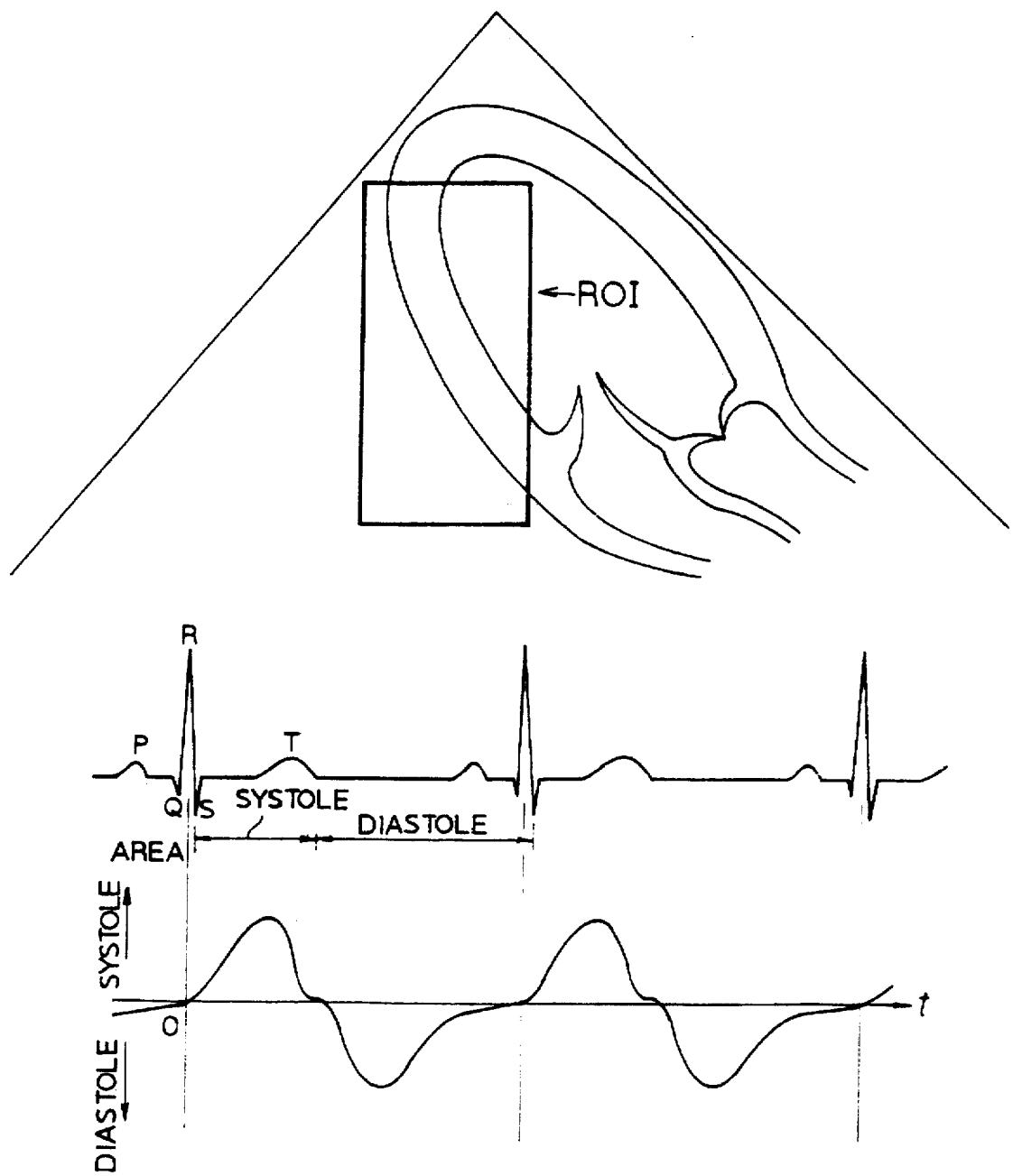
F I G. 57

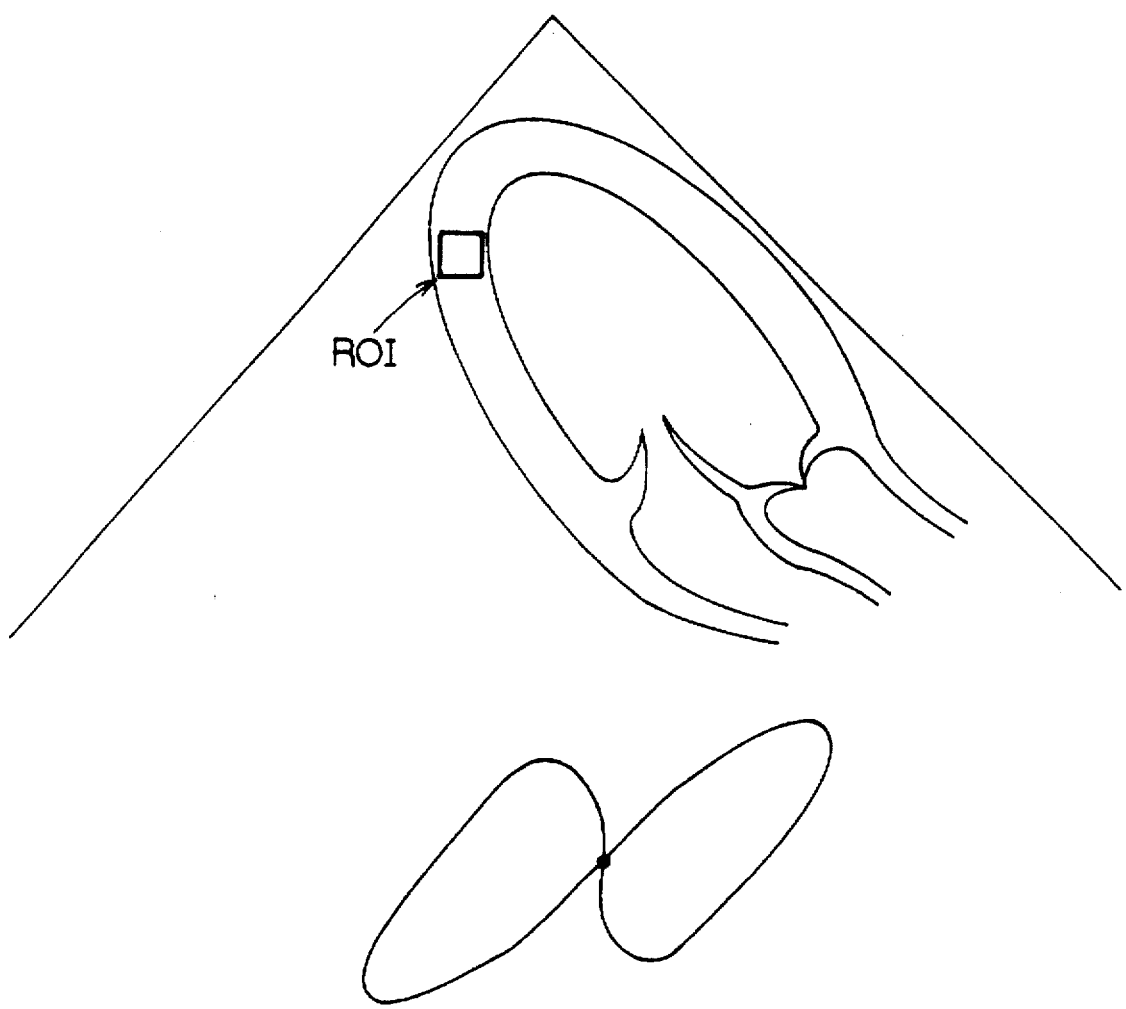
F I G. 58

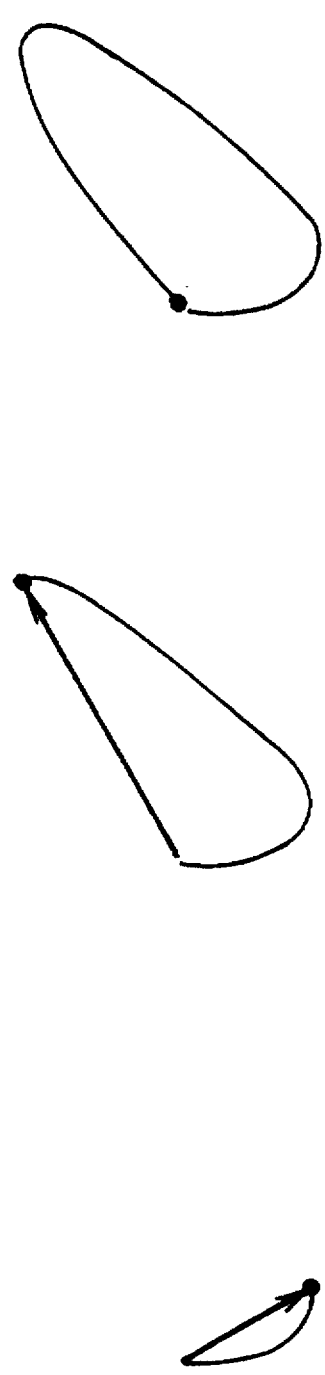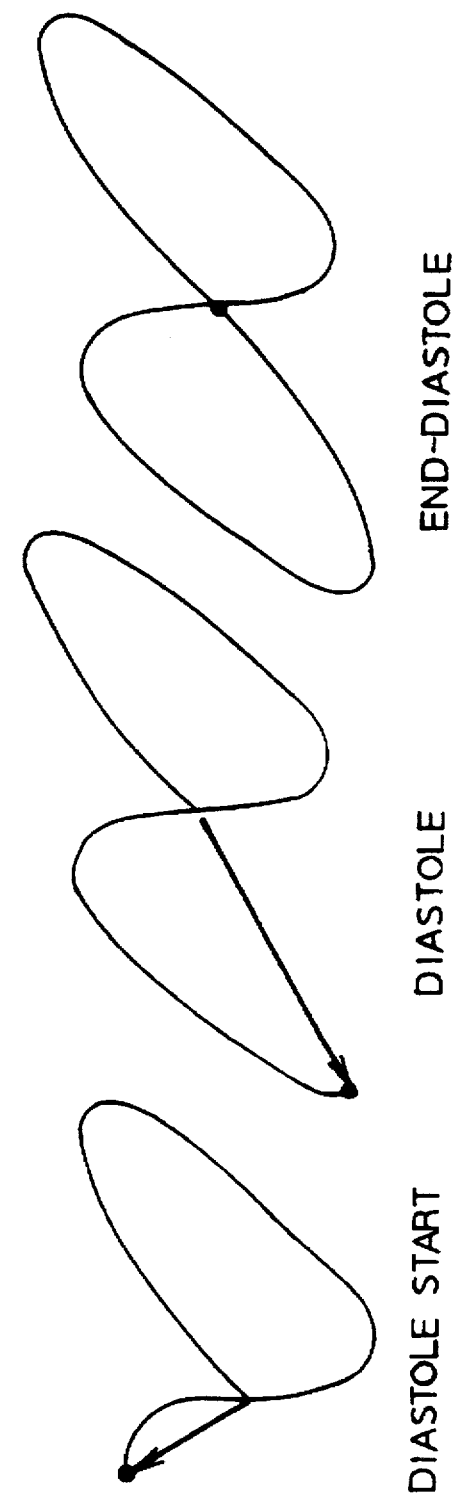

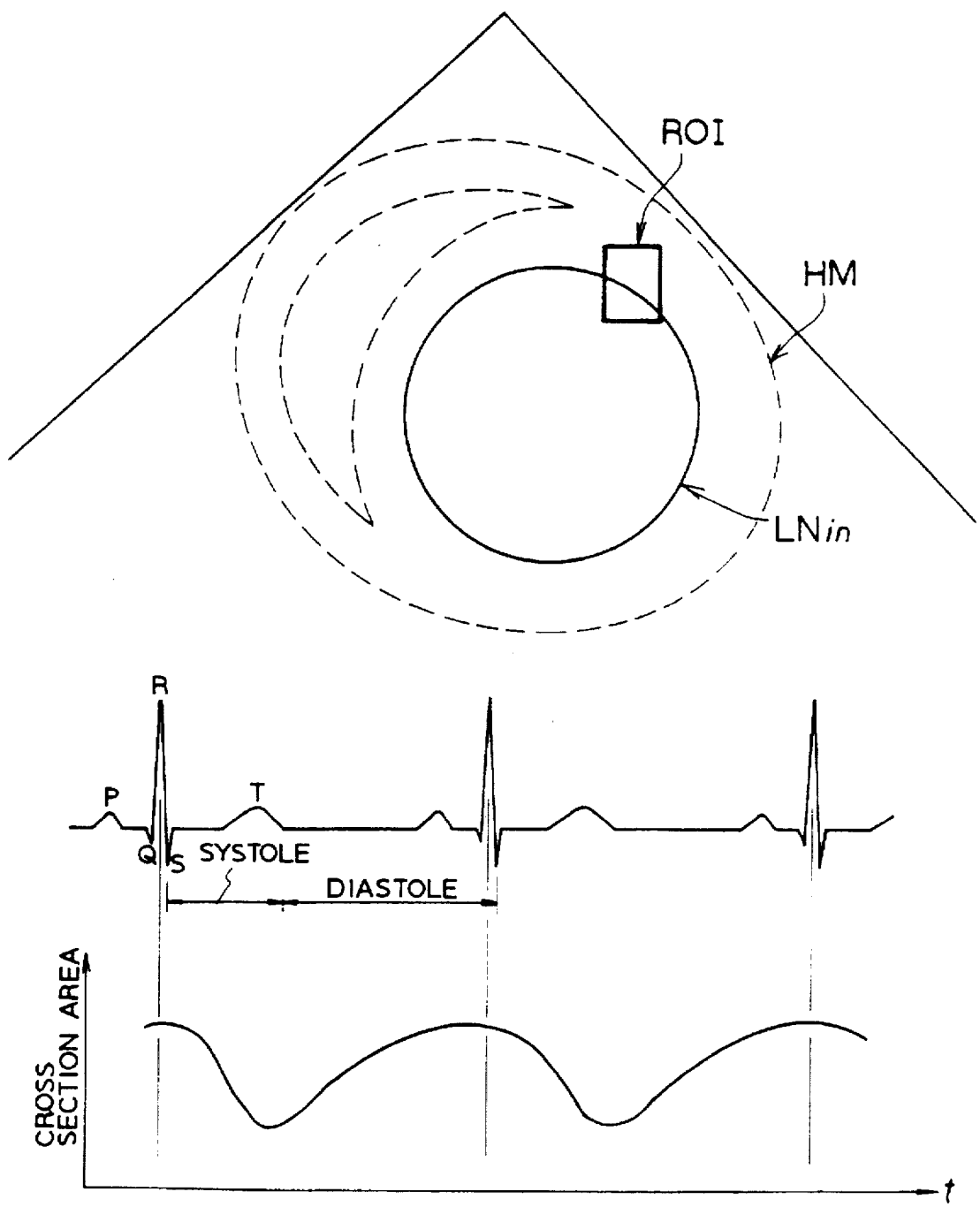
F I G. 62

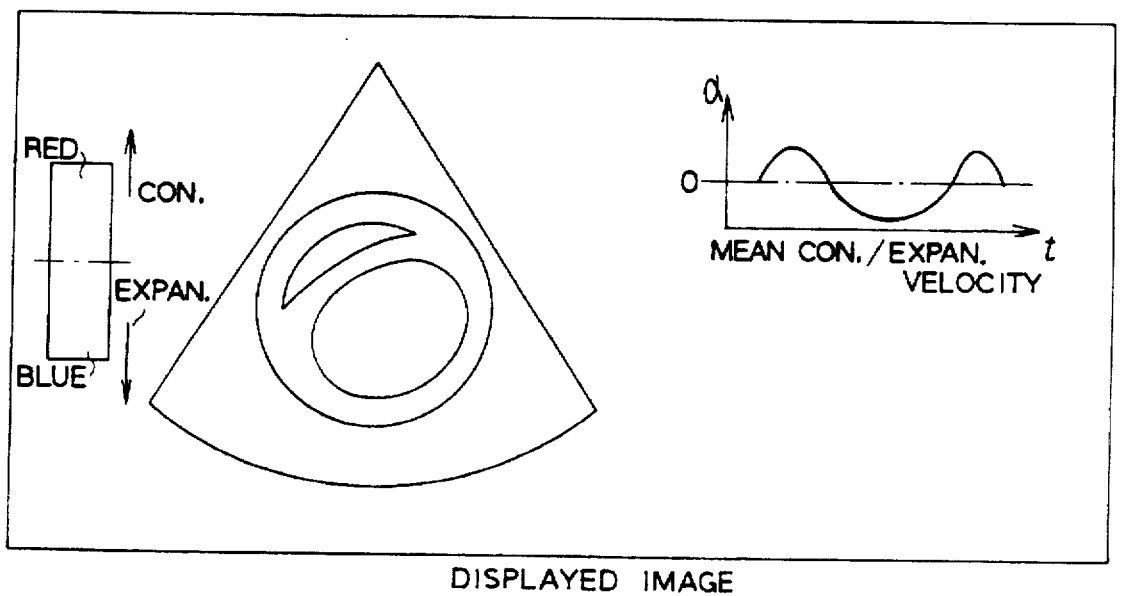
F I G. 73

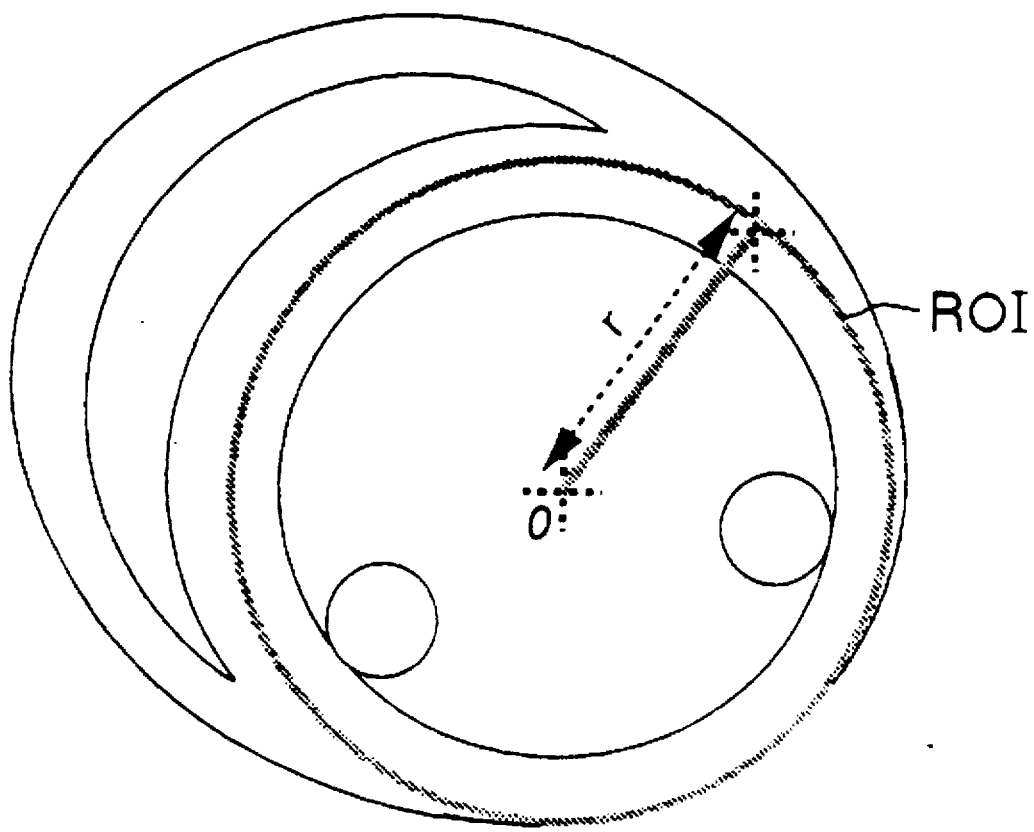
F I G. 79

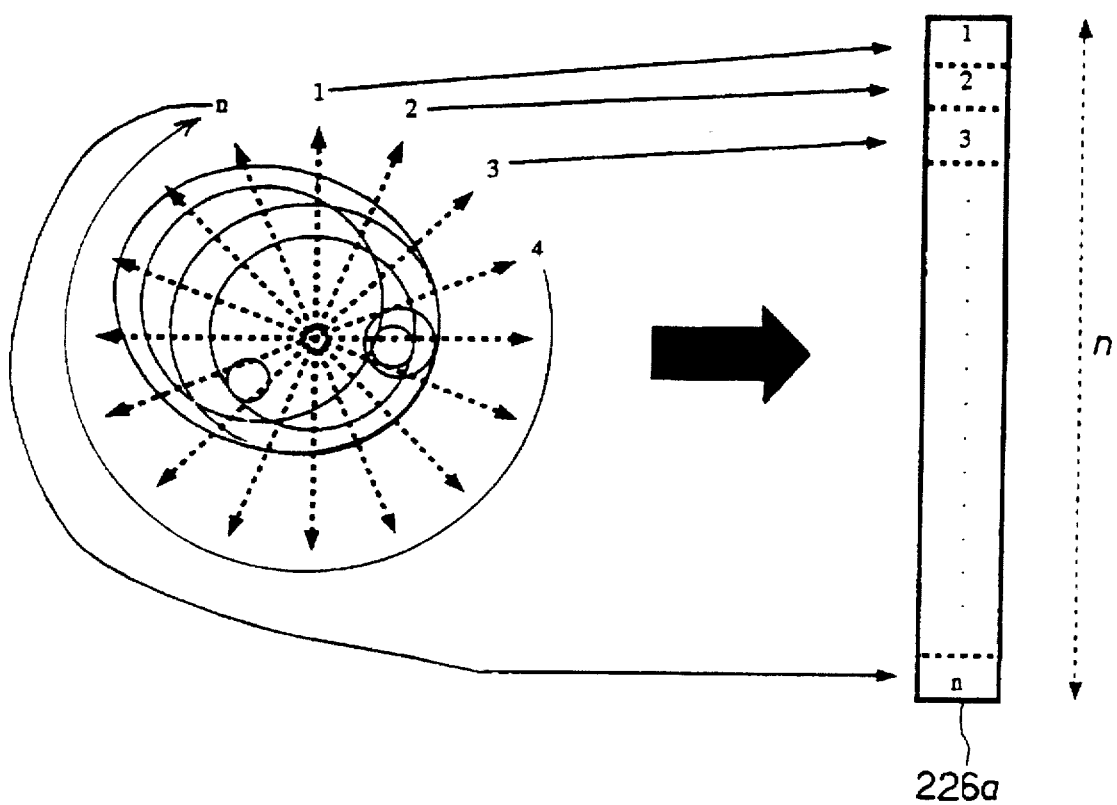
F I G. 81

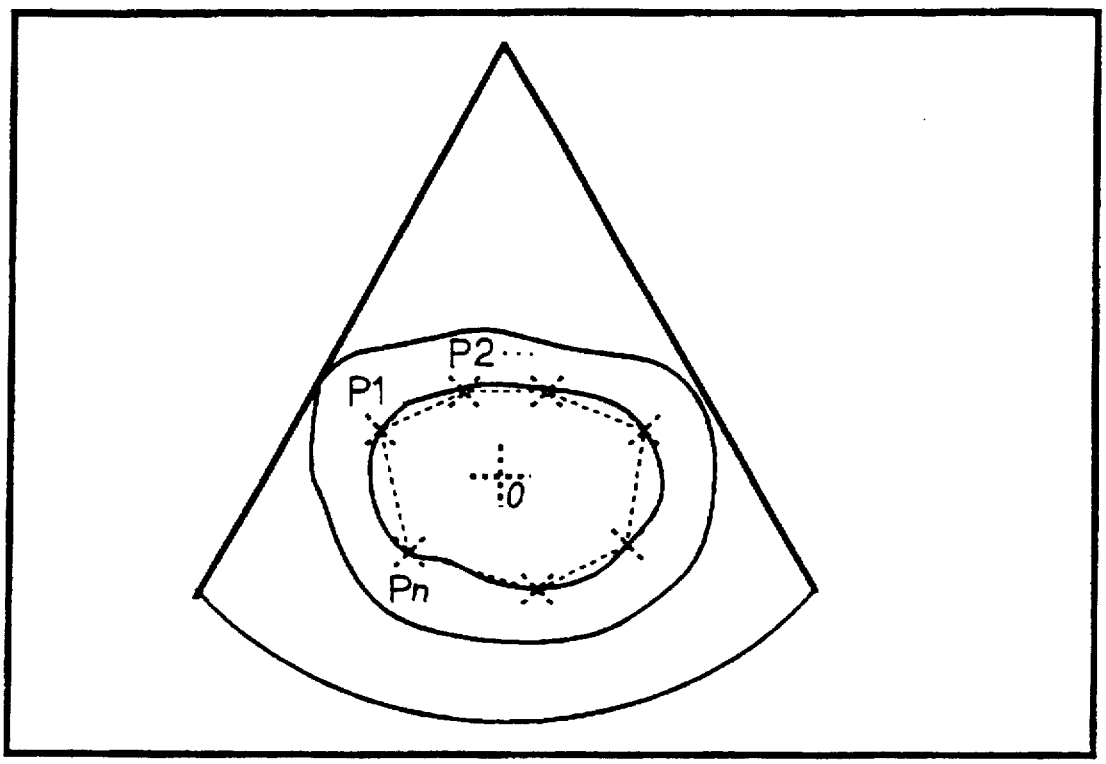
F I G. 84

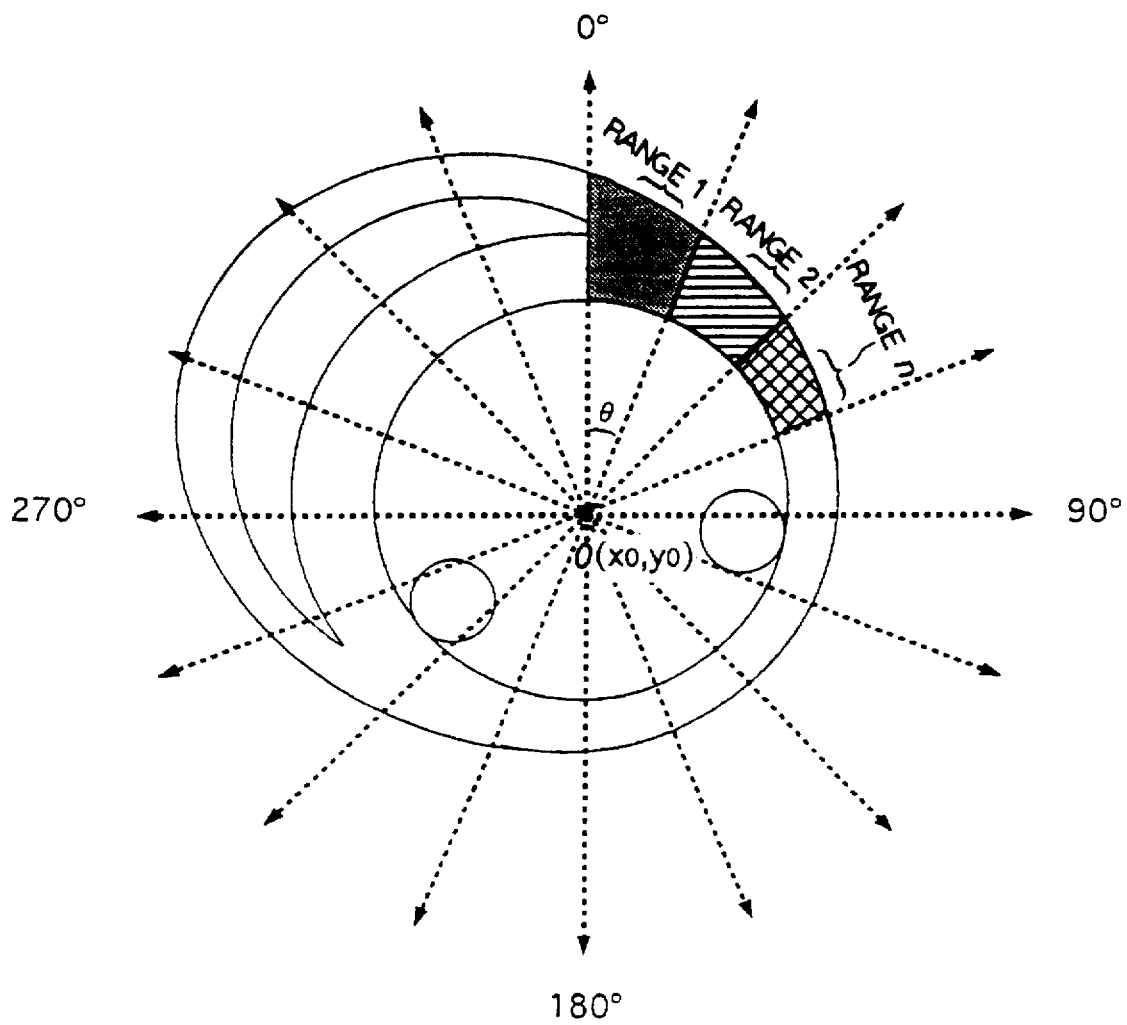
F I G. 87

ULTRASONIC DIAGNOSIS APPARATUS AND IMAGE DISPLAYING SYSTEM

This is a division of application Ser. No. 08/130,834, filed Oct. 4, 1993 and now U.S. Pat. No. 5,622,174.

BACKGROUND OF THE INVENTION

The present invention relates to an ultrasonic diagnosis apparatus in which velocities of movement of an organ in motion of an object, such as a cardiac muscle of a heart and a blood vessel wall, are obtained and displayed and if necessary, on the basis of the velocities, other physical values representing conditions of the movement are calculated and displayed, and an image displaying system which can preferably used for the apparatus. Particularly, the ultrasonic diagnosis apparatus relates to an apparatus effective in diagnosis of ischemic cardiodiseases such as myocardial ischemia and angina pectoris, left ventricle distention disorders including hypertrophic cardiomyopathy, disorders of the conducting system of the heart like an Wolff-Parkinson-White syndrome.

Today, diagnosis of heart diseases tends to require quantitative estimation of functions of a cardiac muscle and blood vessel. Thus there are a wide variety of diagnostic methods for the quantitative estimation.

In a field of diagnosis by ultrasnonic beams, a real-time B-mode tomographic image is observed very often for the left ventricle of a heart, which is the key to evaluation of functions of the heart. In case that the above-mentioned ischemic cardiodiseases, left ventricle distention disorders, and disorders of a conducting system of the heart are considerably serious, the observation of the B-mode tomographic image is useful. But trouble is that it is practically impossible to acquire detailed information with respect to detection of local deteriorated portions in contraction ability in ischemic cardiodisease, objective diagnosis of left ventricle distention disorders, and detection of positions and extent of abnormal paries movement in a conducting system of the heart.

To overcome the drawback for ischemic cardiodisease, there is an exclusive analysis method of paries movement of a left ventricle. The analysis method is to measure changes in thickness of the cardiac muscle of the left ventricle in both its systole and diastole and to diagnose such that a portion of less changes in thickness is a deteriorated portion in contraction ability, or ischemia portion. Although there are various algorithms for the analysis method, they require tracing on a B-mode tomographic image an endocardium or epicardium of the left ventricle in both an end-systole and end-diastole.

A stress echography is also known for diagnosing myocardial ischemia. Carrying out the stress echography requires a heart to be stressed by exercise, drugs or an electric stimulus. And B-mode tomographic images of the heart will be recorded before and after stressing, respectively, to display those images on the same monitor. Then changes in thickess of the cardiac muscle are compared in its systole and diastole (normally, thicker in its systole), detecting a portion of myocardial infarction. It is also required for this detection to trace the inner and outer walls and the center line of a cardiac muscle on the images to get the contour of it.

The conventional tracing has been done by manual operation through a keyboard or track ball. This manual operation requires a deal of labor and takes a lot of time, thus being impossible to process in real time and being poor reproducibility.

Thus, there has been provided an automatic tracing method by which contour data of a cardiac muscle are automatically extracted from data of a B-mode tomographic image. The automatic trace uses differences in echo level between a cardiac muscle and its surrounding portion; a cardiac muscle is higher in echo level than its surrounding portion. A threshold level is set for an echo signal to detect the contour existing on the corresponding position to the threshold level.

However, in the above automatic trace, when an amplification factor (gain) for the echo signal is changed, the position extracted as a contour line is also moved. This results in that it is impossible for the B-mode image to automatically depict the contour of a cardiac muscle in real time and with high accuracy.

On top of the above difficulty, for the foregoing objective diagnosis of left ventricle distention disorders and detection of position and extent of abnormal paries movement in a conducting system of the heart, diagnosis methods have not yet been established that are simple and useful with an ultrasonic diagnosis apparatus.

Further, when conditions of a cardiac muscle and a blood vessel wall are observed, a conventionally used B-mode image is based on a real time display. Therefore, the image changes moment by moment and it is almost difficult to provide properly enough information over measurement time.

SUMMARY OF THE INVENTION

Accordingly, it is a primary object of the present invention to provide an ultrasonic diagnosis apparatus that is able to obtain movement information of an organ in motion, such as a cardiac muscle and a blood vessel wall, in real time to display the information in color, so that functional deterioration of the organ can be evaluated quantitatively and accurately.

It is a further object of the present invention to provide an ultrasonic diagnosis apparatus that uses an ultrasonic Doppler effect to detect a movement velocity in an ultrasonic beam direction, or an absolute velocity, as the movement information, and on the basis of the movement velocity, easily estimates or calculates a velocity at an observing point of the organ in an actual moving direction, with the result that the quantitative analysis and color display are more improved in accuracy.

It is a still further object of the present invention to calculate acceleration values and other related-values to the movement on the basis of the movement velocities and display them so that the movement can be analyzed from a wide variety of aspects, with a minimum detection construction for movement information retained.

It is a still further object of the present invention to enhance measurement capability of movement information.

It is a still further object of the present invention to automatically trace the contour of the organ with remarkably increased tracing accuracy and reproducibility and with remarkably improved operation (i.e. maneuverability).

It is a still further object of the present invention to easily obtain high-accuracy images by a stress echography.

It is a still further object of the present invention to obtain true two-dimensional movement velocity data of a moving organ by removing useless movement components.

It is a still further object of the present invention to provide an image displaying system that can display images having movement information of a moving organ over measurement time, so one can get movement information over time at a glance. It is a still further object of the present invention to use such an image displaying system in an ultrasonic diagnosis apparatus.

These and other objects can be achieved according to the present invention, in one aspect by providing, an ultrasonic diagnosis apparatus in which a region containing an organ of an object being examined is diagnosed by means of ultrasonic beams, the organ being in motion, the apparatus comprising: means for scanning the region by the ultrasonic beams to obtain ultrasonic echo signals having Doppler shift; means for calculating movement velocities every sampling volume on the basis of the ultrasonic echo signals; and means for displaying by color the movement velocities.

In another aspect, there is provided an ultrasonic diagnosis apparatus in which a region containing an organ of an object being examined is diagnosed by means of ultrasonic beams, the organ being in motion, the apparatus comprising: first means for scanning the region by ultrasonic beams to obtain ultrasonic echo signals having Doppler shift before stressing the organ; first means for calculating movement velocities every sampling volume on the basis of the ultrasonic echo signals obtained by the first scanning means; second means for scanning the region by ultrasonic beams to obtain ultrasonic echo signals having Doppler shift after stressing the organ; second means for calculating movement velocities every sampling volume on the basis of the ultrasonic echo signals obtained by the second scanning means; means for calculating a parameter representing a changed-value of a movement characteristic of the organ on the basis of the movement velocities calculated by the first and second movement velocity calculating means; and means for displaying by color the parameter.

In another aspect, there is provided an ultrasonic diagnosis apparatus in which a region containing an organ of an object being examined is diagnosed by means of ultrasonic beams, the organ being in motion, the apparatus comprising: means for scanning the region by the ultrasonic beams to obtain ultrasonic echo signals; means for obtaining velocities of movement of the organ every sampling volume in an ultrasonic frame on the basis of the ultrasonic echo signals; means for calculating an entirely uniform velocity component of movement of a tissue containing the organ on the basis of the velocities obtained by the velocity obtaining means; means for removing the entirely uniform velocity component from the velocities; and means for displaying an image on the basis of velocity data removed by the removing means.

In another aspect, there is provided an image displaying system comprising: means for obtaining two-dimensional movement velocity data of an object frame by frame; means for converting the two-dimensional movement velocity data of each frame into one-dimensional image with parameters denoting positions extending radially from a given point; and means for successively displaying the one-dimensional image data on a monitor, a time axis on the monitor being coincided with a number of frames.

In another aspect, there is provided an ultrasonic diagnosis apparatus having a scanning means for receiving an ultrasonic echo signal by scanning frame by frame repeatedly a diagnostic portion including such a moving organ as a cardiac muscle and a blood vessel wall and an image displaying means for displaying on a monitor a superimposed image of a tomographic image and a color image of the diagnostic portion on the basis of the ultrasonic echo signal, the improvement comprising: means for calculating a movement velocity of the organ for every sampling volume of each frame on the basis of the ultrasonic echo signal; means for setting an arbitrary base coordinate point on the tomographic image; means for setting a calculation region in accordance with scanning lines extending radially from the base coordinate point on the tomographic image of each frame; means for calculating a characteristic component of movement of the organ for every calculation region on the basis of the movement velocity of each frame calculated by the velocity calculating means; means for converting the characteristic component of each frame calculated by the characteristic-component calculating means to one-dimensional image with parameters denoting positions extending radially in the calculation region; and means for successively displaying the one-dimensional image data on the monitor, a time axis on the monitor being coincided with a number of frames.

BRIEF DESCRIPTION OF THE DRAWINGS

The accompanying drawings which are incorporated in and constitute a part of this specification, illustrate embodiments of the present invention and, together with the description, serve to explain the principles of the present invention. In the drawings:

FIG. 3 is a block diagram of an apparatus according to the present invention;

FIG. 41 is a curve showing change in velocity;

FIG. 42 is a flowchart showing improvement for detection of the velocity in automatic trace;

FIGS. 50A and 50B each explain a difference in scanning order in an azimuth direction;

FIGS. 51A to 51D show a correction in scanning beam direction;

FIG. 56 shows another measurement result of a value related to a movement velocity;

FIGS. 57 and 58 show still another measurement result of a value related to a movement velocity;

FIGS. 59A to 59F show a display process of a vector locus of FIG. 58;

FIGS. 60 to 62 show another measurement results of a value related to a movement velocity;

FIG. 73 is a pictorial display image in which the translation and/or rotation are removed;

FIG. 79 explains placing of a ROI in the sixteenth embodiment;

FIG. 81 shows coordinate conversion in the sixteenth embodiment;

FIG. 84 explains placing of a basic coordinate point in the seventeenth embodiment;

FIGS. 87 and 88 show calculation of a characteristic component of movement for radial blocks in the twentieth and twenty-first embodiment;

DESCRIPTION OF THE PREFERRED EMBODIMENTS

Prior to embodiments of the present invention, the principle of a Doppler measurement method using ultrasonic beams, which is the same as that used in measuring a flow of blood, will now be explained, on which all of the following embodiments are based.

Figure 1:
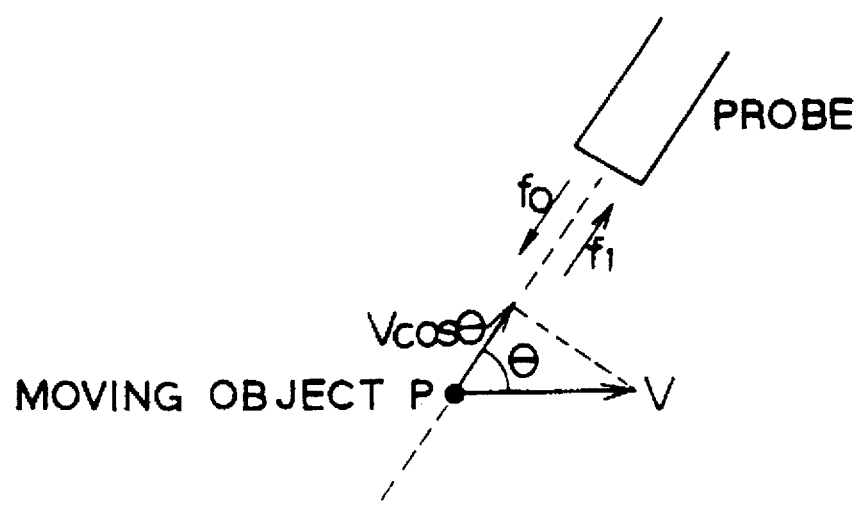
FIG. 1 is an explanation for Doppler measurement.

As shown in FIG. 1, when an ultrasonic beam having a frequency $f_0$ is radiated from a ultrasonic probe to an object P moving at a velocity V, the echoed ultrasonic beam by the object has been shifted in its frequency by the Doppler effect. Taking the frequency of the echoed ultrasonic beam as $f_1$, a Doppler shift frequency $f_d$ ($=f_1-f_0$) can approximately be given by:

$$f_d = \{(2 \cdot V \cdot \cos \theta)/C\} \cdot f_0 \quad (1)$$

where C is a sound speed in living body, θ is an angle between the moving direction of the object P and the ultrasonic beam direction (in other words, an incidence angle of the beams against the moving object).

From the equation (1), the moving volocity V of the object P is given by $$V = \{C/(2 \cdot f_0 \cdot \cos \theta)\} \cdot f_d \quad (2)$$

This shows that if a doppler shift frequency $f_d$ is known, the movement volocity V of an object P can be derived by the equation (2).

It should be noted that a detectable signal as a doppler shift frequency is only a component of velocity "V×cos θ" in the ultrasonic beam direction, and the component of velocity perpendicular to the ultrasonic beams is not detectable. Further, the determination of the velocity V from the above equation (2) necessitates estimation of the angle θ (not equal to 90 degrees) by some methods as will be described later on.

Now, embodiments of the present invention will be described with reference to the accompanying drawings.

A first embodiment of the present invention will be described according to FIGS. 2 to 8. The first embodiment concerns an ultrasonic diagnosis apparatus by which two-dimensional color Doppler images of a cardiac muscle (i.e. the wall of a heart) can be obtained.

Figure 2:
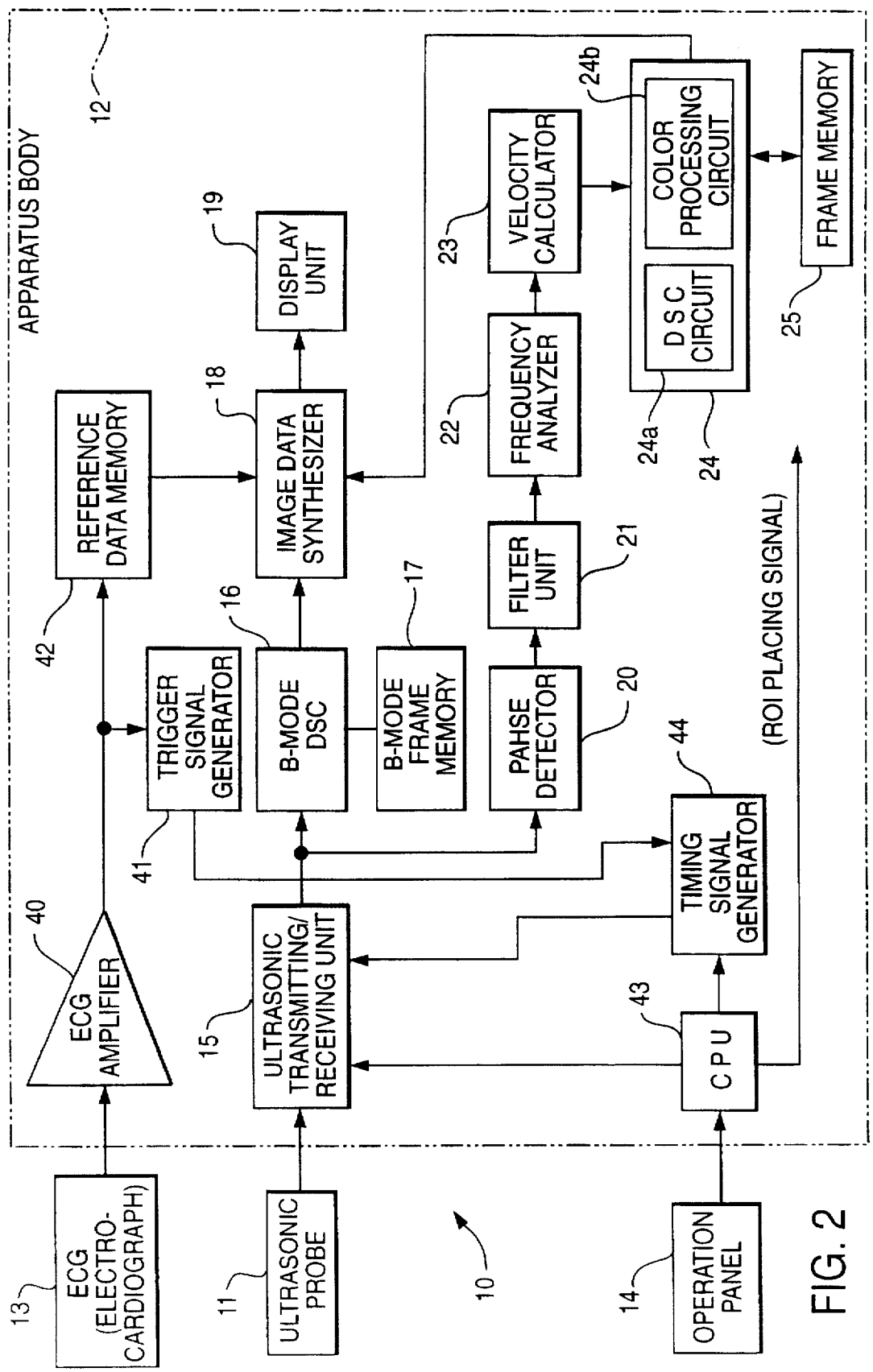
FIG. 2 is a block diagram showing an ultrasonic diagnosis apparatus of a first embodiment according to the present invention.

FIG. 2 is a block diagram schematically representing the whole construction of an ultrasonic diagnosis apparatus for color image of the the first embodiment.

The ultrasonic diagnosis apparatus 10 shown therein comprises an ultrasonic probe 11 for transmitting and receiving ultrasonic beams to and from an object to be examined, an apparatus body 12 for driving the probe 11 and processing received electric echo signals (reception signals) from the probe 11, an electrocardiograph (ECG) 13 electrially connected with the apparatus body 12, and an operation panel 14 by which an operator, such as a doctor, can input necessary information into the apparatus body 12.

Depending on the type of signal paths, the components of the apparatus body 12 are classified into three portions: an ultrasonic-probe-related portion, an ECG-related portion, and an operation-panel-related portion.

As the ultrasonic-probe-related portion, there is an ultrasonic transmitting/receiving unit 15 electrically coupled with the ultrasonic probe 11. Further, on the output side of the ultrasonic transmitting/receiving unit 15, there provided are two systems: for B-mode image, a B-mode DSC (digital scan converter) 16, a B-mode frame memory (FM) 17, an image data synthesizer 18, and a display unit 19, and in parallel to this, for color Doppler mapping, a phase detector 20, a filter unit 21, a frequency analyzer 22, a velocity calculator 23, a for color Doppler imaging DSC 24, a for color Doppler imaging.

The ECG-related portion comprises an ECG amplifier 40 elctrically coupled with the ECG 13 and a trigger signal generator 41 and a reference data memory 42 electrically connected to the output of the amplifier 40.

Further, the operation-panel-related portion comprises a CPU (central processing unit) 43 receiving operation information from the operation panel 14 and a timing signal generator 44 under control of the CPU 43. The CPU 43 includes a function to supply a ROI (region of interest) placing signal to other units necessary for ROI placement, in response to signals sent from an operator through the operation panel 14.

In the embodiment, as illustrated in FIG. 3, the ultrasonic probe 11 and ultrasonic transmitting/receiving unit 15 form a scanning means of the present invention. Also the phase detector 20, filter 21, frequency analyzer 22 and velocity calculator 23 form a velocity calculating means. The DSC 24, frame memory 25, image data synthesizer 18 and display unit 19 compose a display means.

The above units and devices will now be explained in detail.

The ultrasonic probe 11 comprises a phased array type transducer having a plurality of piezoelecric vibrations, which are driven by from pulsed driving voltages from the ultrasonic transmitting/receiving unit 15. Controlling delay times of the pulsed driving signals can change a scan direction to form an electronic sector scan. A delay time pattern in the ultrasonic transmitting/receiving unit 15 will be controlled by the CPU 43 on the basis of a reference time given by a timing signal from the timing signal generator 44. The ultrasonic transmitting/receiving unit 15 outputs pulsed driving voltages to the probe 11, the delay time pattern of the pulsed driving voltages being controlled correspondingly to the scan direction. When receiving a driving voltage, the transducer of the probe 11 transduces the voltage signal into a corresponding ultrasonic beam, which will be transmitted to a heart as a diagnostic portion of an object being examined. The transmittted ultrasonic beam is partly reflected as an echo signal by tissues of the heart, and returned to the probe 11, where the returned ultrasonic beam is oppositely transduced into a corresponding voltage signal called a reception signal. The reception signal will then be provided to a reception signal processor of the ultrasonic transmitting/receiving unit 15.

In the reception signal processor, by the same manner as the transmission, the reception signal is delayed for beam forming, with the result that the reception beam signal will be focused on a target focal point in a scan direction. The reception beam signal thus beam-formed is then detected and output to the B-mode DSC 16. At the B-mode DSC 16, the image data of the reception beam signal, which is in accordance with sector scanning, is changed into data of a standard television scanning and supplied to the image data synthesizer 18. In parallel with this, the B-mode DSC 16 will store a plurality of image data at an arbitrary cardiac timing into the B-mode frame memory 17.

On the other hand, the received echo signal processed in the transmitting/receiving unit 15 is also supplied to the phase detector 20 comprising a mixer and a low-pass filter for phase detection. The ultrasonic echo signal reflected at a moving portion, such as a cardiac muscle, has a Doppler shift in frequency by the Doppler effect. The phase detector 20 will carry out phase detection for the Doppler shift frequency to extract and output only a Doppler shift signal having lower frequencies to the next filter unit 21.

Figure 4:
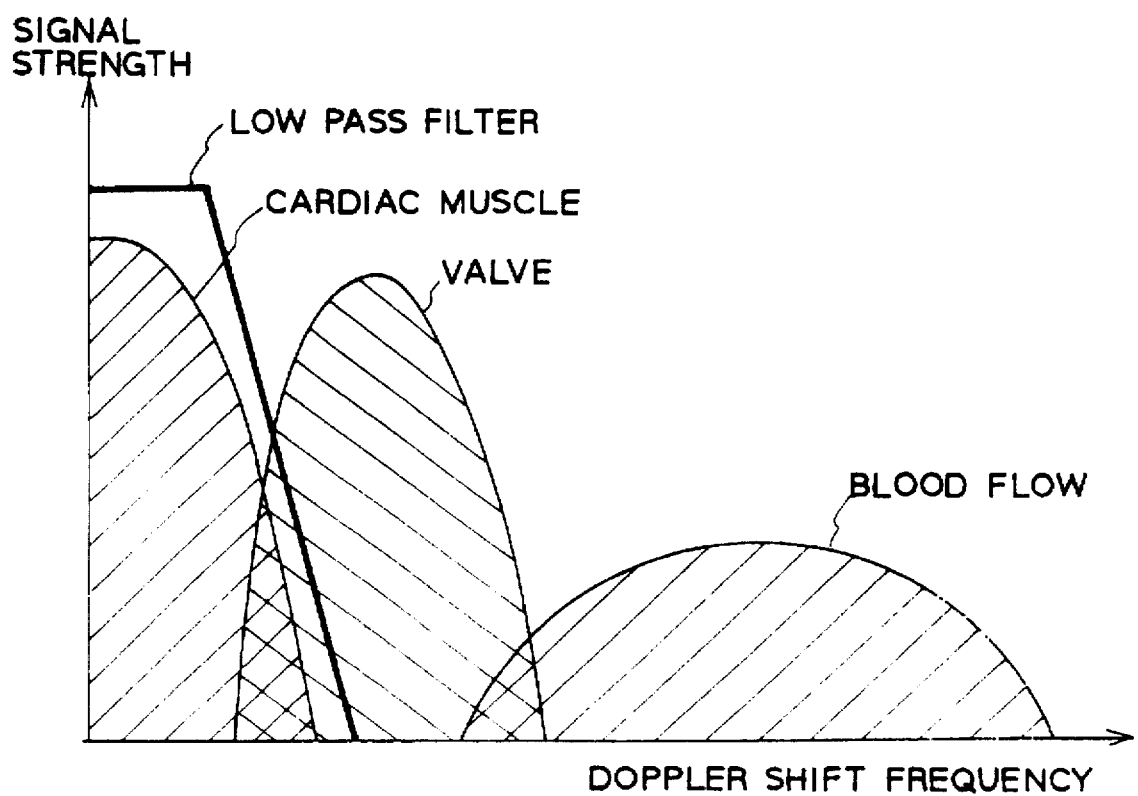
FIG. 4 is a graph representing a character of a filter unit.

Utilizing a situation in which values of movement velocities of a cardiac muscle, a valve, and a blood flow have a relation of "cardiac muscle<valve<blood flow". As shown in FIG. 4, the filter unit 21 excludes from the phase-detected Doppler shift signal, unnecessary Doppler signals caused by valve motion, blood flow and so on (except a cardiac muscle movement). As a result, the Doppler signal of the cardiac muscle in an ultrasonic beam direction is extracted efficiently. In such a case, the filter unit 21 acts as a low-pass filter.

The above filter unit 21 is mounted in a color Doppler mapping apparatus for blood measurements, which has already been practically used. In such an apparatus, the filter unit functions as a high-pass filter to remove Doppler shift signals except that of blood flows. So exchanging filters between low-pass and high-pass filters therein enhances flexibility of the filter unit 21.

The filtered Doppler shift signal through the filter unit 21 is supplied to the next frequency analyzer 22, which adopts representative frequency analyzing methods of a FFT method and an auto-correlation method used for blood flow measurement with ultrasonic Doppler technique. In the frequency analyzer 22, physical values related to velocities are calculated for an observation time (i.e. time window) at each sampling volume of a scan plane. In detail, for example, at each scan positions (i.e. positions of sampling volumes), the FFT or auto-correlation method is used to calculate in real time mean Doppler frequencies (mean velocities of movement of an object) and variance values (i.e. turbulence factors of Doppler spectrum). Moreover, the FFT method is used for calculating, in real time, the maximum values of the Doppler shift frequencies corresponding to the maximum velocities of movement of an object at sampling volumes. The resultant velocity-related values are then sent, as color Doppler information, to the next vector-velocity calculator 23.

The vector-velocity calculator 23 is to calculate absolute velocities of movement of an object, such as a cardiac muscle, at each sampling volume point, using the following methods. Now the term "absolute velocity" means hereinafter a velocity V itself in a moving direction of an object, the velocity V being a vector quantity having a magnitude and a direction in the two-dimensional coordinate system of a scan plane. As explained before, the velocity of a moving object detected by the ultrasonic Doppler method is a component "V×cos θ" in an ultrasonic beam direction. In contrast, the velocity expected is an absolute velocity V. Estimation of the absolute velocity V will be done as follows:

(i) In this method, ultrasonic beams are each transmitted to an object through two directions from different aperture positions and incidence angles and an absolute velocity V is estimated on Doppler shift frequencies obtained by the transmission of the two beams.

(ii) From Doppler shift frequencies (radius components) on ultrasonic beams whose radiation directions are slightly different, but the same aperture, components in perpendicular directions to the beams (tangential components) are determined, and an absolute velocity V is estimated on the tangential components.

Although these estimation methods themselves have been adopted in a Doppler measuring appratus for blood flows, they are also applied to measurement of movement of a cardiac muscle and a blood vessel wall.

Now, the estimation of method (i) will be explained in detail according to FIGS. 5 and 6.

Figure 5:
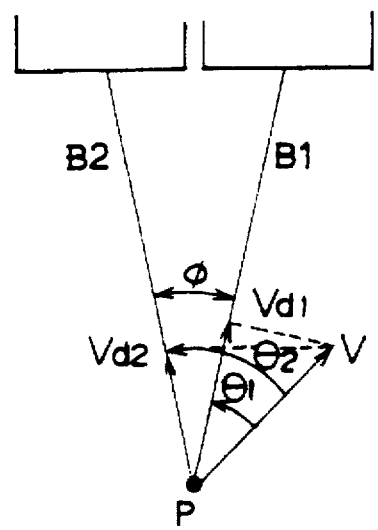
FIG. 5 is an explanation for measurement of an absolute velocity.

In FIG. 5, if the absolute velocity V of a moving object is assumed, components of velocities Vd1 and Vd2 in ultrasonic beam directions which can be estimated on Doppler shift frequencies obtained by two apertures 1 and 2, can be written as below.

$$Vd1 = V \cdot \cos \theta 1$$

$$Vd2 = V \cdot \cos \theta 2$$

Figure 6:
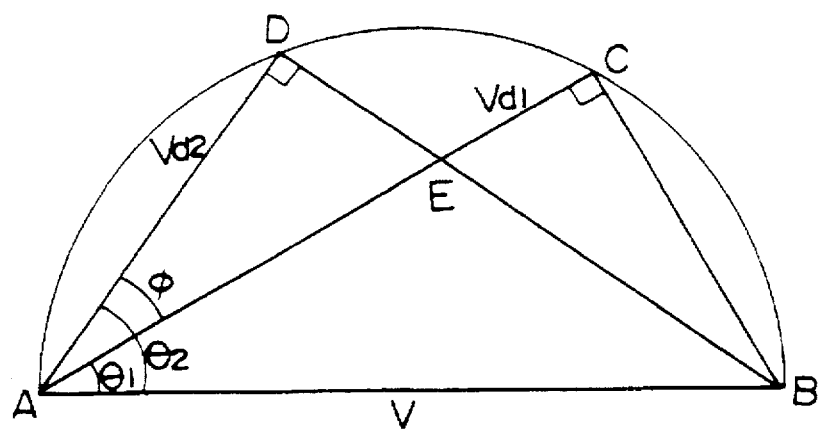
FIG. 6 shows a principle for calculating the absolute velocity.

These relations can be geometrically shown in FIG. 6, in which line segment AB=V line segment AC=Vd1=V·cos θ1 line segment AD=Vd2=V·cos θ2 is given. As the triangle ΔADE and the triangle ΔBCE are analogous to each other, line segment BC:line segment CE=line segment AD:line segment DE angle CBE=angle DAE=φ are established. Also as line segment AD=Vd2 line segment DE=Vd2·tanφ line segment CE=Vd1−Vd2/cosφ the equation line segment BC=line segment CE/tanφ

$$\begin{aligned} \text{line segment } BC &= \text{line segment } CE/\tan\phi \\ &= (Vd1 - Vd2/\cos\phi)/\tan\phi \\ &= Vd1 \cdot \cot\phi - Vd2/\sin\phi \end{aligned}$$

is given. Therefore, the line segment AB, that is, the magnitude of the absolute velocity V is given as below.

$$\begin{aligned} V &= \{(\text{line seg. } AC)^2 + (\text{line seg. } BC)^2\}^{1/2} \quad (3) \\ &= \{Vd1^2 + (Vd1 \cdot \cot\phi - Vd2/\sin\phi)^2\}^{1/2} \\ &= Vd1 \cdot \{1 + (\cot\phi - (Vd2/Vd1)/\sin\phi)^2\}^{1/2} \end{aligned}$$

As seen from the equation (3), if an angle φ between the two ultrasonic beams from the two apertures 1 and 2 is known, the absolute velocity V can be determined using the two Doppler shift outputs, with no relation to their incidence angles.

After the magnitude of the absolute velocity V has been determined from the equation (3), using a relation of $$Vd1 = V \cdot \cos \theta 1$$

gives $$\theta 1 = \cos^{-1}(Vd1/V) \quad (4)$$

thus the direction of the absolute velocity V being determined.

In order to calculate an absolute velocity V according to the above theory, the ultrasonic transmitting/receiving unit 15 is constructed such that it controls delay time patterns and apertures in transmission and reception of the two ultrasonic beams. In response to this, the Doppler shift outputs Vd1 and Vd2, which correspond to the two ultrasonic beams B1 and B2, are supplied alternately from the frequency analyzer 22 to the velocity calculator 23, where the above equations (3) and (4) are calculated.

Other estimation methods can be used, of course. In general, there is a relation of trade-off among estimation accuracy, a property of real time, and a size of circuit.

As mentioned, data of an absolute vector velocity V thus calculated at each sampling volume will be sent to the next DSC 24. The DSC 24 comprises a DSC circuit 24a for changing scanning and a color processing circuit 24b for coloring vecocity data with a lookup table. Data of two-dimensional absolute vector velocities calculated in the velocity calculator 23 are converted in form from ultrasonic scanning to standard television scanning in the DSC circuit 24a and then converted into color-display data in the color processing circuit 24b. The converted data will then be sent to the image data synthesizer 18.

Now the color display method of a cardiac muscle, whose processing is carried out by the color processing circuit 24b, will be explained. The color display is classified into three categories: (i) the magnitude of a velocity is only displayed, (ii) the direction of a movement and the magnitude of a velocity are displayed, and (iii) the direction of a movement is only displayed.

For the category (i), there are two ways: (i-a) one way uses the same color, but brightness changes according to the magnitude of a velocity, (i-b) the other way uses changed colors according to the magnitude.

Figure 7:
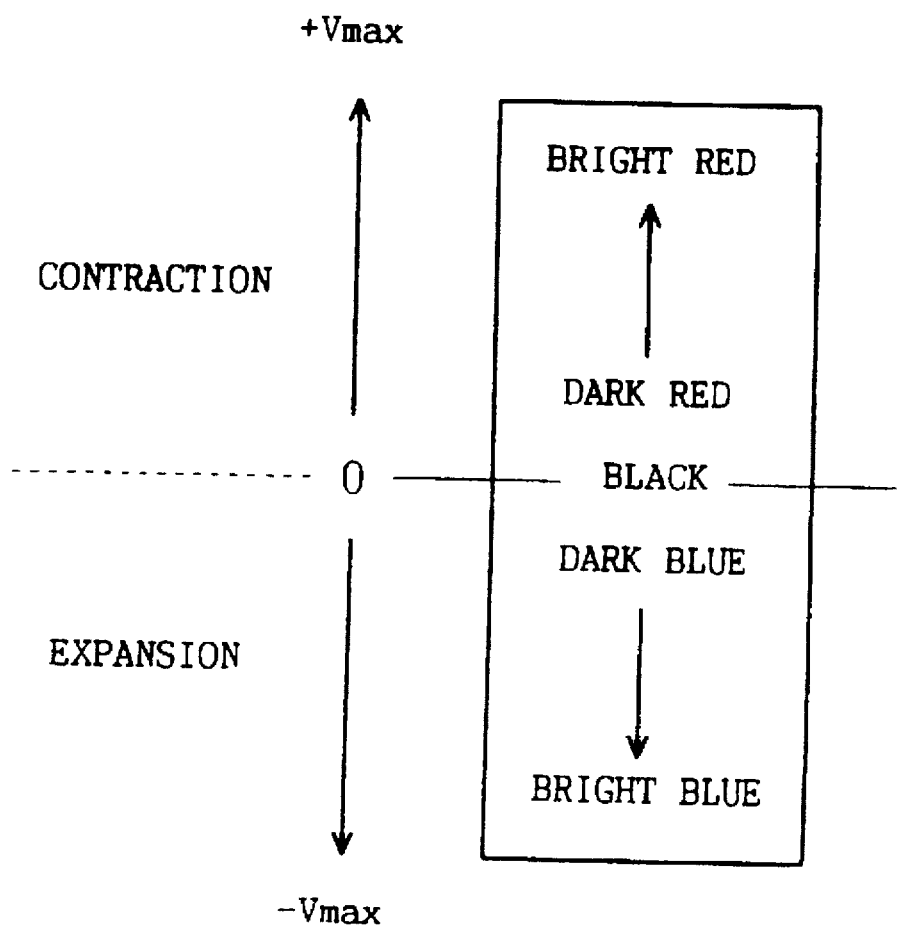
FIG. 7 shows an example of a color scale for coloring.

For the category (ii) of display, the direction is displayed by changed colors and the magnitude by changed brightness. With respect to display of the direction, applicable display ways are restricted according to conditions of velocities calculated. The color processing circuit 24b of this embodiment will determine color as shown in FIG. 7. That is, while the contraction of a cardiac muscle is colored as red and the expansion of it as blue, increased velocities are assigned to brighter red or blue (i.e. increased brightness). In conventionally used color Doppler imaging, a blood flow going toward the ultrasonic beams is displayed as red and a blood flow going away from the beams as blue. Further, the DSC circuit 24a stores a plurality of color Doppler images at an arbitrary cardiac timing into the frame memory 25.

On one hand, the ECG 13 will detect electrocardiographic signals of an object being examined at each cardiac time phase. The detected signals are sent, via the ECG amplifier 40, to both the trigger signal generator 41 and reference data memory 42. The reference data memory 42 memorizes the electrocardiographic signals at each cardiac timing and, if necessary, sends necessary signals to the image data synthesizer 18. The trigger signal generator 41 will output signals at the cardiac timings to the timing signal generator 44, where in response to the signals, reference pulse signals will be sent to ultrasonic transmitting/receiving unit 15 for transmission/reception of ultrasonic beams. Except this situation, the timing signal generator 44 is under control of the CPU 43 that controls the delay time pattern in the unit 15 in response to signals from the operation panel 14.

As mentioned so far, the memory data synthesizer 18 will receive B-mode image data from the B-mode DSC 16, color Doppler mode image data from the DSC 24, and electrocardiograph data from the reference data memory 42, if necessary. In the synthesizer 18, these input data are superimposed pixel by pixel, thus superimposed data being sent to the display unit 19 comprising a CRT.

Figure 8:
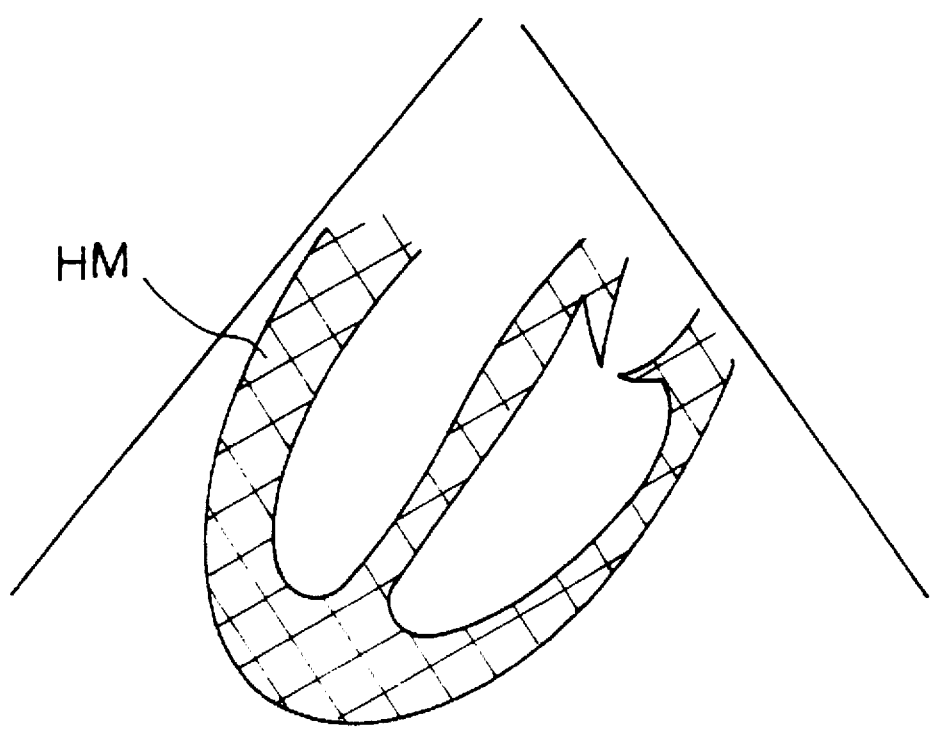
FIG. 8 is an example of velocity display of a cardiac muscle.
Figure 9:
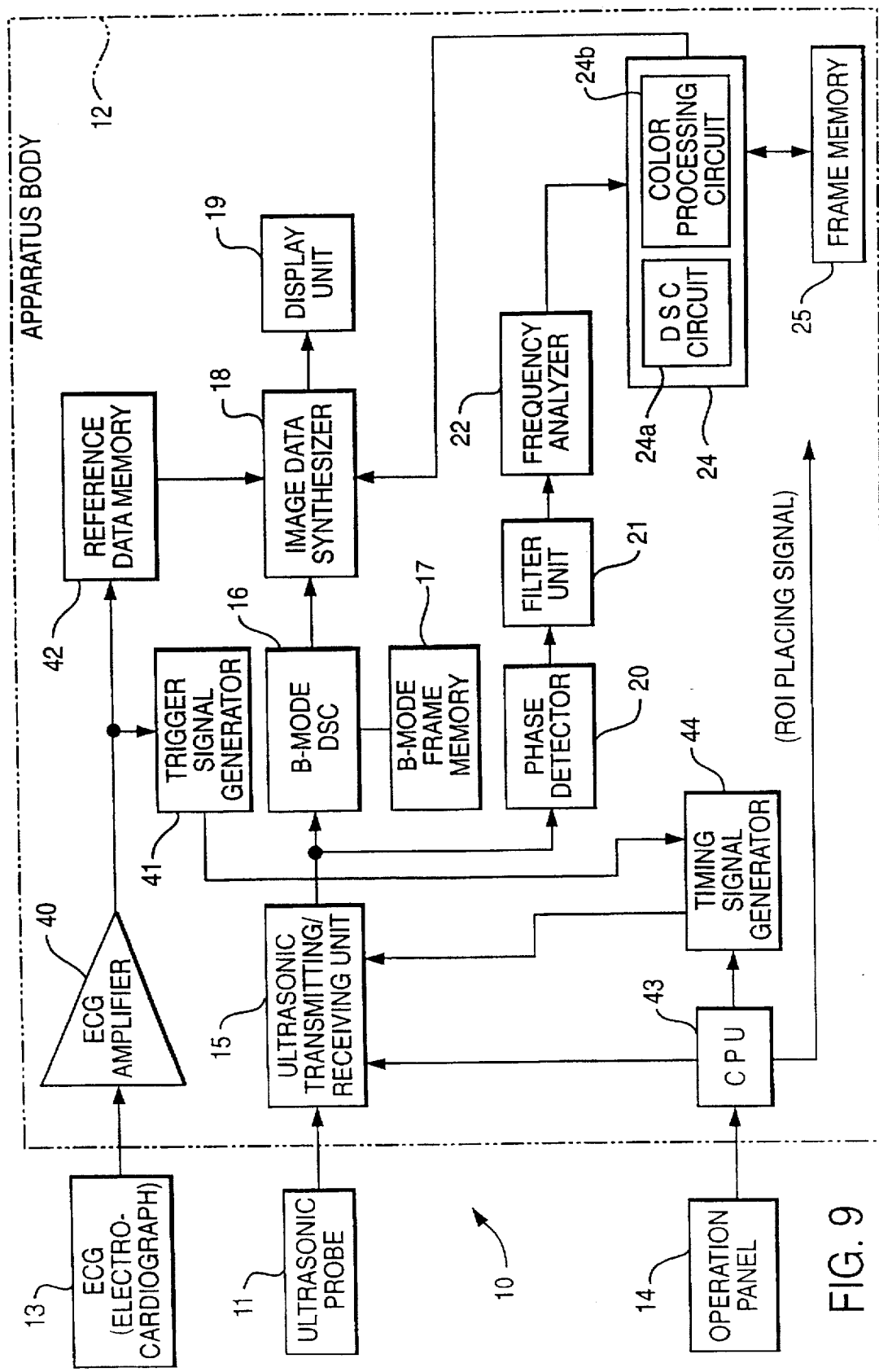
FIG. 9 is a block diagram showing a variation of the ultrasonic diagnosis apparatus of the first embodiment.

As a result, a cross-sectional image is displayed by the display unit 19, as shown in FIG. 8. The cross-sectional image consists of a B-mode tomographic image (black-white gradation) of a heart and a color velocity image (2-D) of the cardiac muscle of the heart colored, which is determined according to a color table shown in FIG. 7 and superimposed on the B-mode tomographic image. In FIG. 8, a part HM shown by hatching liens exemplifies a display of a cardiac muscle, in which images of blood flow and valves are removed by virtue of the filter unit 21.

For contraction, the displayed cardiac muscle HM in FIG. 8 becomes red in real time and for expansion, its cardiac muscle HM becomes blue in real time, repeating those alternately. In addition to changes in color, changes in magnitude of velocity in the contraction or expansion are expressed by changes in brightness of color red or blue. Hence, the movement velocity of a cardiac muscle HM, in particular, an absolute velocity in a moving direction is able to be displayed in real time by color with high accuracy, thus providing diagnostic images for quantitative and high-accuracy evaluation of functional degradation of a heart.

Further, in this embodiment, as two type of frame memories 17 and 25 for B-mode and color Doppler mode, cine loop playbacks such as a slow-motion playback, frame by frame playback and a dynamic image playback can be perfomed. In addition, a B-mode and color Doppler mode images at different cardiac timings can be displayed individually or in parallel.

Still further, it is possible to mount a Doppler filter and a FFT (fast Fourier transform) frequency analyzer for Doppler-display of a cardiac muscle.

In the present embodiment, a background image, on which a color Doppler mode image of a cardiac muscle is superimposed, has been explained as it is a B-mode tomographic image, but the present invention is not limited to the B-mode image. For example, an M-mode image may be displayed instead, if all of the units for B-mode imaging are replaced with units for M-mode imaging. Furthermore, an object being examined is not limited to the cardiac muscle of a heart, and the wall of a blood vessel can become an object (in this case, the cut-off frequency of the filter unit 21 is required to be adjusted to that of the blood vessel wall). It is also possible to display only a color Doppler mode image of an object in motion, without the above background images.

As seen from conventional images such as a B-mode image and a color Doppler image of blood, for making clear correspondence to signals such as an electrocardiographic signal, it is also effective to display a cardiac muscle color Doppler image together with the signal on the same screen and to display with a time difference from an R-wave of an electrocardiographic signal.

Now, some other variations derived from the first embodiment will be explained FIGS. 9 to 14.

In regard to an absolute velocity V, instead of vector quantities that have been stated so far, a scalar component Vd of an absolute velocity V in an ultrasonic beam direction can be calculated at each sampling volume and can be color-displayed as a representative of movement of a cardiac muscle, thus providing proper diagnostic information about its movement. In order to display velocity components Vd, there is an apparatus shown in FIG. 9, where the output data from the frequency analyzer 22 will be sent directly to the DSC 24; the velocity calculator 23 is omitted (the other units are the same as the first embodiment).

Figure 10:
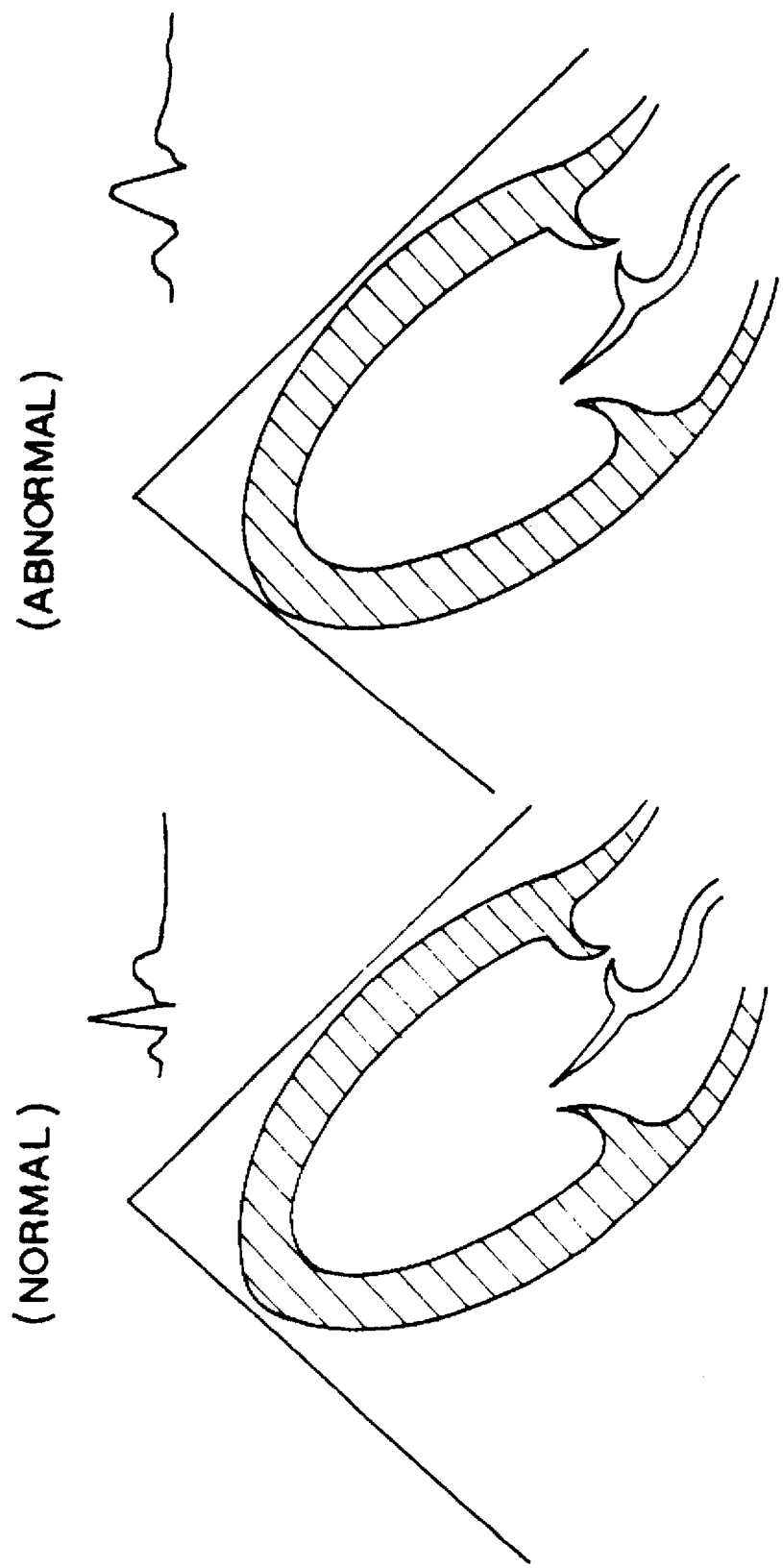
FIG. 10 is a variation for display in the first embodiment.

Another variation is shown in FIG. 10. The variation relates to a simultaneous display of normal heart beats and abnormal heart beats. To accomplish it, for instance, R-R intervals on an electrocardiograph are measured in the reference data memory 42, and the measured results are used for distinction between the normal and abnormal heart beats in both of the B-mode DSC 16 and DSC 24. Then, data of the normal and abnormal heart beats from the B-mode DSC 16 and CFM DSC 24 are combined in the memory data synthesizer 18 to display it on the display unit 19. As a result, as shown in FIG. 10, the color Doppler mode images of absolute velocities of a cardiac muscle in normal and abnormal heart beat states can be seen simultaneously, thus facilitating easy comparison between them.

Figure 11:
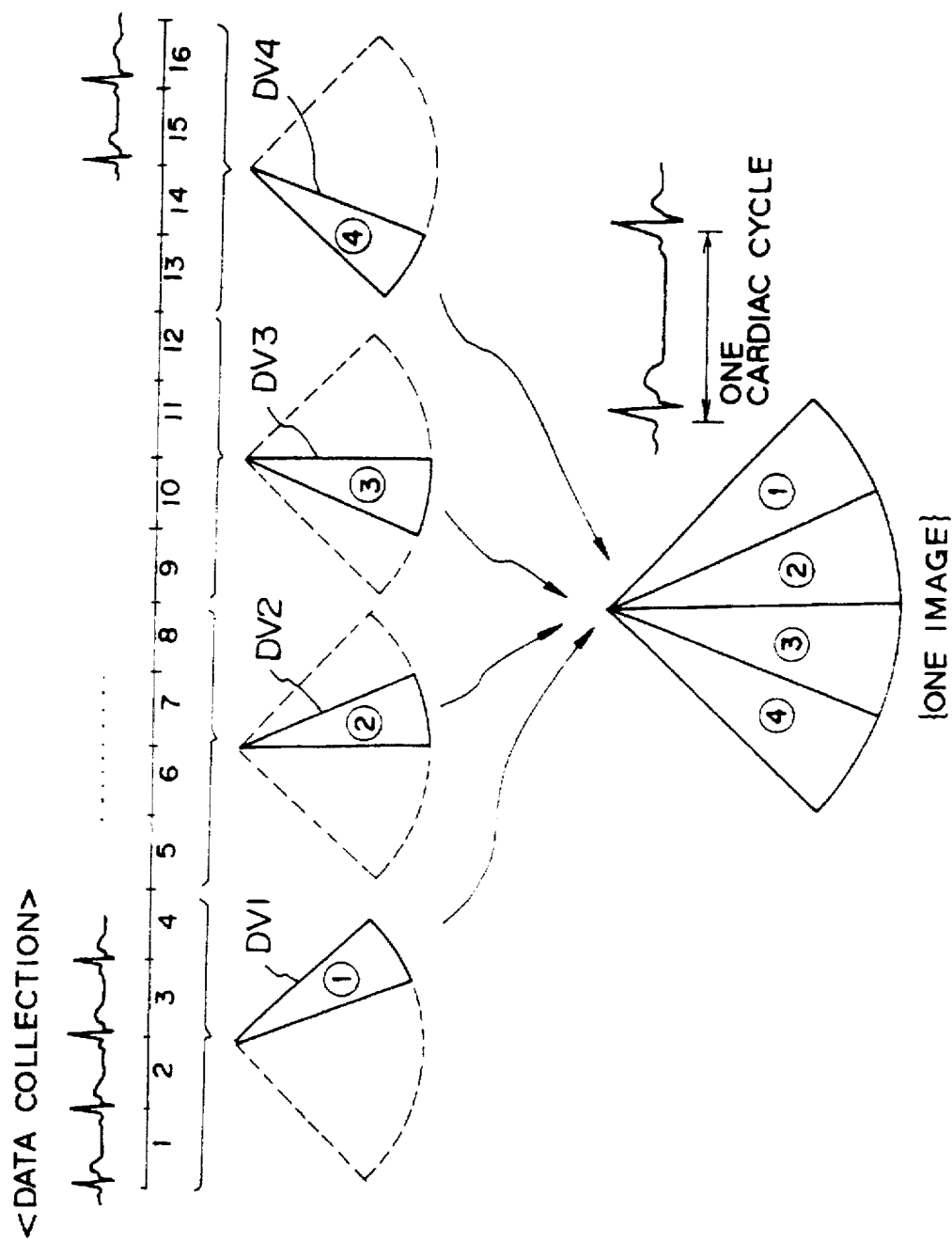
FIG. 11 is a variation for processing in the first embodiment.

A second variation is illustrated in FIG. 11. The variation concerns a superimposed display on synchronization with an electrocardiographic wave. On one frame image by ultrasonic beam scanning, owing to speckles of a cardiac muscle, there is a tendency that black dots are apparent on its images, in spite of the entire movement of the cardiac muscle at the same velocity. The black dots result in obstacles against observing construction and velocities on the images. Therefore, the spaces between scanning lines are narrowed to increase resolution, and velocity data are superimposed on a memory with color regions shifted with electrocardiographic synchronization.

For instance, as shown in FIG. 11, one frame memory is divided into four small sector regions DV1 to DV4 by shifting a angle of 22.5 degrees each. On the first sector region DV1, velocity data obtained by the first four-times scans are superimposed. Then, on the second region DV2, velocity data obtained by the second four-times scans are superimposed. Also, for the third and fourth regions DV3 and DV4, the same data store are repeated. Thus one frame of image will be completed in 16 heart beats, which are practically available, and the completed image will be displayed by cine-loop playback of one cardiac cycle. Such processing is mainly carried out by the timing signal generator 49 and frame memory 25 in FIG. 2.

Superimposing the frame data at the same cardiac timings prevents essentially the black dots on images due to speckles of a cardiac muscle, increasing image quality. In addition, scanning with color regions shifted and combining them can provide an image covering a whole cardiac muscle.

Figure 12:
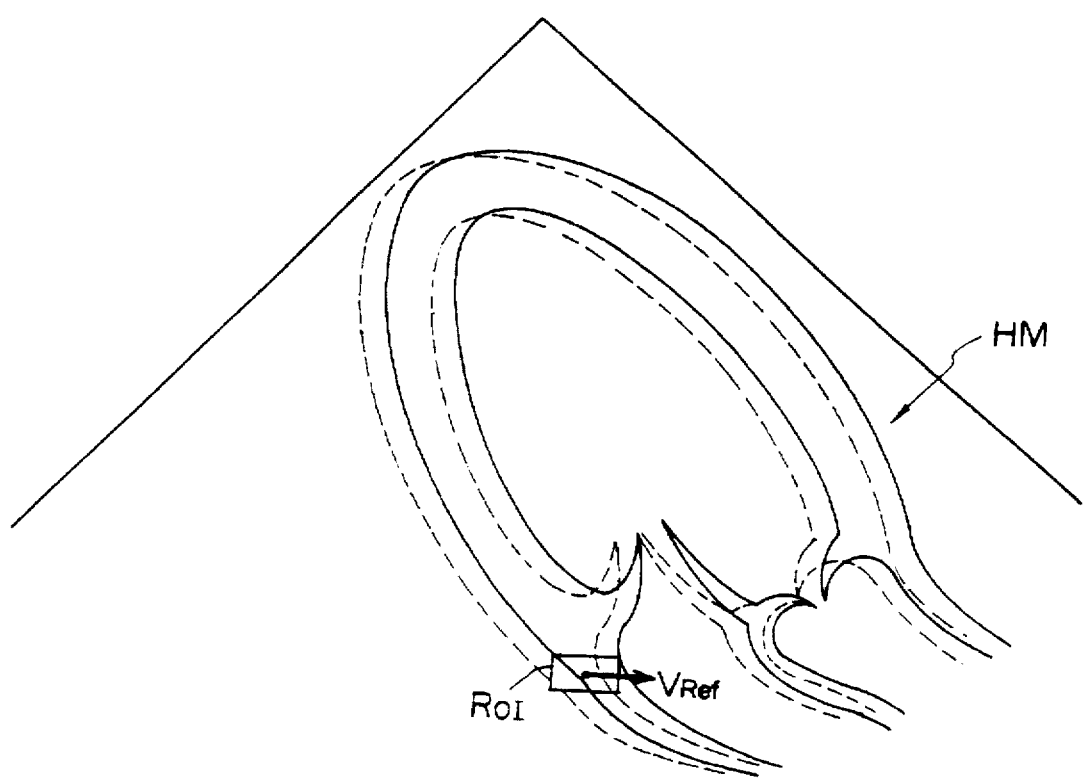
FIG. 12 is another variation for processing in the first embodiment.

Further, another variation is shown in FIG. 12, which relates to calculation of true velocities of motion. First, a reference point is assigned to a part of a heart which is not in motion (for instance cardiac skeleton), then the velocity of the reference point are subtracted from detected velocities at each sampling volume position, providing true motion velocities of a cardiac muscle.

Such processing are carried out by the frequency analyzer 22 or velocity calculator 23. On the display unit 19, as shown in FIG. 12 an operator places a region of interest (ROI) at the part of a cardiac skeleton, for example. The mean velocity or maximum velocity is calculated within the ROI, the calculated value being decided as a reference velocity Vref. Then, detected velocities at each sampling position are subtracted by the reference velocity Vref. As a result, this variation can provide velocity data having higher accuracy.

Figure 13:
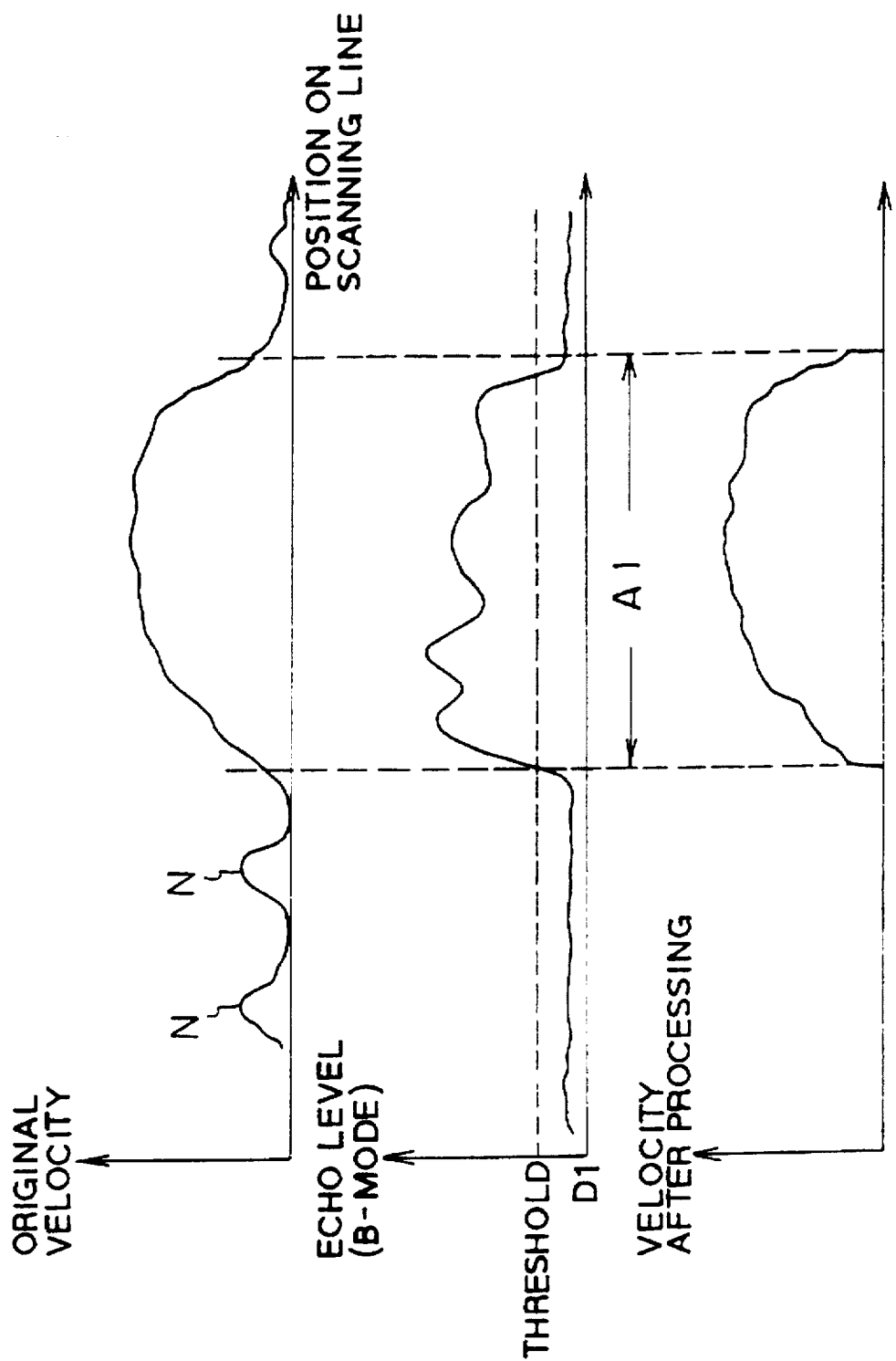
FIG. 13 is still another variation for processing in the first embodiment.

Still further, another variation is shown in FIG. 13, which relates to removal of random noises. This removal will be carried out, for instance, by the image data synthesizer 18, utilizing the characteristics that echo level is higher than other portions on a tomographic image of a heart.

In detail, on a B-mode image, a range having brightness values more than a threshold level D1 (that is, a range A1 in FIG. 13) is extracted. Then, for the movement velocities in the extracted range, color display is done. In the example of FIG. 13, for original velocity data output from the DSC 24, data corresponding only to the range A1 remains as shown therein and is displayed. In consequence, random noises, shown as N and N in FIG. 13, occuring from a part except a cardiac muscle, are surely removed, thus increasing image quality.

Figure 14:
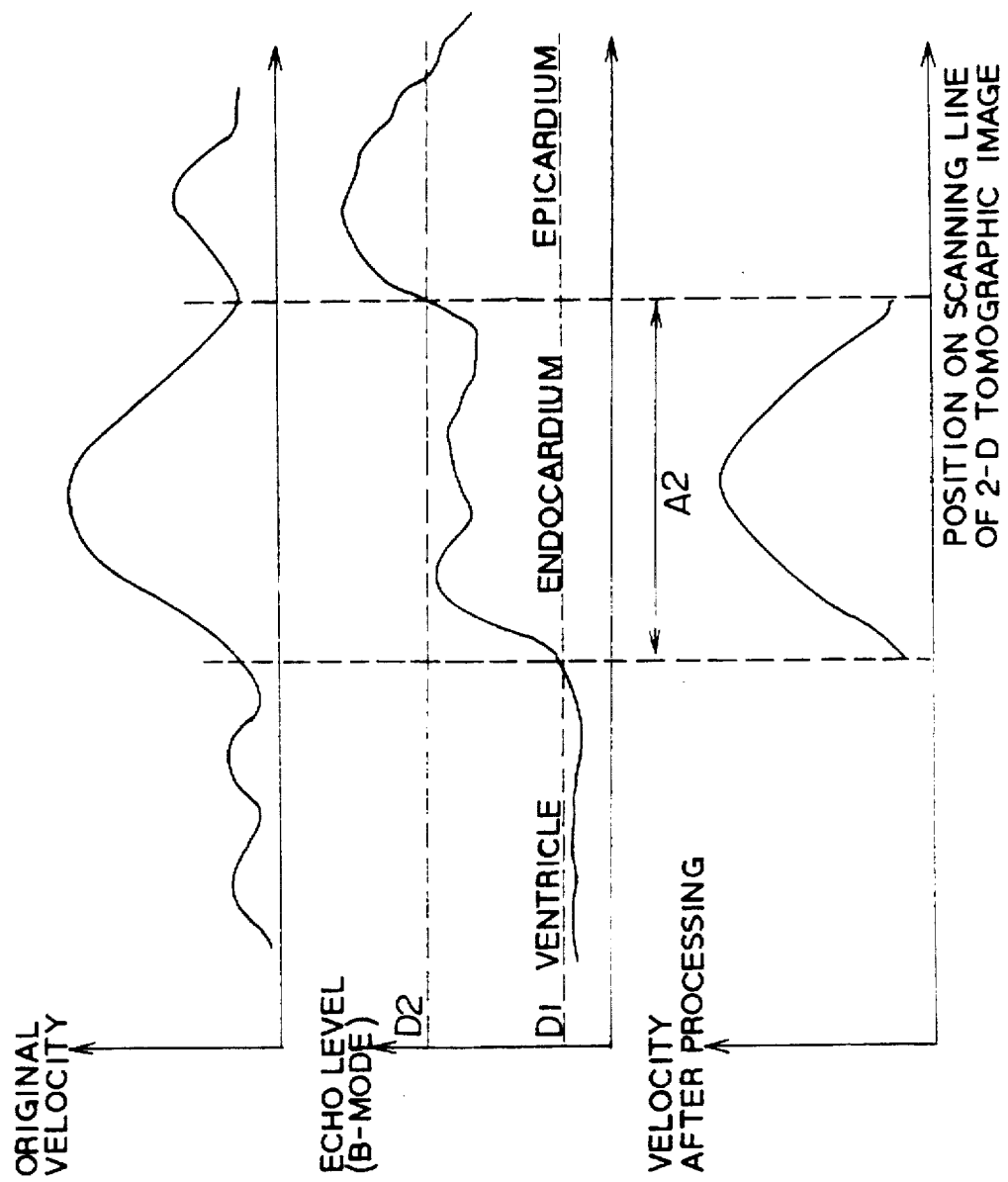
FIG. 14 is still another variation for processing in the first embodiment.

Still further, another variation is shown in FIG. 14. This variation relates to removal of velocities with respect to the epicardium of a heart. When observing movement of an endocardium on the display unit 19, the coloring of the epicardium is sometimes an obstacle to observation.

Threrefore, a property that echo level of the epicardium is larger than that of the endocardium is utilized. On a B-mode image, as shown in FIG. 14, data having brightness values more than a threshold level D2 are deleted, and data in the range A2 having brightness values less than the threshold level D2 and more than a threshold level D1 (D1<D2) are only adopted. The threshold level D1 is placed to combine with the aforementioned variation according to FIG. 13. Such processing will be done in the image data synthesizer 18.

Hence, when diagnosing an endocardium, such a case will not occur that coloring of an epicardium becomes an obstacle and also images will be increased in quality.

Figure 15:
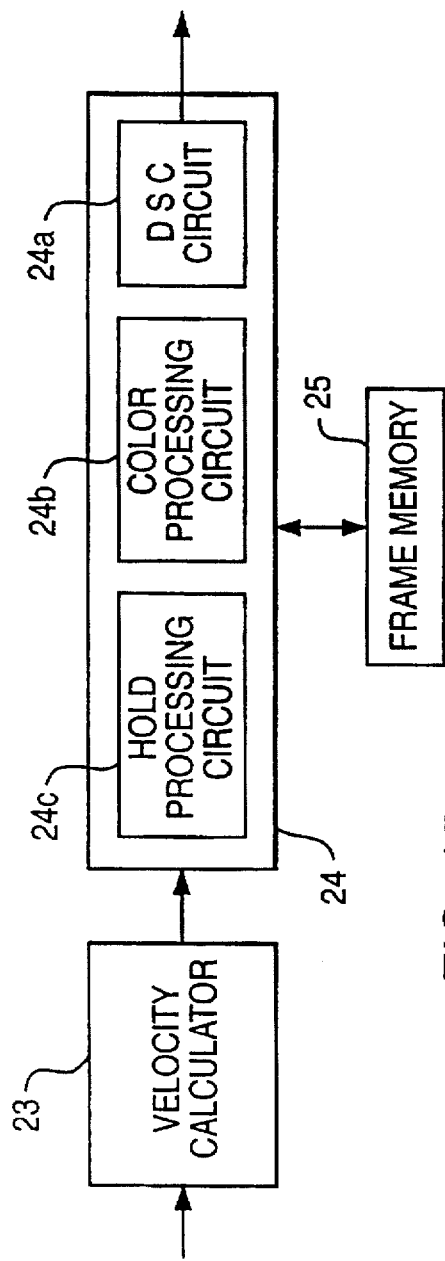
FIG. 15 is a block diagram partly showing an ultrasonic diagnosis apparatus of a second embodiment.

A second embodiment will now be explained according to FIGS. 15 and 16. In this embodiment (also in the following embodiments), the identical or equivalent components to the first embodiment will have the same reference numerals.

In the second embodiment, absolute velocities of a cardiac muscle thus calculated at each sampling volume position are displayed by a different method from the real-time display.

An ultrasonic diagnosis apparatus of the second embodiment has the same construction as that in FIG. 2, except for the DSC 24. The DSC 24, as shown in FIG. 15, further comprises a hold processing circuit 24c. As absolute velocity data (vector quantities) calculated by the velocity calculator 23 have been stored every frame in the frame memory 25, the DSC 24 reads out absolute velocity data of one heart beat from the frame memory 25. Then, at each sampling volume, the maximum velocity is calculated from the velocity data of one heart beat, the calculated maximum velocities are gathered for one frame to form frame image data. The maximum velocities thus calculated are the contraction maximum velocities Vmax . . . Vmax in contraction specified by output signals from the ECG 13. The contraction maximum velocities Vmax . . . Vmax are classified into either one of velocity ranges divided by 0<V1<V2<V3 and, according to the classification results, the contraction maximum velocities Vmax . . . Vmax are displayed with changed colors or brightness.

Figure 16:
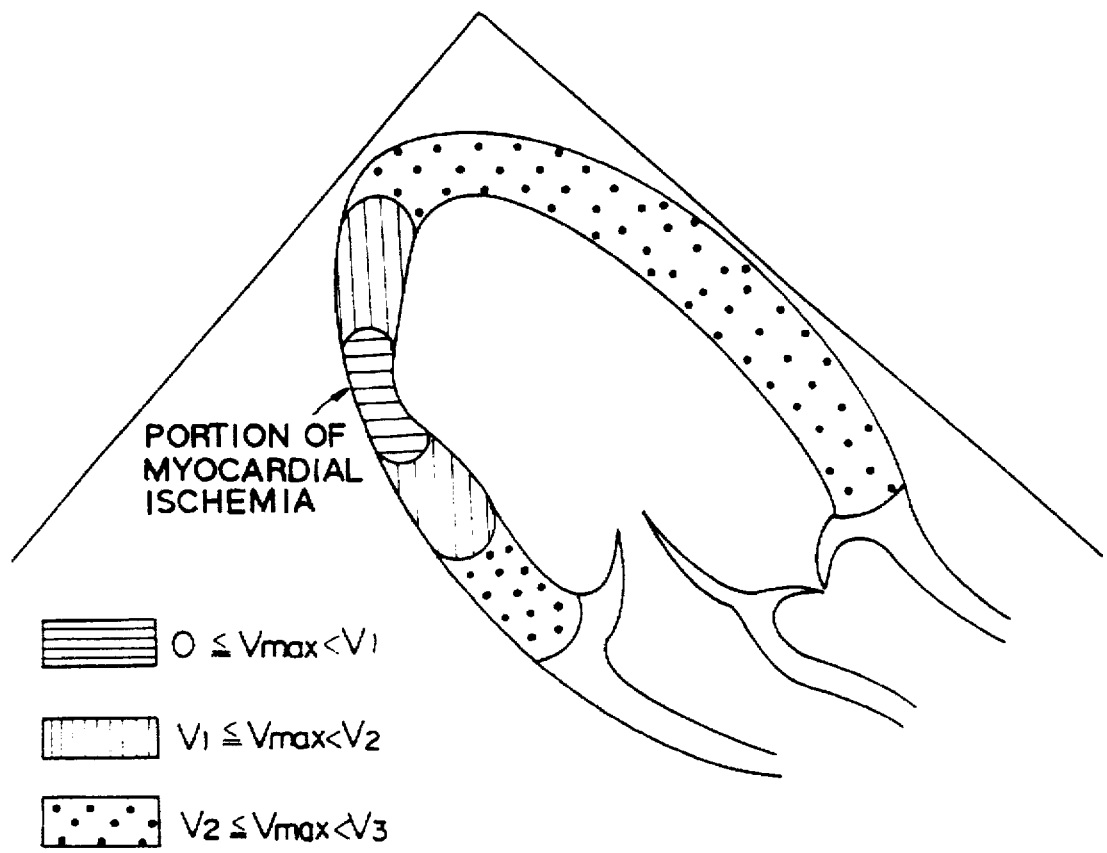
FIG. 16 is a display image in the second embodiment.

For example, as illustrated in FIG. 16, in case that Vmax is less than V1 and zero or more (low velocity range), a certain color or lower brightness in a given color is used, in case that Vmax is less than V2 and V1 or more (medium velocity range), another color or medium brightness in the given color is used, and in case that Vmax is less than V3 and V2 or more (high velocity range), yet another color or higher brightness in the given color is used. These classified image data are then sent to the image data synthesizer 18 to display in holding state on the display unit 19.

Therefore, on the display unit 19, as shown in FIG. 16, the color image of velocities is appeared such that they are classified according to the velocity ranges. This provides a clear image in distribution from low to high velocity ranges of the contraction maximum velocities Vmax . . . Vmax. If myocardial ischemia degrades activity of a local part of the cardiac muscle, the contraction maximum velocities Vmax . . . Vmax of the part is lowered. One can recognize the part at a glance. Further, from the ranges displayed by colors, it is easy to see changes in wall thickness of a heart over its cardiac cycle.

Variations for the above second embodiment will be described according to FIGS. 17 and 18. In the variation, when the maximum velocities obtained in real time is displayed in holding state, the maximum velocities of contraction and expansion are displayed like an after image for a period of time.

Figure 17:
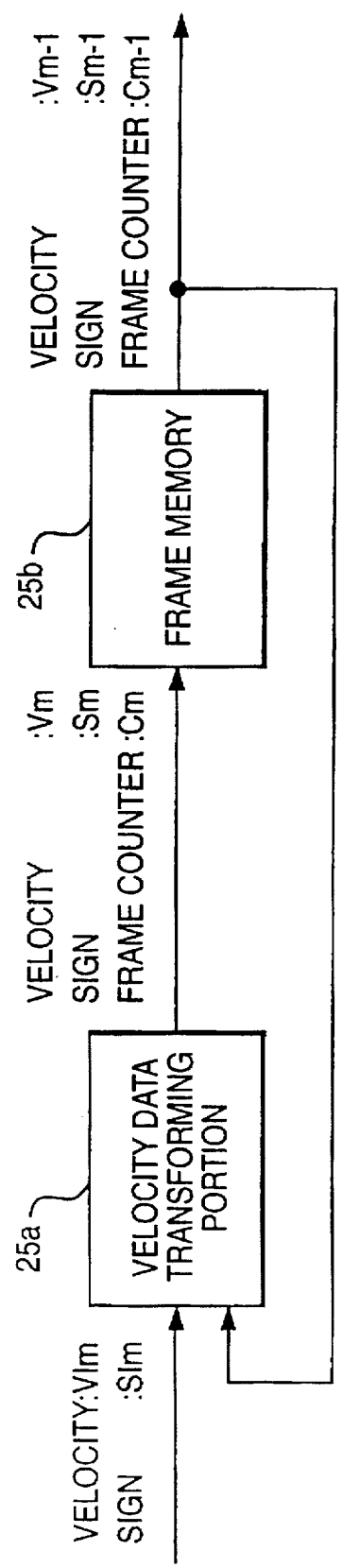
FIG. 17 is a variation for processing in the second embodiment.

In order to accomplish it, the frame memory 25 comprises, as shown in FIG. 17, a velocity data transforming portion 25a receiving velocity data from the velocity calculator 23 through the DSC 24, and a frame memory 25b receiving transformed data from the transforming portion 25a and outputting data of preceding frame. The output data from the frame memory 25b will be sent to the display unit 19 via the DSC 24.

Figure 18:
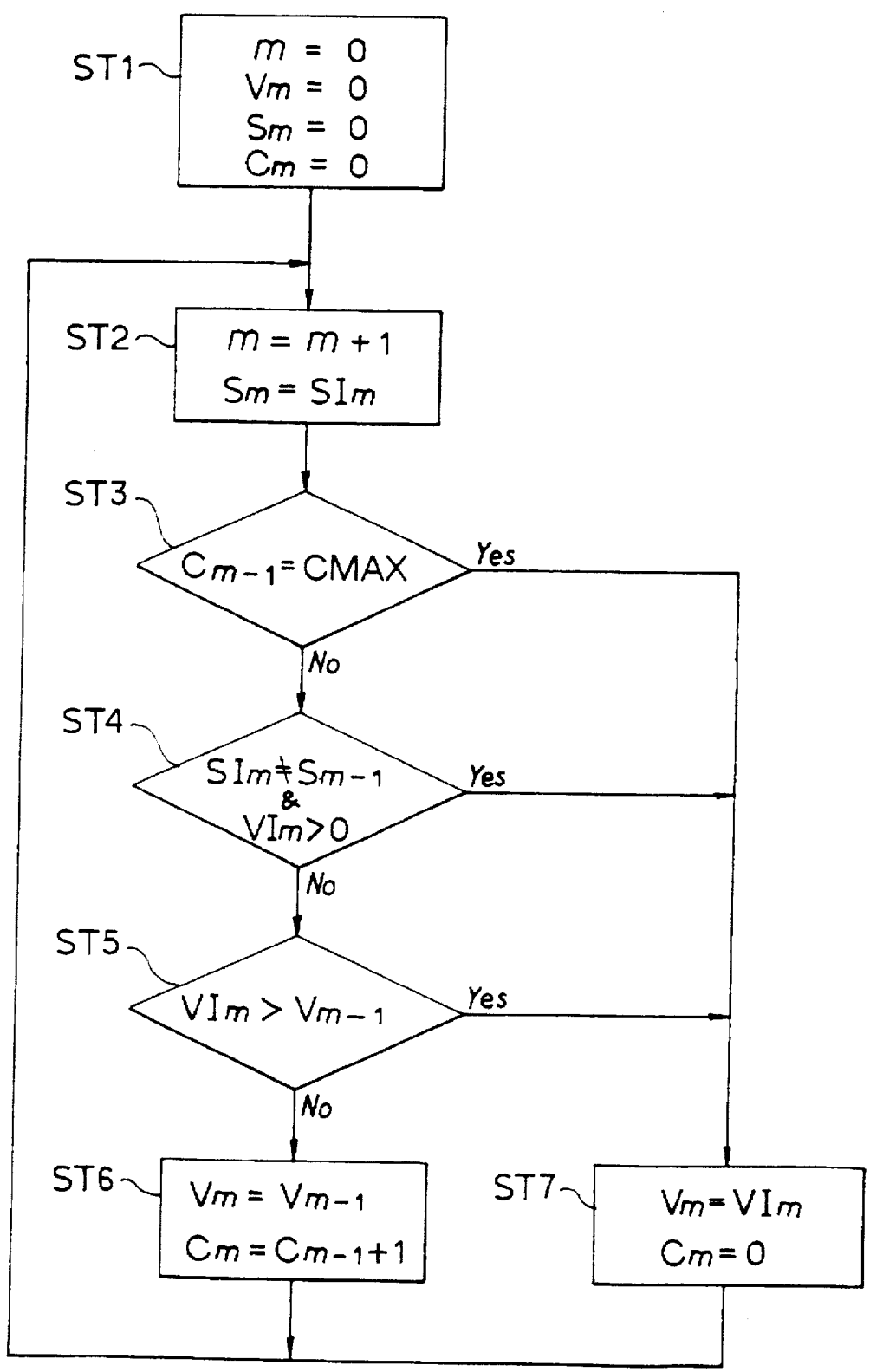
FIG. 18 is a flowchart representing process in the variation of FIG. 17.

The velocity data transforming portion 25a will carry out a procedure shown in FIG. 18. A velocity handled herein are to have directions toward for the beam and away from the beam, and the directions are to be judged by positive and negative of a sign. Let be that m is a number of ultrasonic frames, VIm is a velocity supplied to the transforming portion 25a, SIm is a sign of velocity supplied to the transforming portion 25a, Vm is an output velocity from the transforming portion 25a, Sm is a sign of an output velocity from the transforming portion 25a, Cm is a frame counter value for the ultrasonic frame=m, Vm−1 is an output velocity from the frame memory 25b, Sm−1 is a sign of an output velocity from the frame memory 25b, and Cm−1 is a frame counter value for the ultrasonic frame=m−1.

At Step ST1 in FIG. 18, initialization for ultrasonic scans and the frame memory 25b is done by m=0, Vm=0, Sm=0, Cm=0. At Step ST2, the ultrasonic frame number m is incremented by one (m=m+1), the first frame is specified, and the sign of a velocity at a given sampling volume point is updated (Sm=SIm). Then at Step ST3, it is judged whether the frame counter value Cm−1 reaches a maximum-hold frame period CMAX (Cm−1=CMAX?). When NO thereat, Step ST4 is done, in which it is judged if the velocity is yet changed in direction against the prior frame (SIm≠Sm−1 and VIm<0?). When NO at Step ST4 (i.e. the direction of the velocity has not changed), at Step ST5, it is judged whether the velocity VIm is larger than the velocity Vm−1 in the prior frame (VIm>Vm−1). If NO st Step ST6 (the velocity VIm is equal to or less than the velocity of the prior frame), Step ST6 will be done. In Step ST6, the velocity data Vm for memory writing of the frame m is placed by the Vm−1 of the frame m−1 (Vm=Vm−1) and the frame counter Cm is incremented (Cm=Cm+1). Then the processing will be returned to Step ST2. As explained above, when the maximum-hold frame period has not been reached, the velocity has not been changed in direction, and the velocity is smaller in magnitude than the prior frame, the holding of the maximum velocity is continued at Step ST6.

Under the continuation of the holding, when either one of the situations is occured: (i) the absolute value of the velocity has been larger than the prior frame (YES at Step ST5), (ii) the direction of the velocity has been changed, for example, from positive to negative (from contraction to expansion, YES at Step ST4), and (iii) the maximum-hold frame period CMAX has been reached (YES at Step ST3), the processing will immediately go on to Step ST7. At Step ST7, the velocity data Vm for memory writing of the frame m is placed by the VIm of the frame m (Vm=VIm) and the frame counter Cm is cleared (Cm=0). After this, the processing will returned to Step ST2. As a result, the holding display is stopped.

By the above processing, the displayed image is held like an after image for a certain period of time until either one of the aforementioned situations (i) to (iii) comes out. After the holding display like an after image, a real time image will appear with movement of a cardiac muscle traced in real time. That is, the image by the holding display will not disappear immediately and will not last long, the holding period becoming an appropriate one. The maximum velocities are color-displayed alternately for a certain period of time, corresponding to the contraction and expansion. Therefore, it is easy to observe the maximum velocities, facilitating a trace of a endocardium in end-systole and end-diastole. Further, black dots in an image due to the speckles of a cardiac muscle is reduced, increasing image quality.

A third embodiment will now be explained according to FIGS. 19 and 20.

Figure 19:
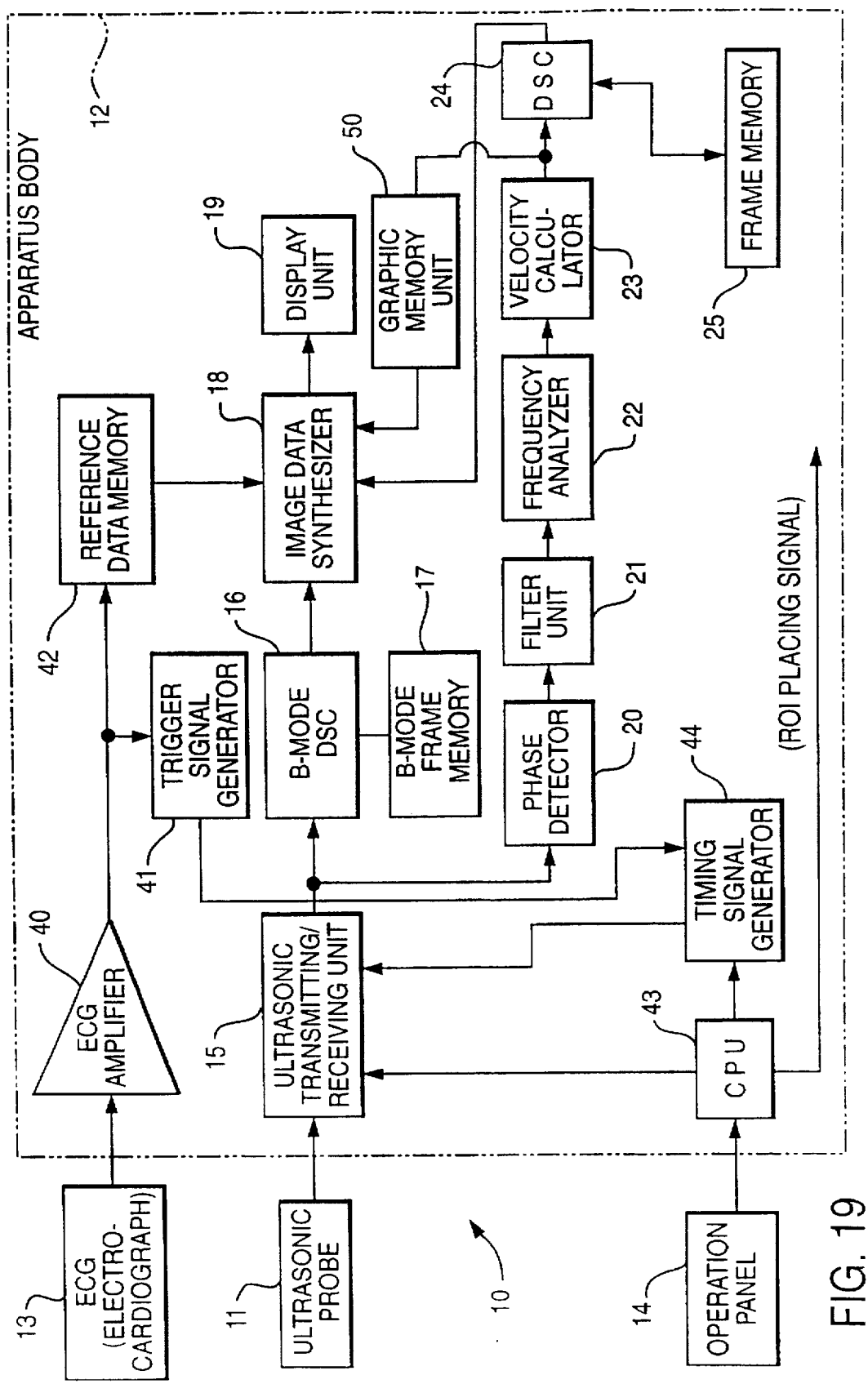
FIG. 19 is a block diagram showing an ultrasonic diagnosis apparatus of a third embodiment.

An ultrasonic diagnosis apparatus of the present invention, shown in FIG. 19, is such that dimensional absolute velocities at each sampling volume are displayed with vector symbols.

The apparatus shown therein comprises a graphic memory unit 50, to which data of absolute velocities (magnitudes and directions) calculated by the velocity calculator 23 are also supplied. The graphic memory unit 50 creates graphic data of arrows corresponding to the magnitudes and directions of the inputted velocities. The positions of the arrows are decided by properly tracing a contour of an annular cardiac muscle. In detail, the graphic data of the arrows are decided in a manner that the directions of absolute velocities are displayed by the directions of the arrows and the magnitudes of them are displayed as well by the lengths of the arrows.

The created graphic data in the graphic memory unit 50 will be sent to the image data synthesizer 18, in which the created graphic data are superimposed on images and data from the the B-mode DSC 16, color Doppler DSC 24, and reference data memory 42, the superimposed image data being sent to the display unit 19.

Figure 20:
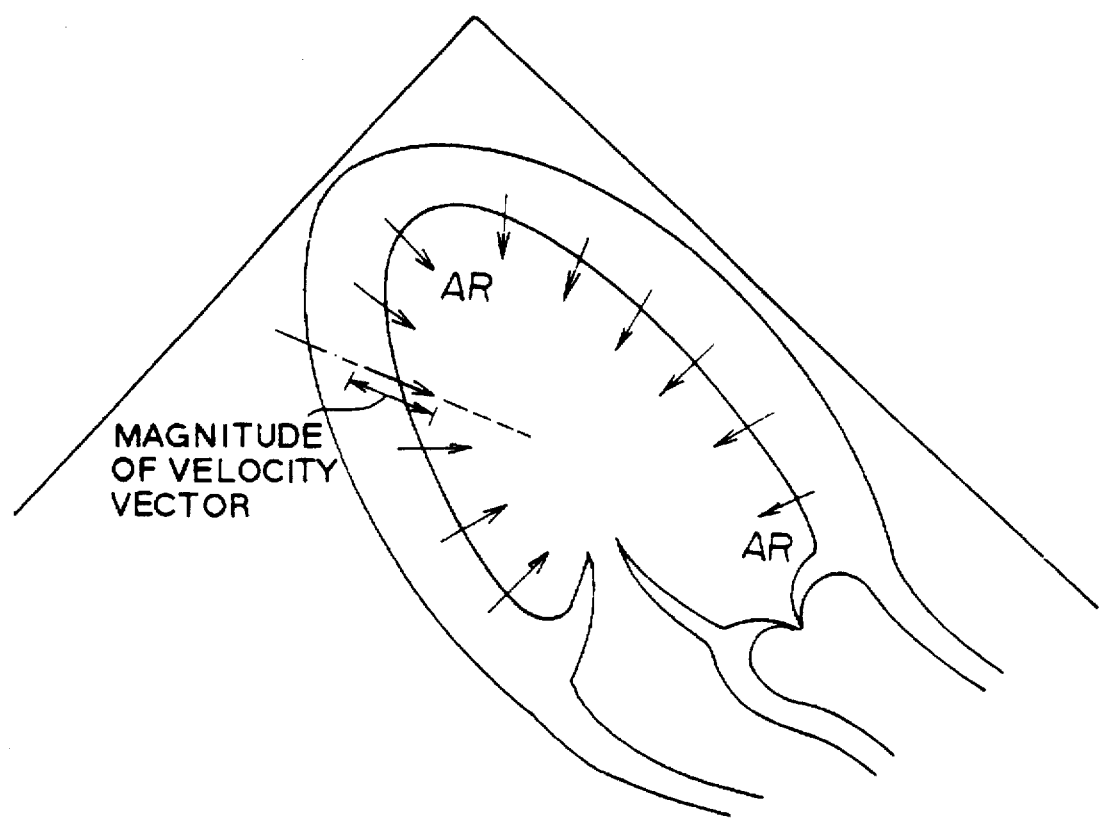
FIG. 20 is a display image in the third embodiment.

As a result, an image on the display unit 19 is shown as in FIG. 20 and on the image, a plurality of arrows AR ... AR representing absolute velocity vectors are superimposed on a color velocity image which is identical to that in the first embodiment. The directions of the arrows AR ... AR change depending on the contraction and expansion of a cardiac muscle and the magnitudes of the arrows AR ... AR change during each contraction and expansion, respectively. Therefore, the arrows AR ... AR are able to inform observers activities of a heart in real time.

In this embodiment, velocity vectors can be displayed in other forms: (i) the directions of velocity vectors are represented by those of the vectors and the magnitude changes of them by brightness changes of one color, (ii) the directions of velocity vectors are represented by those of the vectors and the magnitude changes of them by color changes. Also it is possible to display the directions of velocity vectors using arrows AR ... AR only whose directions change only.

A fourth embodiment will now be explained according to FIGS. 21 to 29.

The calculation process in the present embodiment differs from the first embodiment in which the vectors of movement velocities are calculated directly from Doppler data. But this embodiment focuses on characteristics of movement itself of a cardiac muscle and the directions of its movement are presumed on the basis of the characteristics for calculating the vectors.

Figure 21:
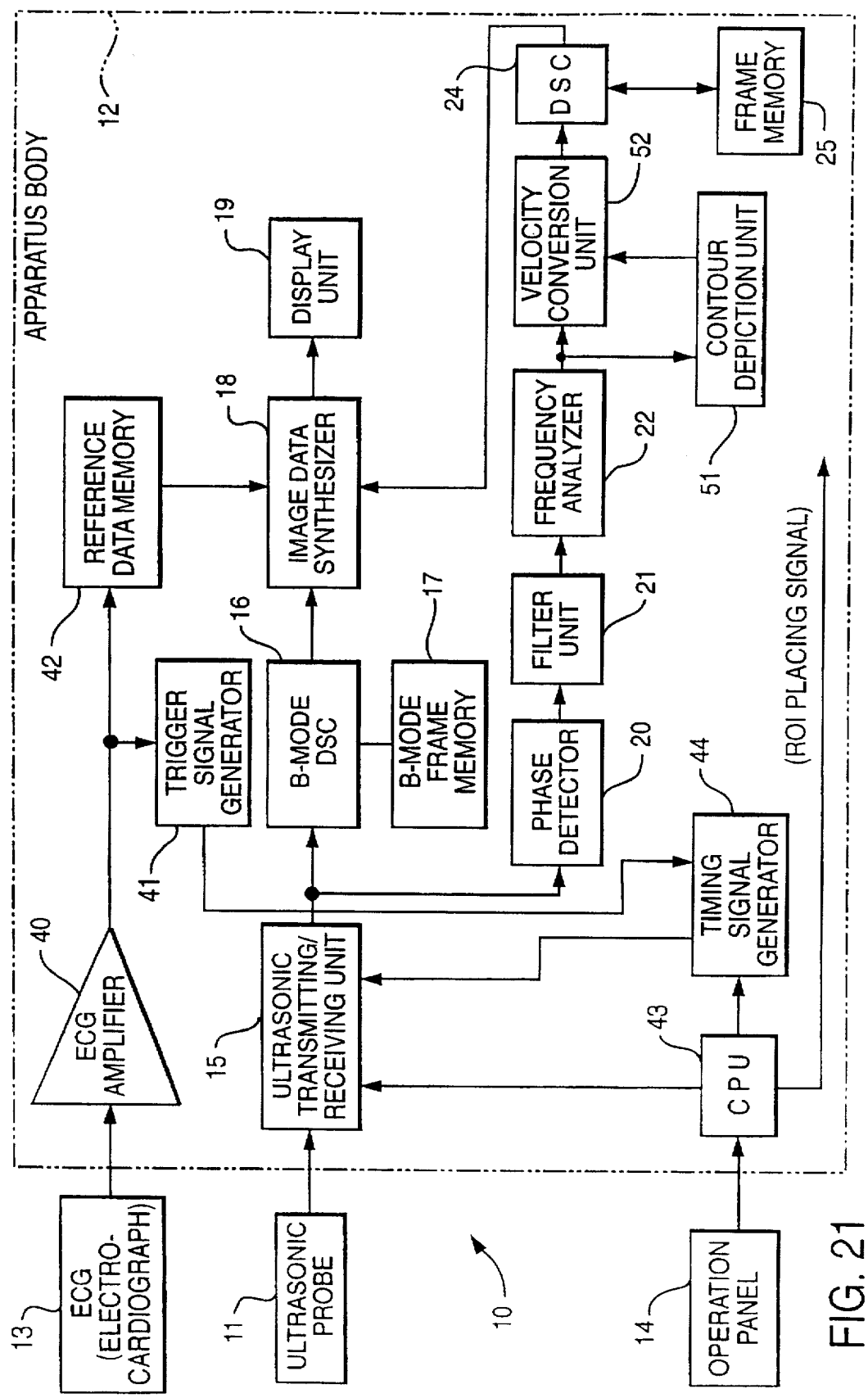
FIG. 21 is a block diagram showing an ultrasonic diagnosis apparatus of a fourth embodiment.
Figure 22:
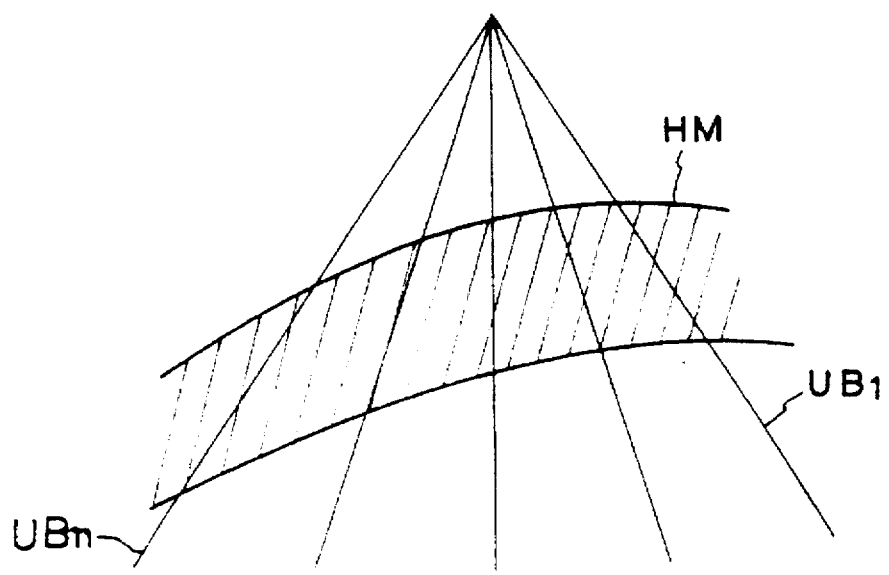
FIGS. 22 to 26 represent a procedure of contour depiction.
Figure 23:
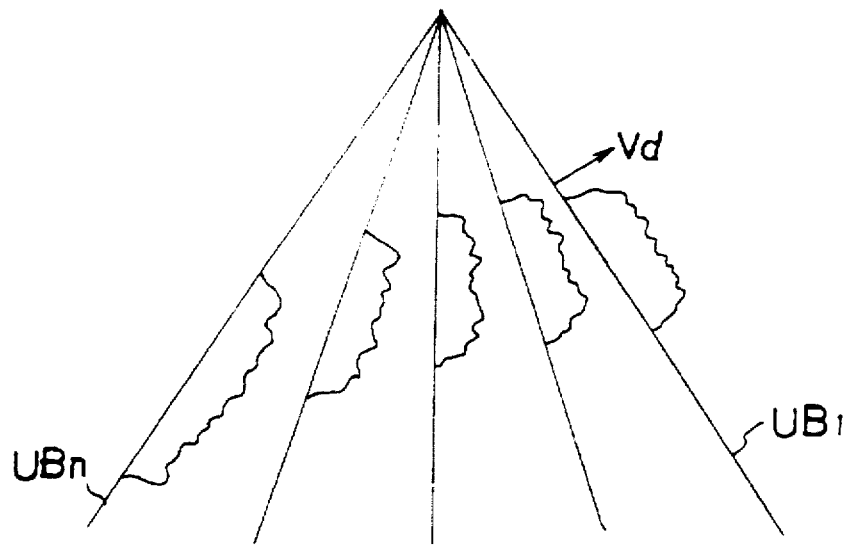
Figure 24:
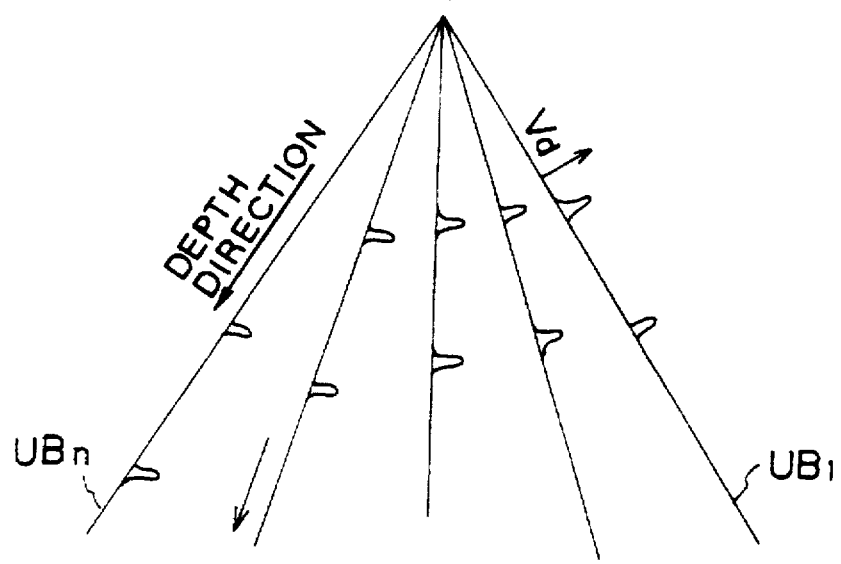
Figure 25:
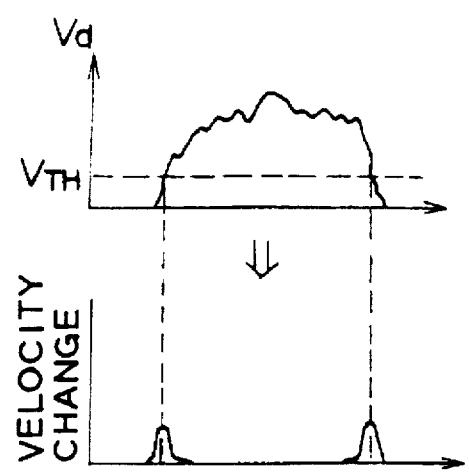
Figure 26:
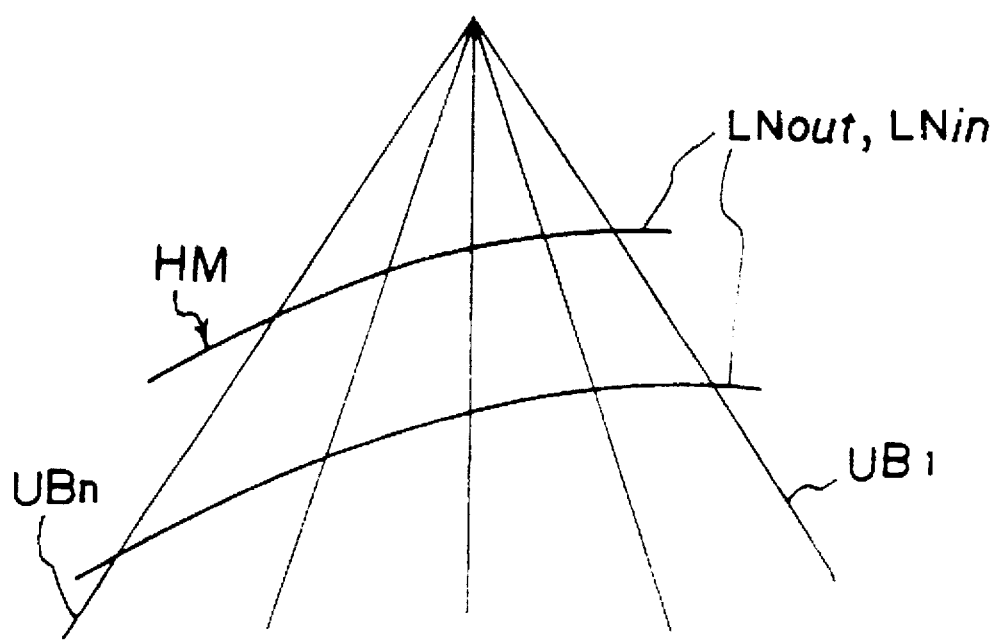

An ultrasonic diagnosis apparatus shown in FIG. 21 comprises a contour depiction unit 51 and a velocity conversion unit 52, both of which are connected with the output of the frequency analyzer 22 calculating vector velocity Vd ... Vd at each sampling volume in ultrasonic beam directions. The contour depiction unit 51 is to depict the contour of an endocardium. The velocity conversion unit 52 is to estimate absolute velocities in vector quantities in response to the supplied vector velocity Vd . . . Vd and contour information. Now the principle of depiction in the contour depiction unit 51 will be explained. In the first place, as shown in FIG. 22, a cardiac muscle HM as an object in motion will be scanned in sector by scanning lines UB1 to UBn consisting of ultrasonic beams. This sector scan makes the frequency analyzer 22 provide velocity data Vd . . . Vd (i.e. two-dimensional mapping data of movement velocities) for every scanning line, as pictorially shown in FIG. 23. Then, for every scanning line, edges of change in velocity are detected in each depth direction from the surface of a patient, as shown in FIG. 24. This edge detection is carried out as shown in FIG. 25, by setting a threshold level Vth. Then edges of change in velocity are also detected in each azimuth direction—a direction going to adjacent scanning lines. Connecting the edges obtained in the depth and azimuth directions forms the outer and inner contour lines LNout and LNin of the cardiac muscle, as shown in FIG. 26. The data of the contour lines LNout and LNin will be supplied to the velocity conversion unit 52.

In the velocity conversion unit 52, one of the following three methods is used for estimating absolute velocities.

Figure 27:
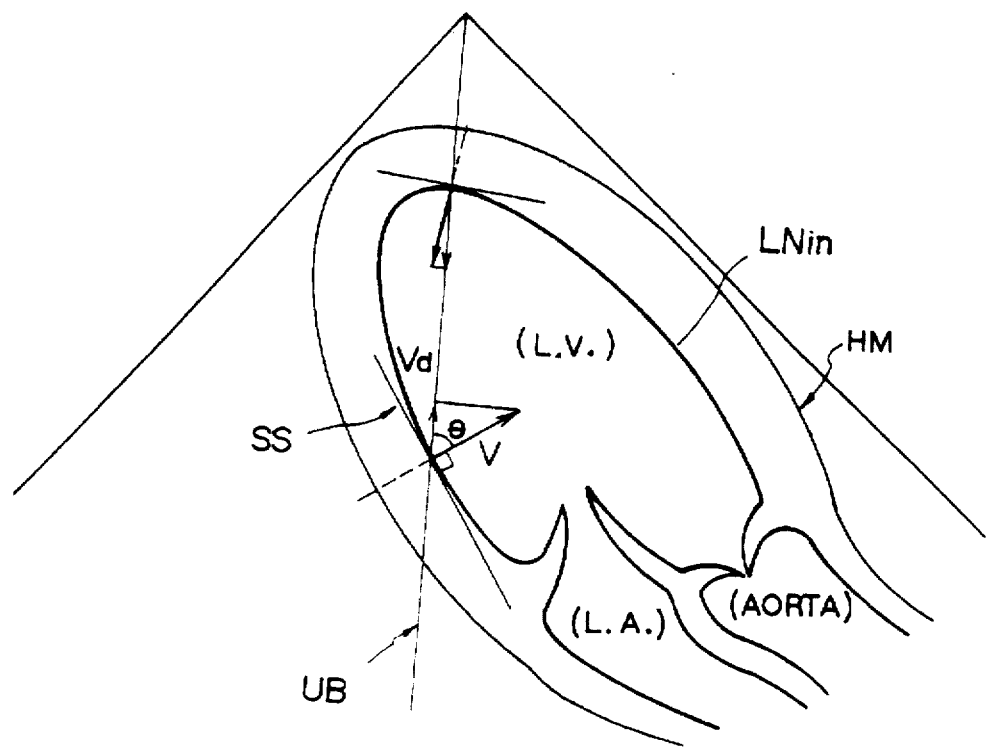
FIGS. 27 shows an example of estimation of the absolute velocity.

(i) A first method will be described in FIG. 27, where velocity components in directions perpendicular to the contour line LNin of an endocardium are determined to be absolute velocities. In detail, the conversion unit 52 will receive data of the contour line LNin. Tangents SS . . . SS are determined for the contour line LNtn at each sampling volume on each ultrasonic beam UB and then angles between the tangents SS . . . SS and the beams UB . . . UB are determined as "90°−θ", respectively. Then it is presumed that the movement directions at intersection of the beams UB . . . UB and the contour line LNin are perpendicular directions to the tangents SS . . . SS. Therefore, each of the absolute velocities V . . . V is given by $V=Vd/\cos \theta$, where Vd is a velocity component in an ultrasonic beam direction. In this case, the direction of an absolute velocity V is a perpendicular direction to a tangent SS.

Figure 28:
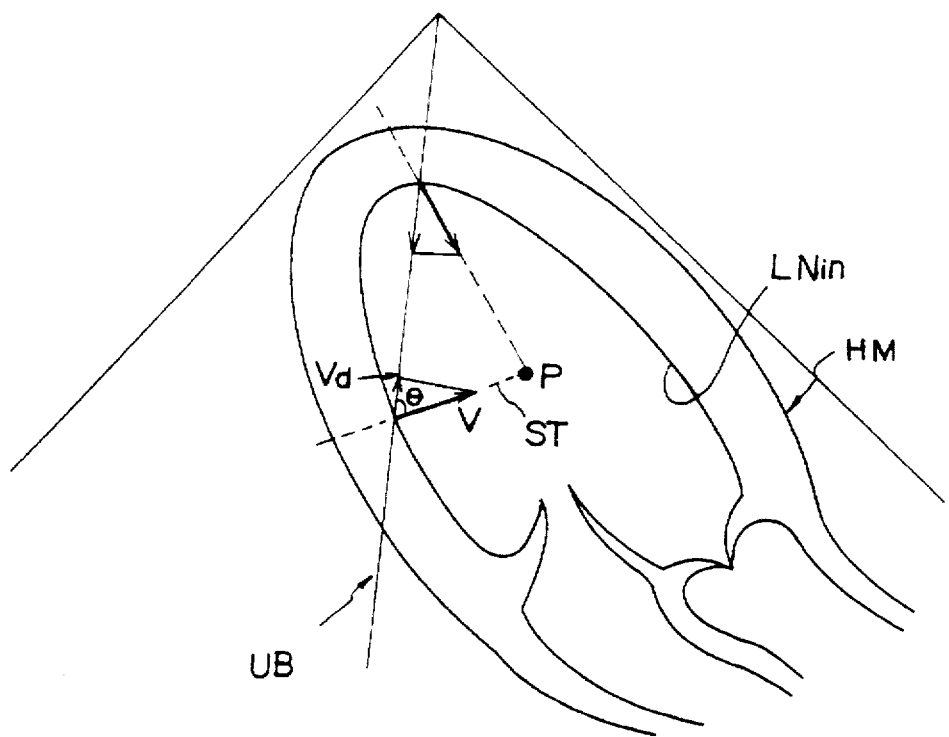
FIGS. 28 shows another example of estimation of the absolute velocity.

(ii) A second method is shown in FIG. 28. When it is presumed that a left ventricle contracts toward a fixed point and under the presumption, a velocity component in a direction toward the fixed point is determined to be an absolute velocity. The conversion unit 52 will receive data of the contour line LNin. Then, as shown in the figure, referring signals including an ECG signal, the center of gravity of the left ventricle (usually, the center of gravity in end-systole) are decided as the fixed point P. Further, at each sampling volume on each ultrasonic beam, each of the sampling volumes and the fixed point P are connected by a straight line ST and an angle between the straight line and an ultrasonic beam UB is calculated. Here, it is presumed that the cardiac muscle HM entirely contracts toward the fixed point P and it expands, provided the fixed point P is a center of the expansion. Therefore, an absolute velocities V is given by $V=Vd/\cos \theta$.

Figure 29:
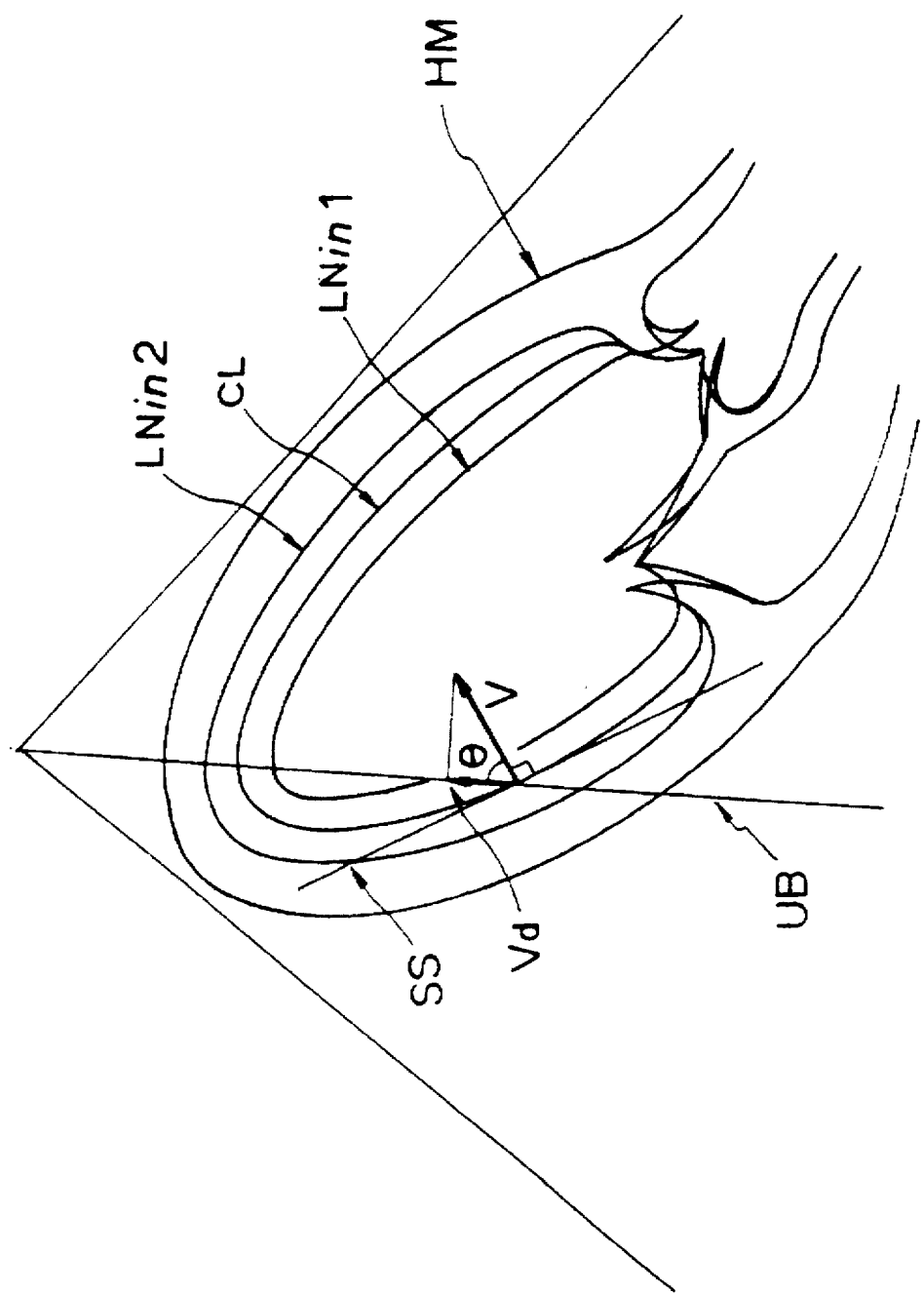
FIGS. 29 shows still another example of estimation of the absolute velocity.

(iii) A third method is explained according to FIG. 29. In this method, a center line between contours of an endocardium in end-diastole and end-systole are determined using signals such as an ECG signal and velocity components in directions perpendicular to the center line are designated as absolute velocities. The conversion unit 52 will receive data of the contour lines LNin1 and LNin2 of an endocardium each in end-diastole and end-systole. Then unit 52 calculates a center line CL between the contour lines LNin1 and LNin2, as shown in the figure. At each sampling volume on each ultrasonic beam, a tangent SS for the center line CL are determined by the unit 52 and an angle made between the tangent SS and the beam UB is calculated to be "90°−θ". Provided that a movement direction at each intersection made by the tangent SS and the ultrasonic beam UB is perpendicular to the tangent SS, the absolute velocities V at the intersection is given by $V=Vd/\cos \theta$.

Using one of the methods mentioned above, the absolute velocities V . . . V in vector quantities is presumed and calculated, their data being sent to the DSC 24 to be colored in the same way as the first embodiment and being displayed on the display unit 19. As a result, differently from the first embodiment, the directions of absolute velocities are not directly calculated, but they are obtained with considerably high accuracy.

Figure 30:
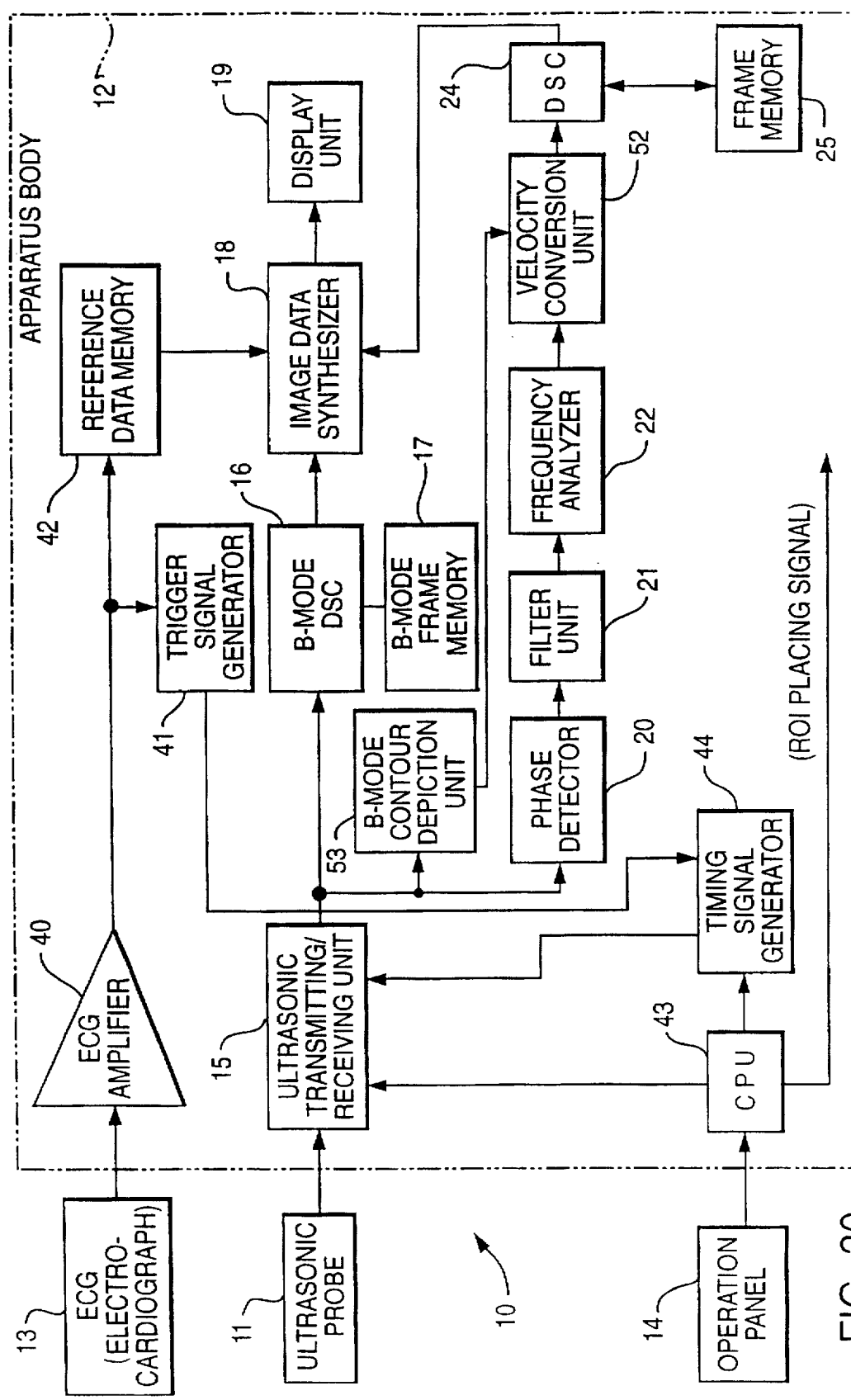
FIG. 30 is a block diagram showing an ultrasonic diagnosis apparatus of a variation of the third embodiment.

In the present embodiment, contour data of an endocardium have been extracted from a two-dimensional mapping data of movement velocities, but it is not limited to such a way. For example, as shown in FIG. 30, contour data can be obtained from B-mode image data. In FIG. 30, instead of the color Doppler contour depiction unit 51, a B-mode contour depiction unit 53 is disposed at the output of the ultrasonic transmitting/receiving unit 15, with the result that contour data obtained from a B-mode tomographic image are supplied to the velocity conversion unit 52.

A fifth embodiment will now be explained according to FIGS. 31 to 36.

The present embodiment relates to another display of absolute velocities.

Figure 31:
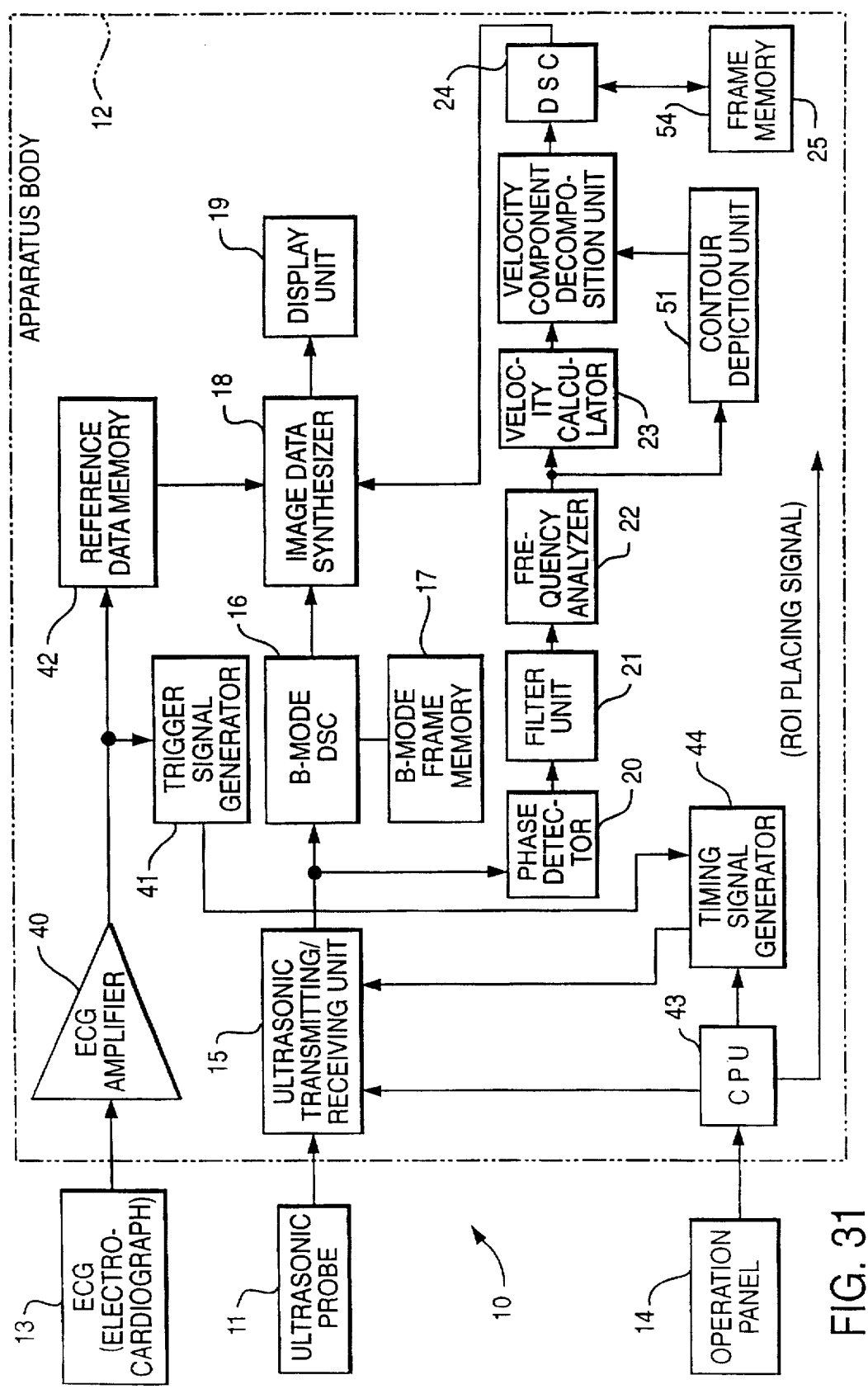
FIG. 31 is a block diagram showing an ultrasonic diagnosis apparatus of a fifth embodiment.

An apparatus 10 shown in FIG. 31 has, at the output of the frequency analyzer 22, the aforementioned vector—velocity calculator 23 and contour depiction unit 51, and between the calculator 23 and CFM DSC 24, a velocity component decomposition unit 54. Contour data will be sent from the depiction unit 51 to the decomposition unit 54.

The velocity component decomposition unit 54 receives absolute velocities V . . . V in vector quantity and decomposes each of them into components V1 and V2 in certain two directions. Then the unit 54, according to a ratio in magnitude of the velocity components V1 and V2, determines colors and brightness values by referring to a two-dimensional color scale later described, thus sending the data of the colors and brightness values to the DSC 24.

There are four ways of the velocity decomposition, which will be carried out in the unit 54.

Figure 32:
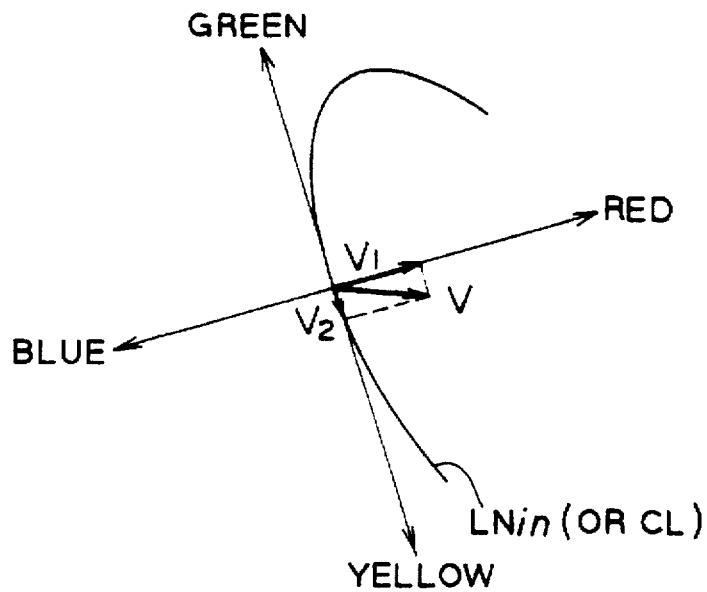
FIG. 32 is a variation showing decomposition of a velocity.

(i) A first decomposition way is shown in FIG. 32. An absolute velocity V is decomposed into a component V2 in a tangent direction at each sample volume point on the inner contour LNin (refer to FIG. 27) or center line CL (refer to FIG. 29) and a component V1 in a perpendicular direction to the tangent direction. Here, it is decided that one velocity component V1 in the perpendicular direction is assigned to be positive in a contraction direction and negative in the expansion direction and the other velocity component V2 in the tangent direction is assigned to be negative in a direction closer to the body surface and positive in a direction farther from it.

Figure 33:
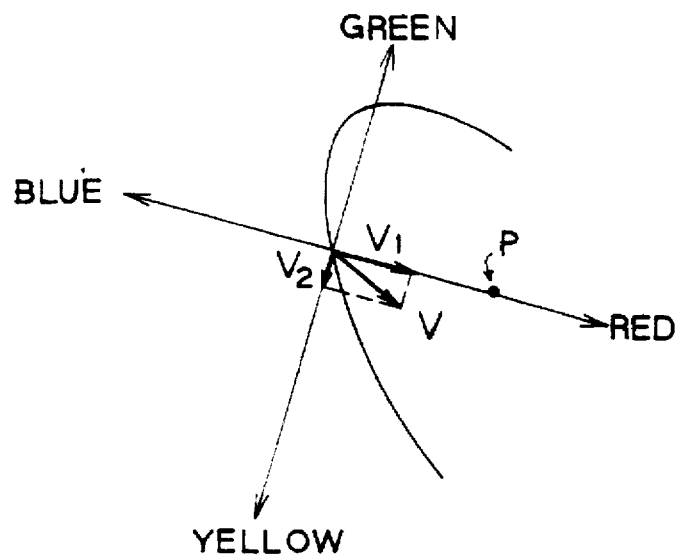
FIG. 33 is another variation showing decomposition of a velocity.

(ii) A second decomposition way shown in FIG. 33 is to decompose an absolute velocity V into one component V1 parallel to a straight line connecting the fixed point P (see FIG. 28) with each sampling volume position and the other component V2 perpendicular to the component V1. For the velocity component V1, a contraction direction is positive and the expansion direction negative. For the velocity component V2, the same negative and positive system as (i) is applied.

Figure 34:
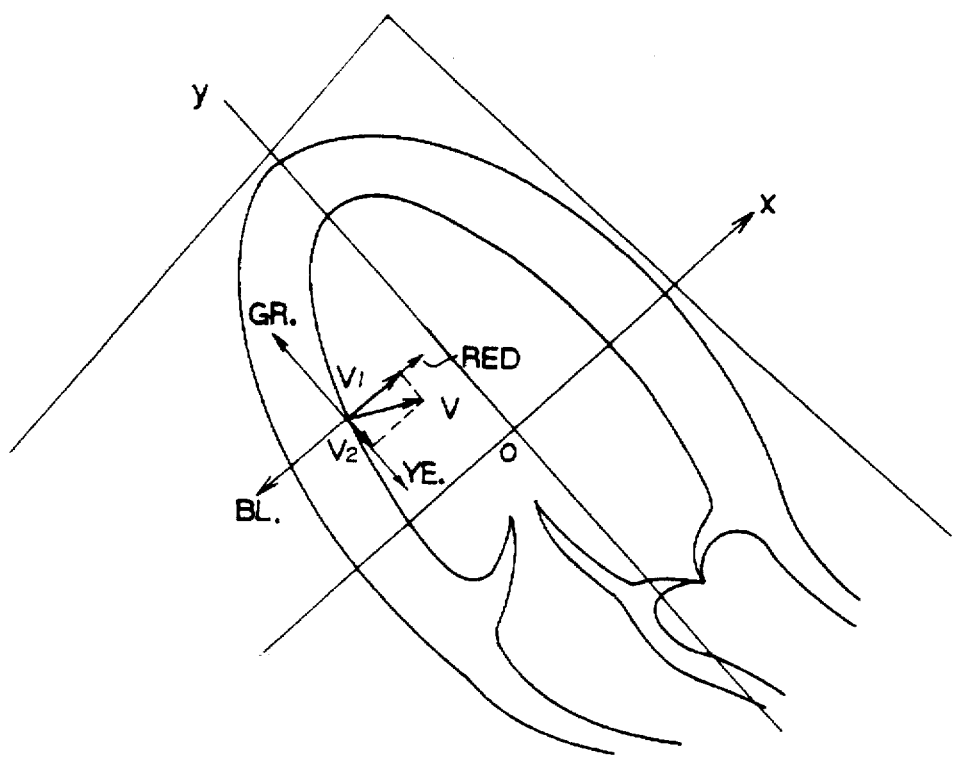
FIG. 34 is still another variation showing decomposition of a velocity.

(iii) A third way is shown in FIG. 34. An orthogonal coordinate system is placed as shown thereon on a ventricle, where an absolute velocity will be separated into components V1 and V2 in x- and y-directions, respectively. The origin of the coordinate system is set at the center or approximate center of a left ventricle.

Figure 35:
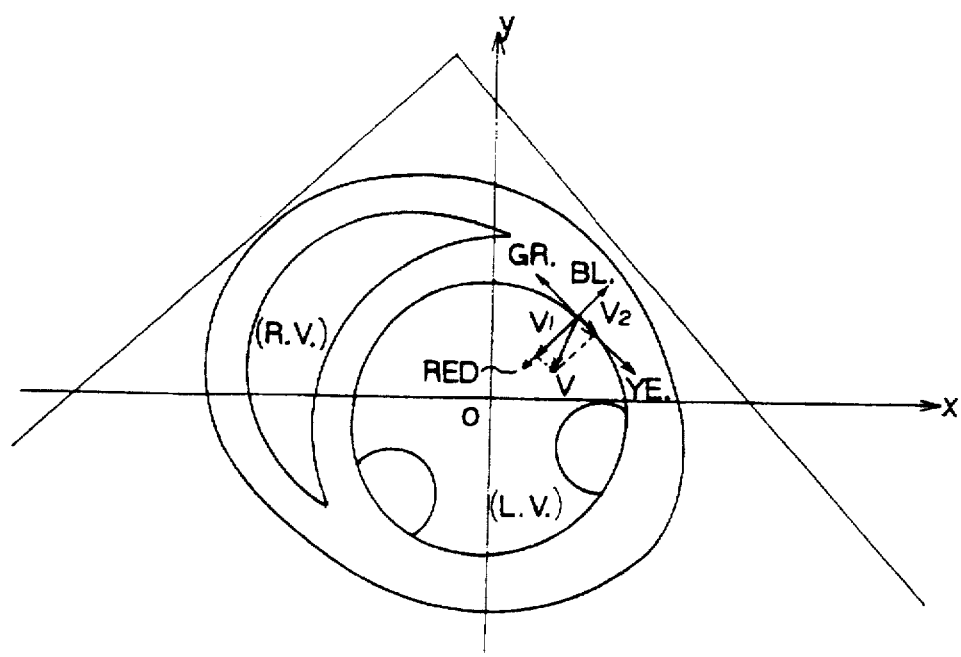
FIG. 35 is still another variation showing decomposition of a velocity.

(iv) A fourth one, illustrated in FIG. 35, adopts a polar coordinate system placed on a left ventricle. An absolute velocity V is decomposed into two components: one component V1 in radial r-direction and the other component V2 in θ-direction.

Figure 36:
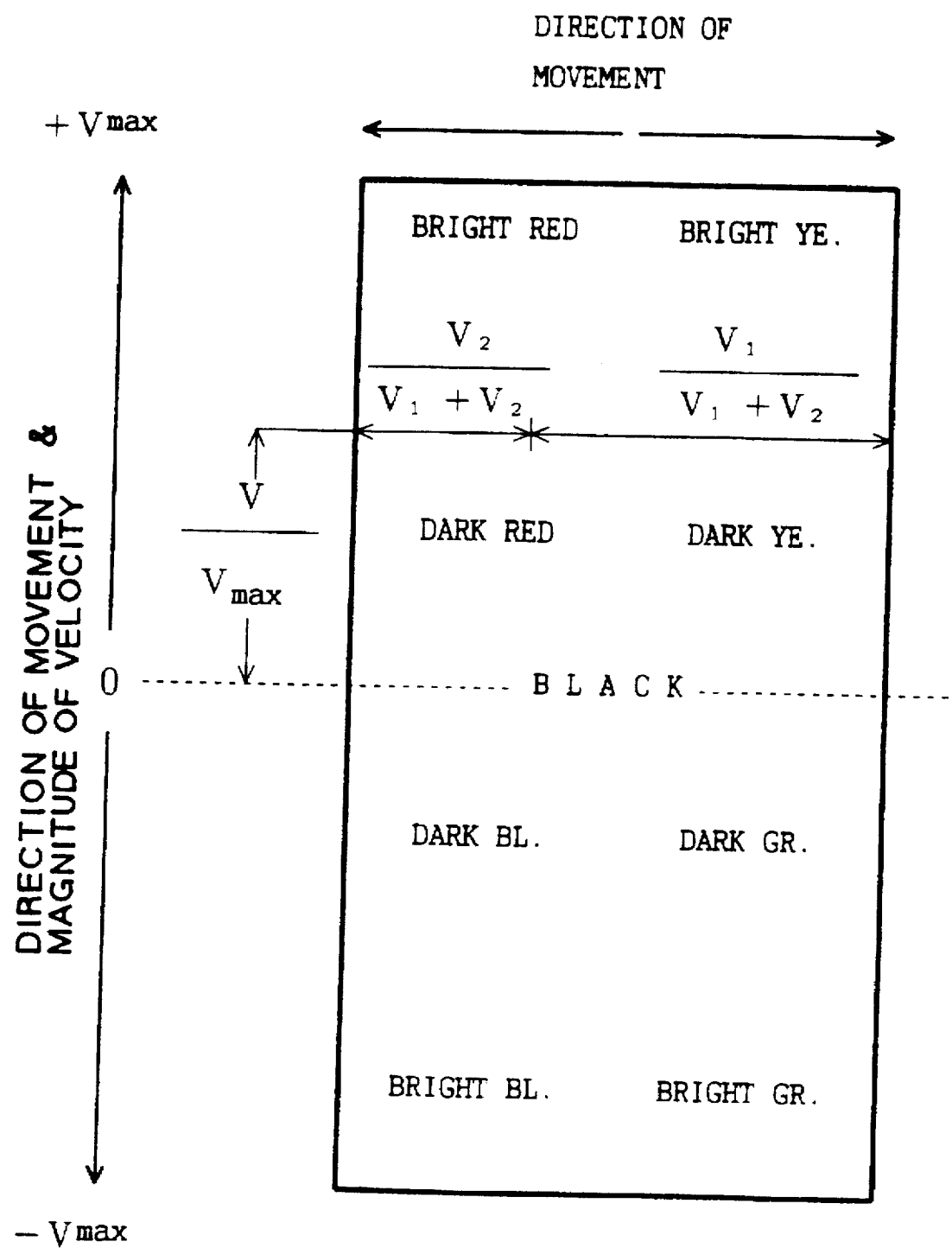
FIG. 36 is a color scale in the fifth embodiment.

In order to decide, colors of the velocity components V1 and V2 thus-decomposed for every sampling volume, the color processing circuit 24b of the DSC 24 has a look up table corresponding to a color scale shown in FIG. 36. In the color scale, the longitudinal axis represents a scale along which, depending on the direction of an absolute velocity V, the contraction of a cardiac muscle is shown in red or red-neighboring color (velocity V is positive) and the expansion is shown in blue or blue-neighboring color (velocity V is negative), with increased brightness as its magnitude increases. When V=0, the display color is black. On one hand, the transverse axis is used for representing a scale along which deviation from given axial lines in contraction and expansion are displayed by yellow and green.

For referring to the above color scale, the decomposition unit 54 will calculate "V/Vmax" to decide that a velocity V now handing should be assigned to the longitudinal upper or lower region in FIG. 36. Then the unit 54 calculates "V2/(V1+V2)" or "V1/(V1+V2)" to decide a position in the transverse axis. These calculations give one point on the color scale and its color data is sent to the color processing circuit 24b of the DSC 24.

Hence, the movement of a cardiac muscle is two-dimensionally displayed, where contraction and expansion motions are represented by colors based on red and blue and where degrees of deviation from given axes in the contraction and expansion motions are represented by combined colors—basic color red taking yellow and basic color blue taking green. For example, in case of an absolute velocity V in vector quantity in FIG. 32, according to one component V1 going toward the inside of a cardiac muscle, red as a basic color is selected, and the basic color red is combined with slight yellow representing the other component V2 in the depth direction. Namely, a part of red taking slight yellow is displayed with a brightness level corresponding to the magnitude of the velocity V. It is possible, therefore, to observe more precisely the condition of movement.

In the present embodiment, a circuit giving contour data to the velocity component decomposition unit 54 is not limited to the contour depiction unit 51, and for instance, instead of it, the B-mode contour depiction unit 53 may be used, which has been shown in FIG. 30.

A sixth embodiment will now be explained according to FIGS. 37 and 38.

The present embodiment relates to display of contour lines of velocity and its automatic trace.

Figure 37:
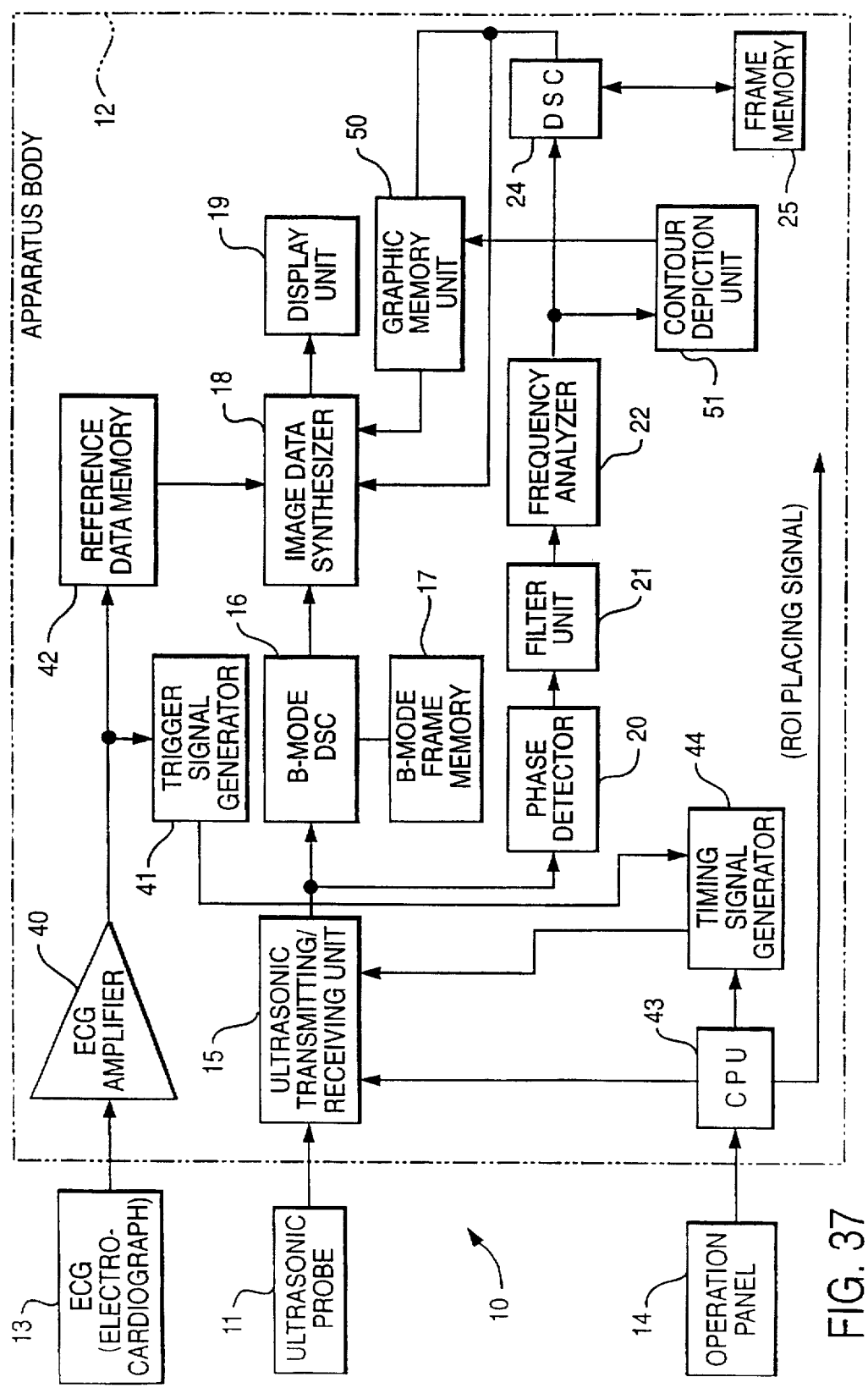
FIG. 37 is a block diagram showing an ultrasonic diagnosis apparatus of a sixth embodiment.

In an apparatus 10 shown in FIG. 37, there is the aforementioned contour depiction unit 51 at the output of the frequency analyzer 22, and the output of the depiction unit 51 will be sent to the image data synthesizer 18 via the graphic memory unit 50.

Movement velocities of a cardiac muscle at each sampling volume are sent to the depiction unit 51. In the unit 51, using the aforementioned method shown in FIGS. 22 to 26, contour data are automatically calculated, the contour data being data in a velocity range whose velocity V is equal to or higher than a minimum velocity Vmin detectable as a movement velocity of a cardiac muscle. The contour data thus-calculated are sent to the graphic memory unit 50, where they are converted into graphic data corresponding to the contour line, the graphic data being sent to the image data synthesizer 18. To the synthesizer 18, color Doppler image data colored in conformity with velocities are supplied from the DSC 24. Therefore, the graphic data of the contour line are superimposed on the color Doppler image data.

Figure 38:
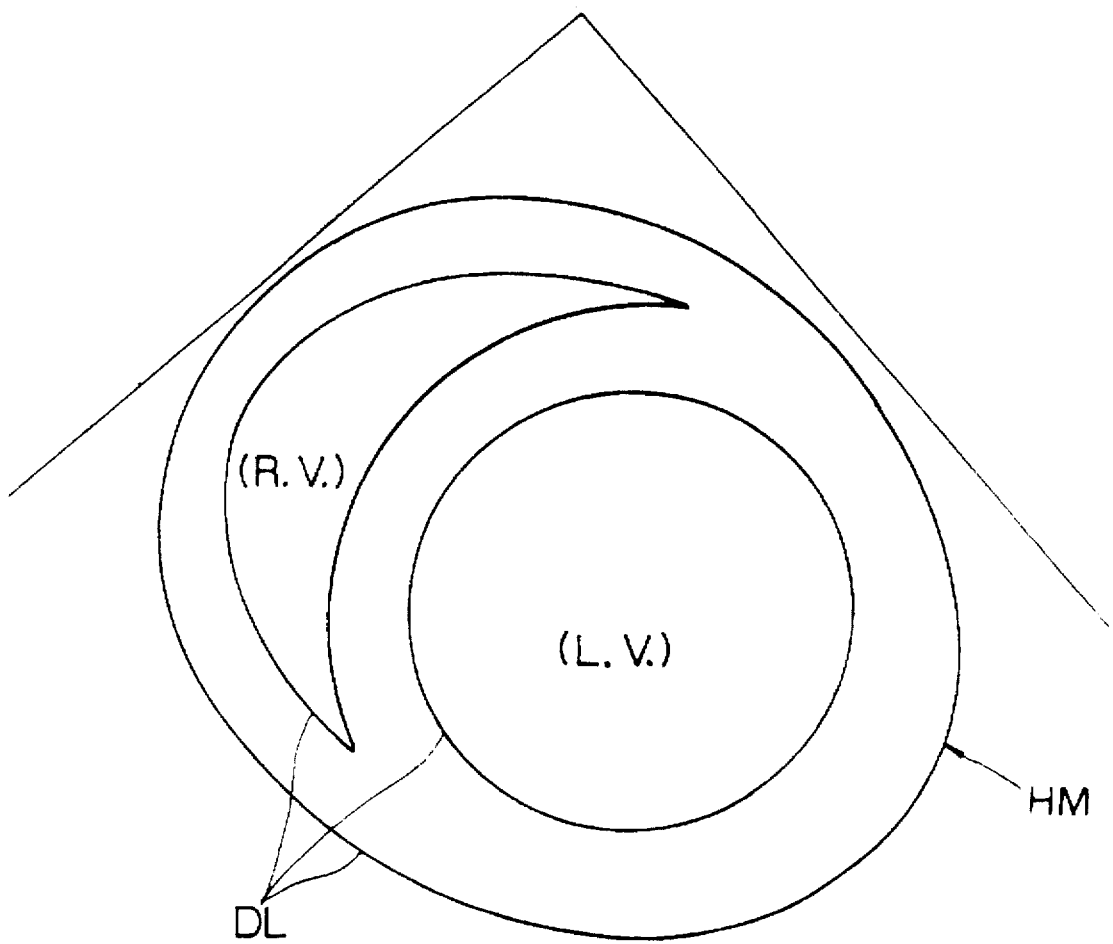
FIG. 38 shows an example of the contour line of a cardiac muscle.

As a result, on the display unit 19, as shown in FIG. 38, a color image of a cardiac muscle HM, whose parameter is the velocity, is displayed such that its contour portion is clearly partitioned by contour lines DL . . . DL. One of the contour lines DL . . . DL is for the endocardium. Because movement velocities at each sampling volume are supplied in real time from the frequency analyzer 22, the contour image changes from moment to moment as the cardiac muscle HM contracts and expands. As a consequence, it is surely possible, at a glance, to understand changes in thickness of a cardiac muscle being examined.

The above embodiments have been directed to the real time display of contour lines. Besides, sine-loop playback display is possible. In addition to freezing a velocity image displayed, it is possible to automatically trace contour parts.

Now, methods of automatic trace of an endocardium, which utilizes the above-mentioned contour display, will be explained. The same hardware construction as that in FIG. 37 is usable.

Figure 39:
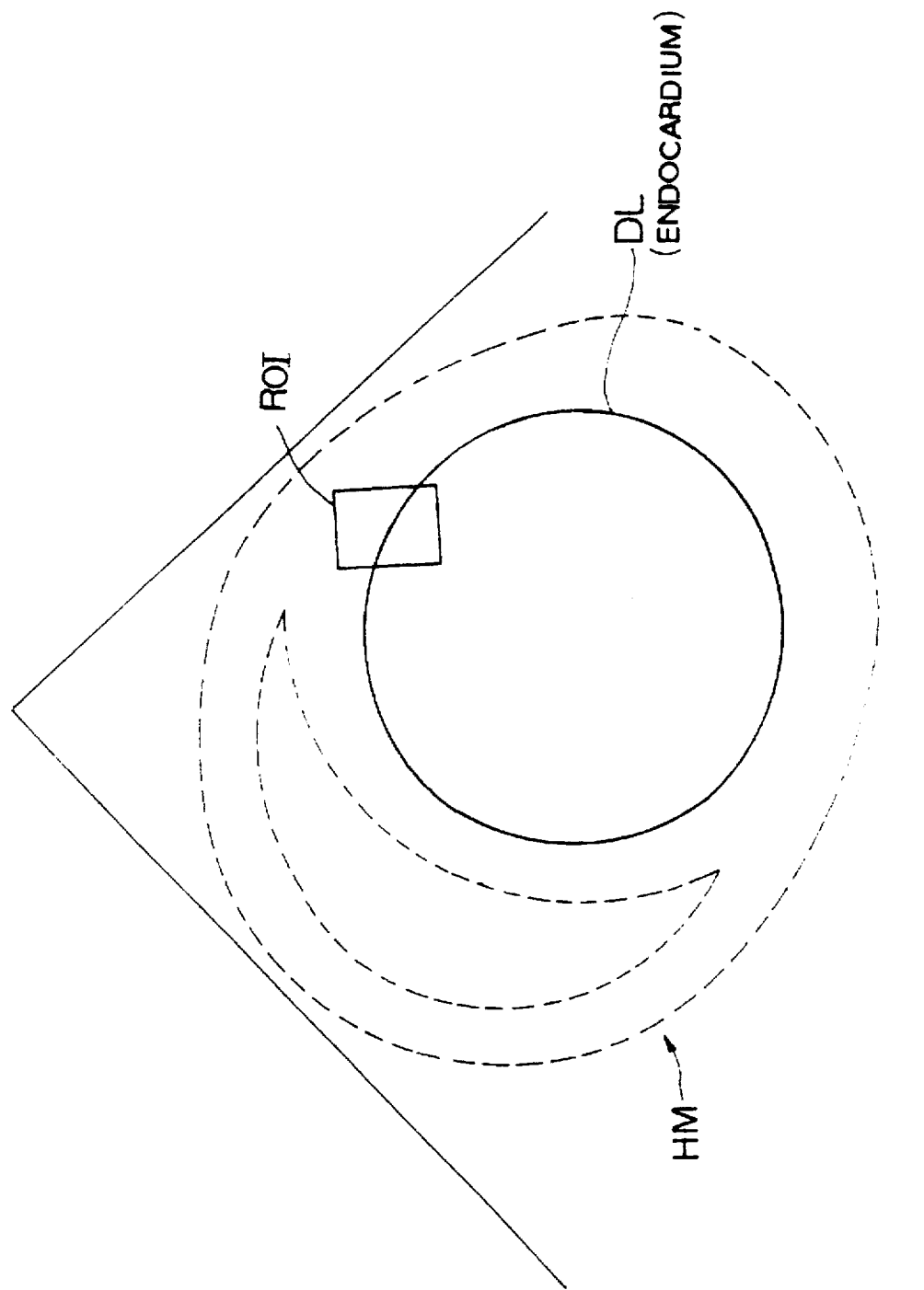
FIG. 39 explains an example for automatic tracing an endocardium.

A first trace method is shown in FIG. 39. In the contour depiction unit 51, after contour data are calculated by the same way mentioned before, a ROI (region of interest) such as a rectangular ROI is placed on the endocardium of a left ventricle to obtain a part of a contour line DL passing through the ROI. Then, the contour line DL is traced to form data representing only the endocardium, sending the formed data to the graphic memory unit 50. This makes it possible to automatically trace only the encodardium, and in case of FIG. 39, a contour line DL expressed by a solid line is depicted on a color velocity image of a cardiac muscle HM. Such processing will be performed by means of the contour depiction unit 51.

Figure 40:
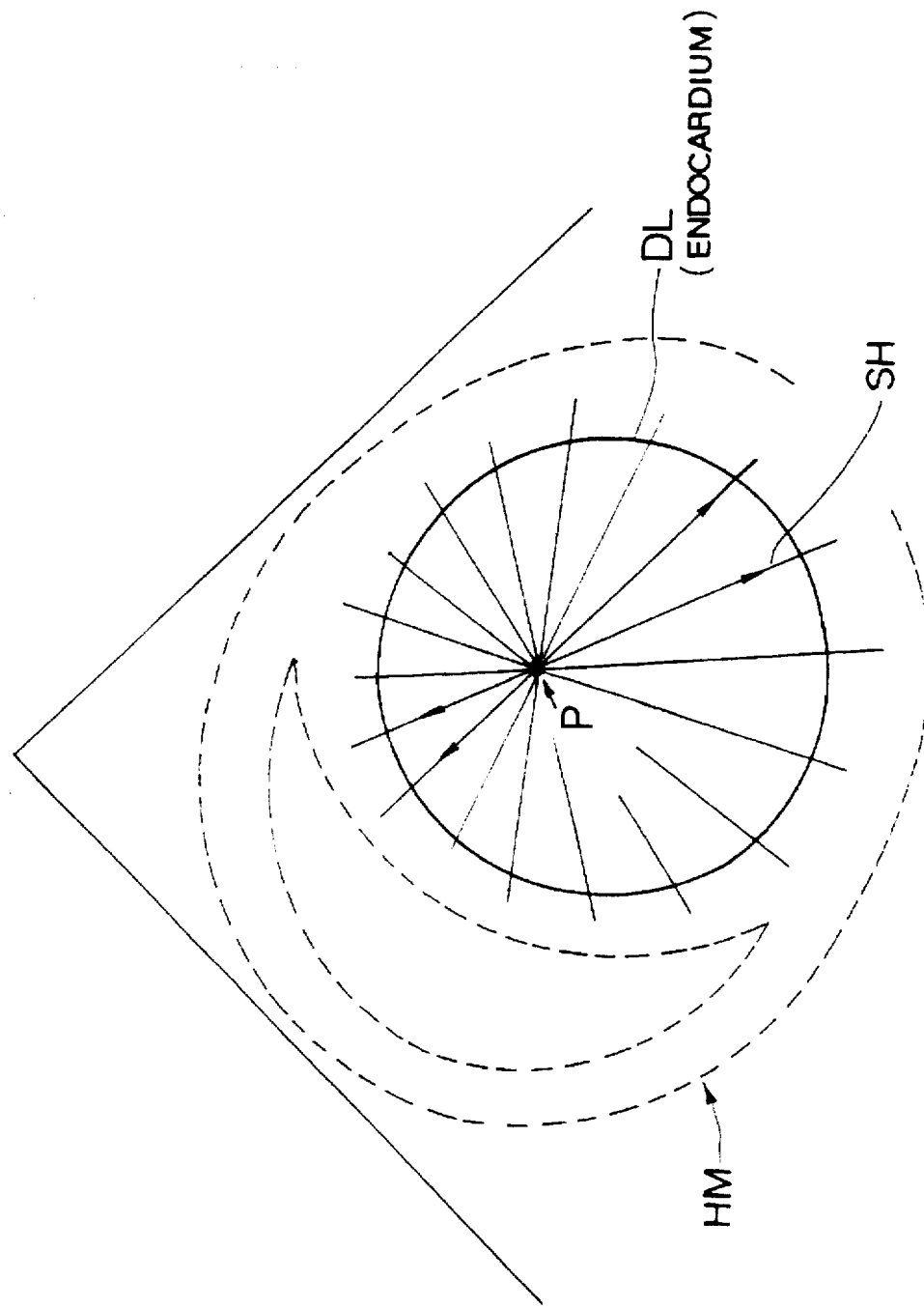
FIG. 40 explains another example for automatic tracing an endocardium.

A second trace method is to utilize a fixed point placed on a left ventricle. After having calculating the contour data of a whole cardiac muscle HM by the same way mentioned already, the contour depiction unit 51 will place a fixed point P on a left ventricle, as shown in FIG. 40. And the unit 51 searches radially data of a contour line from the pixed point P, adopting only a first-encountered data on each of the searching lines as an endocardium data. The data thus-searched are sent to the graphic memory unit 50. Accordingly, it is able to perform an automatic trace of only the endocardium of a left ventricle and for instance, only a contour line DL shown by a solid line in FIG. 40 is depicted on a color Doppler image of a cardiac muscle HM.

The above methods permit the endocardium of a left ventricle to be traced automatically. As a consequence, it is possible to avoid deviation in position of contour lines resulting from specification of gains for received echo signals, which was a problem in conventional techniques, providing an automatic trace of an endocardium with remarkably improved accuracy and duplicability.

It is true that an epicardium is automatically traced as well.

Applying the above automatic trace to measurement of values, such as cross-sectional areas and volumes of a left ventricle, makes it possible to evaluate functions of the left ventricle. But, since the movement velocities at the end-systole and end-diastole are almost zero, the automatic trace is practically difficult in those ends. A countermeasure against the drawback is provided as follows.

In the first place, the above drawback will be explained in detail. FIG. 41 represents a detected velocity Vm against an ultrasonic frame number m: a transverse axis shows the ultrasonic frame number m (m=1, 2, . . . ) every sector scan and a londitudinal axis shows the detected velocity Vm of each of the ultrasonic frames at a certain sampling volume. In case that the detected velocity Vm is periodically changed such as shown therein, velocities Vm . . . Vm falling into a range of −Vmin<Vm<+Vmin (Vmin: a minimum velocity detectable by an apparatus) will not be detected, thus Vm=0 in such a case. For example, in FIG. 41, Vm=0 at the frame number m=1, 5, 6, 10 and 11, and it is impossible to detect edges from a color Doppler image of movement. In other words, the edges are indistinguishable from the other parts excluding a cardiac muscle, where velocities are also zero.

In order to remove the drawback, using algorithm shown in FIG. 42, the contour depiction unit 51 will convert the detected velocities Vm . . . Vm at each sampling volume position into other velocities V'm . . . V'm for detecting edges.

Figure 43:
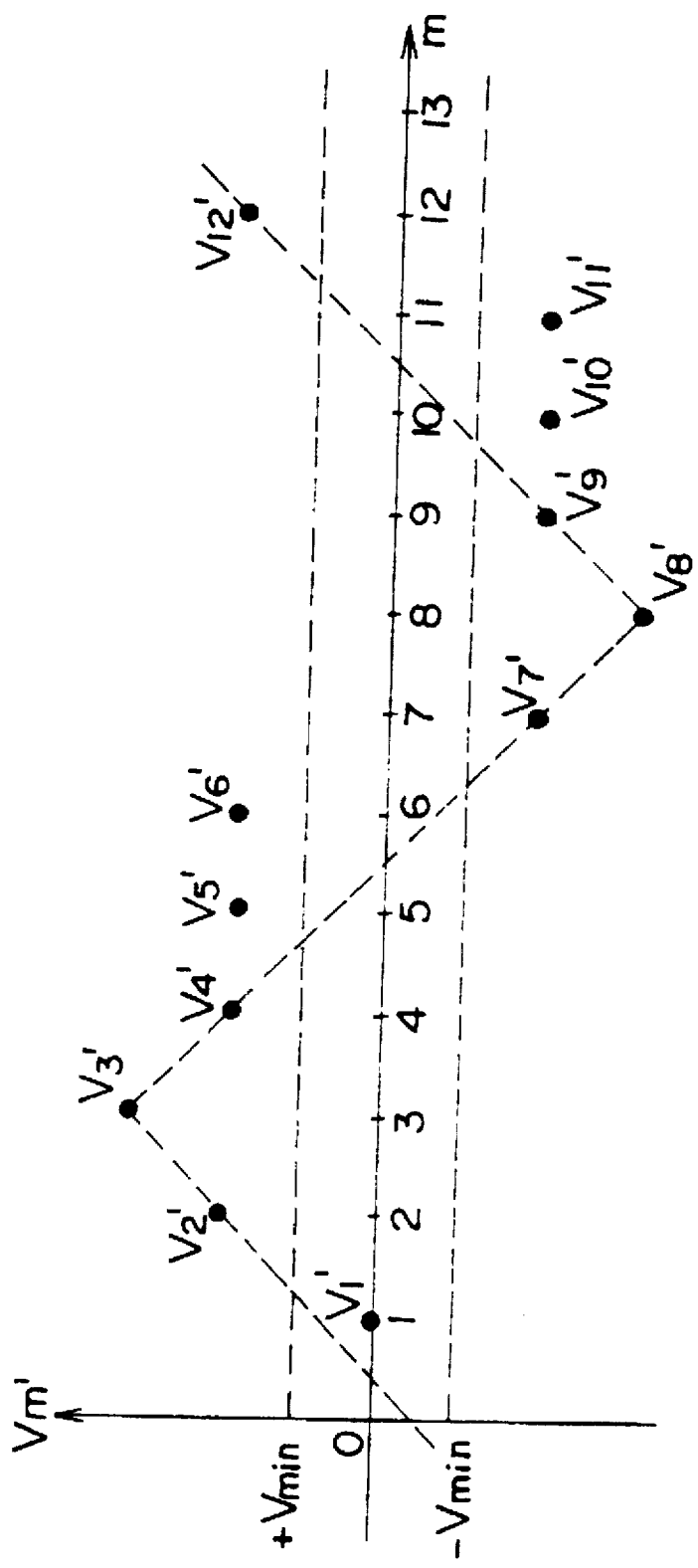
FIG. 43 explains the improvement for detection of the velocity in automatic trace.

At Step ST1 in FIG. 42, the ultrasonic frame number is set to be m=1 as an initial value. Then at Step ST2, it is judged whether the absolute value of a detected velocity V1 is less than a given value Vmin which is either a minimum velocity detectable by an apparatus or a threshold level among a detectable range of velocities. When NO at Step ST2, the detected velocity V1 is replaced by a converted velocity V'1 (i.e. V'1=V1) at Step ST3. But when YES thereat, V'1=0 is set at Step ST4. After Steps ST3 and ST4, the frame number m is incremented (m=m+1) at Step ST5. Then at Step ST6, it is judged if the absolute value of a detected velocity Vm in the incremented frame is less than the given value Vmin. When NO at this judgement, V'm=Vm at Step ST7. Contrary, YES at that judgement, V'm at present frame is set to be V'm=V'm−1 (equal to or larger than Vmin), which is a converted velocity at the last frame of the frame number m−1. Steps ST5 to ST8 are repeated according to the incremented frame number m. In this way, in case that the absolute values of detected velocities Vm . . . Vm are smaller than a given value Vmin, converted velocities V'm−1 of one. frame before are artificially specified. As a result, the velocity curve shown in FIG. 41 is converted into that in FIG. 43, thus excluding conditions of Vm=0. By the way, in the converted velocity points of FIG. 43, it happened that when m=1, V'1=0. However, as it is adequate to consider that the frame number m continues to infinity unless the number is reset, there no problem for V'1=0.

Accordingly, the above conversion of velocity enables more stable and precise analysis of a left ventical.

It may be possible for an endocardium to be colored according to the magnitudes of movement velocities, thus displaying only the velocities of the endocardium.

A seventh embodiment will now be explained according to FIG. 44. The present embodiment is to calculate acceleration of movement of a cardiac muscle.

Figure 44:
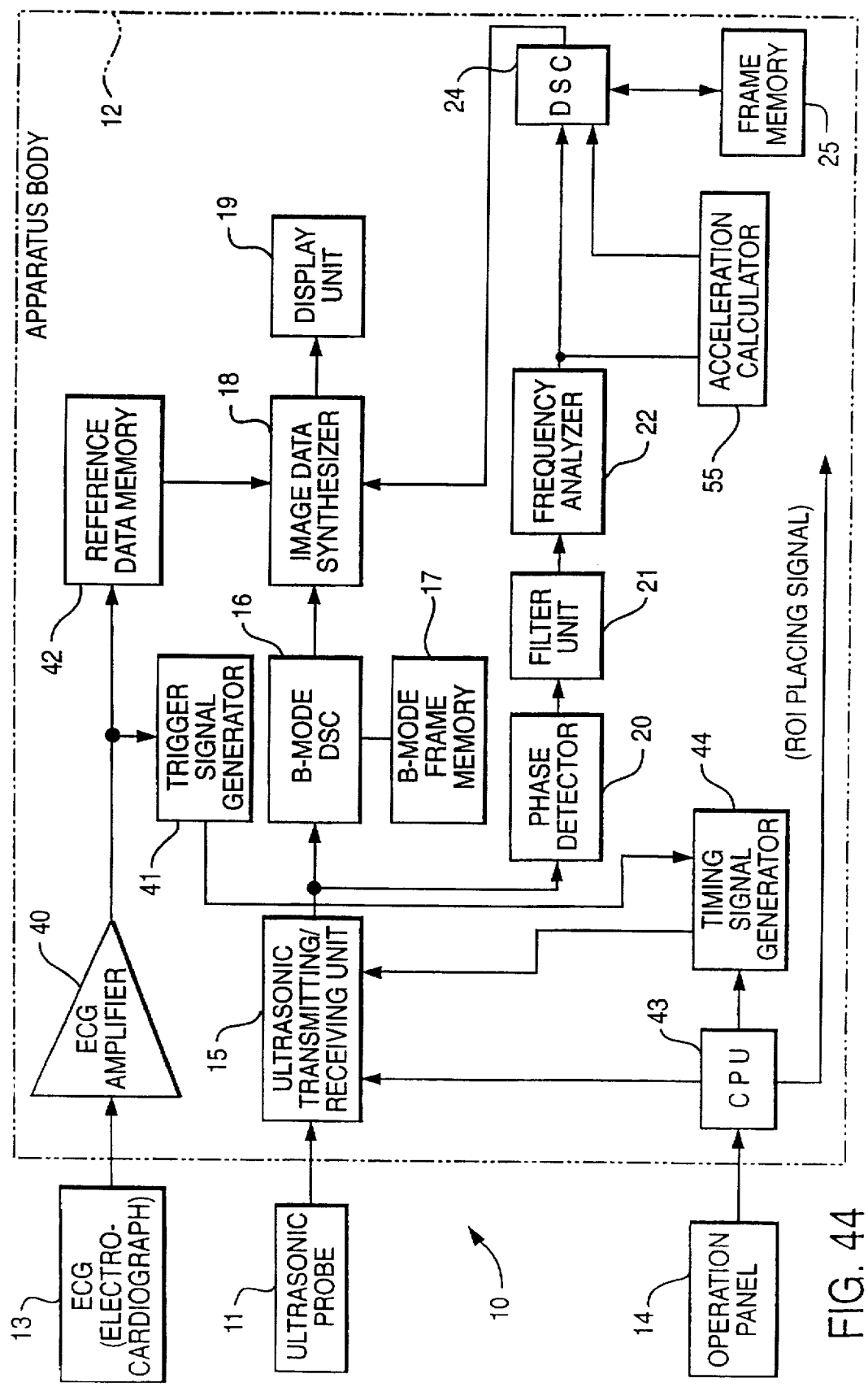
FIG. 44 is a block diagram showing an ultrasonic diagnosis apparatus of a seventh embodiment.

In an apparatus 10 shown in FIG. 44, provided are the DSC 24 and an acceleration calculator 55 to both of which the output of the frequency analyzer 22 is connected. The acceleration calculator 55 will calculate movement acceleration of a cardiac muscle, which is sent to the DSC 24.

In the acceleration calculator 55, using values of motion velocity values at each sampling volume supplied from the frequency analyzer 22, their acceleration values are calculated. The practical calculation is as follows. Taking a look at a certain sampling volume in a scan region and supposing that detected velocity values are Vn−1 for the "n−1"-th frame and Vn for the n-th frame, an acceleration value of a cardiac muscle at the sampling volume position is approximately given by $$dV/dt = (Vn - Vn-1)/T,$$

where T is a scan period between ultrasonic frames. This calculation will be carried out every sampling volume.

The acceleration data at each sampling position thus-calculated are processed for coloring in the DSC 24. The display of acceleration is also classified into two ways: one way displays only the magnitude (absolute value) of acceleration and the other displays both of the magnitude of acceleration and the direction of movement. The practical methods can be accomplished by replacing the display items of velocity described in the foregoing embodiments with those of acceleration.

In this embodiment, further, a construction is adoptable that the acceleration and velocity calculators are arranged in parallel at the output side of the frequency analyzer 23.

An eighth embodiment will now be explained according to FIGS. 45 to 49. The present embodiment is to calculate timings of movement of a cardiac muscle.

Figure 45:
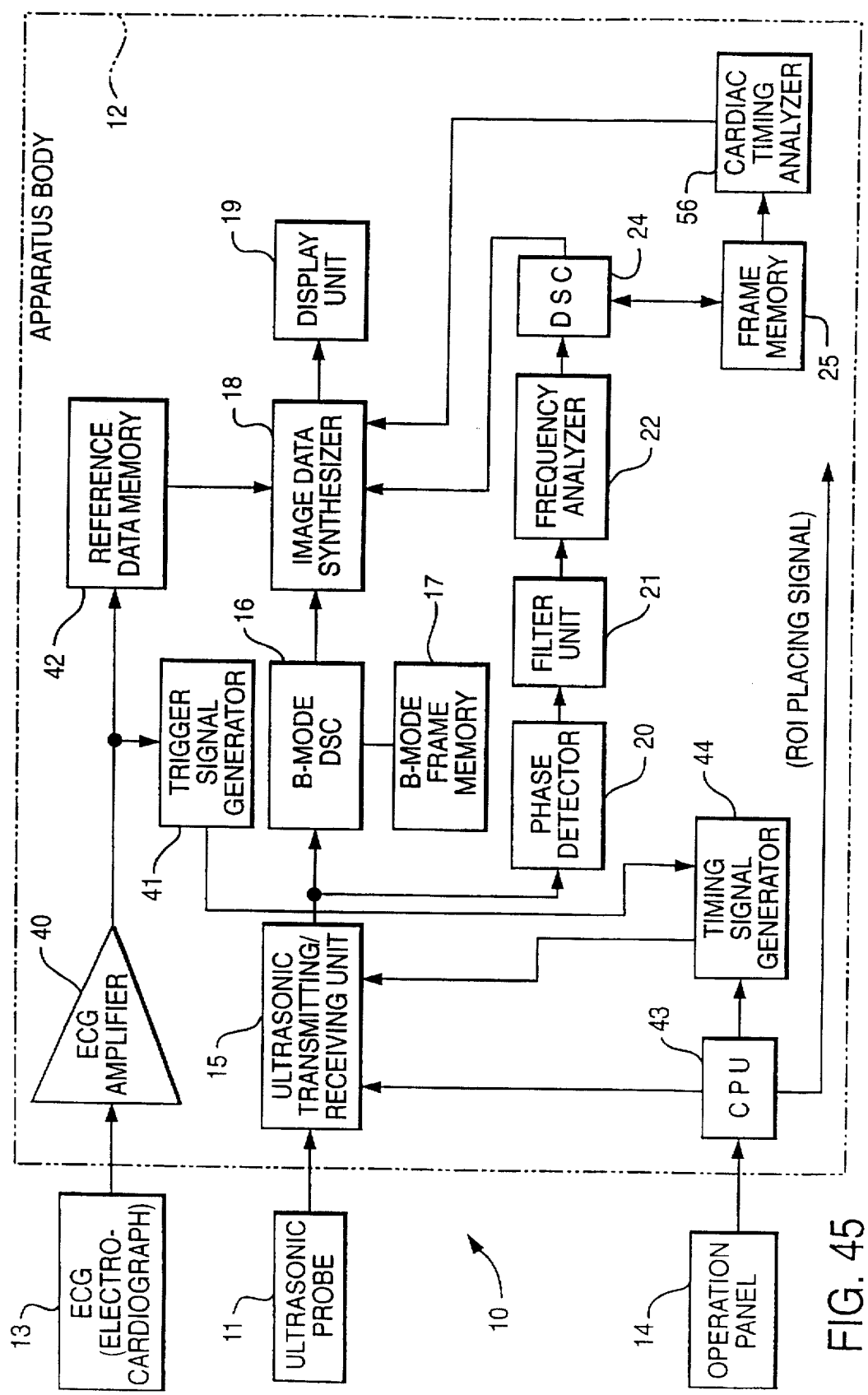
FIG. 45 is a block diagram showing an ultrasonic diagnosis apparatus of an eighth embodiment.

In an apparatus 10 shown in FIG. 45, there provided is a cardiac timing analyzer 56 arranged at the output side of the frame memory 25, the analyzed result by the cardiac timing analyzer 56 being sent to the image data synthesizer 18.

The cardiac timing analyzer 56, which has a CPU operating according to prestored software, will read one heart beat data of movement velocities from the frame memory 25 and analyze timing phases in velocities of movement. In detail, a basic event such as an R-wave on an electrocardiogram is set as time=0, and on the basis of changes in movement velocities of a cardiac muscle during a cardiac cycle, times when the velocity reaches a certain value and its maximum value are determined in systole and diastole periods.

In the present construction, if the acceleration calculator 55 described in FIG. 44 is arranged, objects for analyzing timings of movement may include times when the acceleration reaches a certain value and its maximum value in systole and diastole periods.

Figure 46:
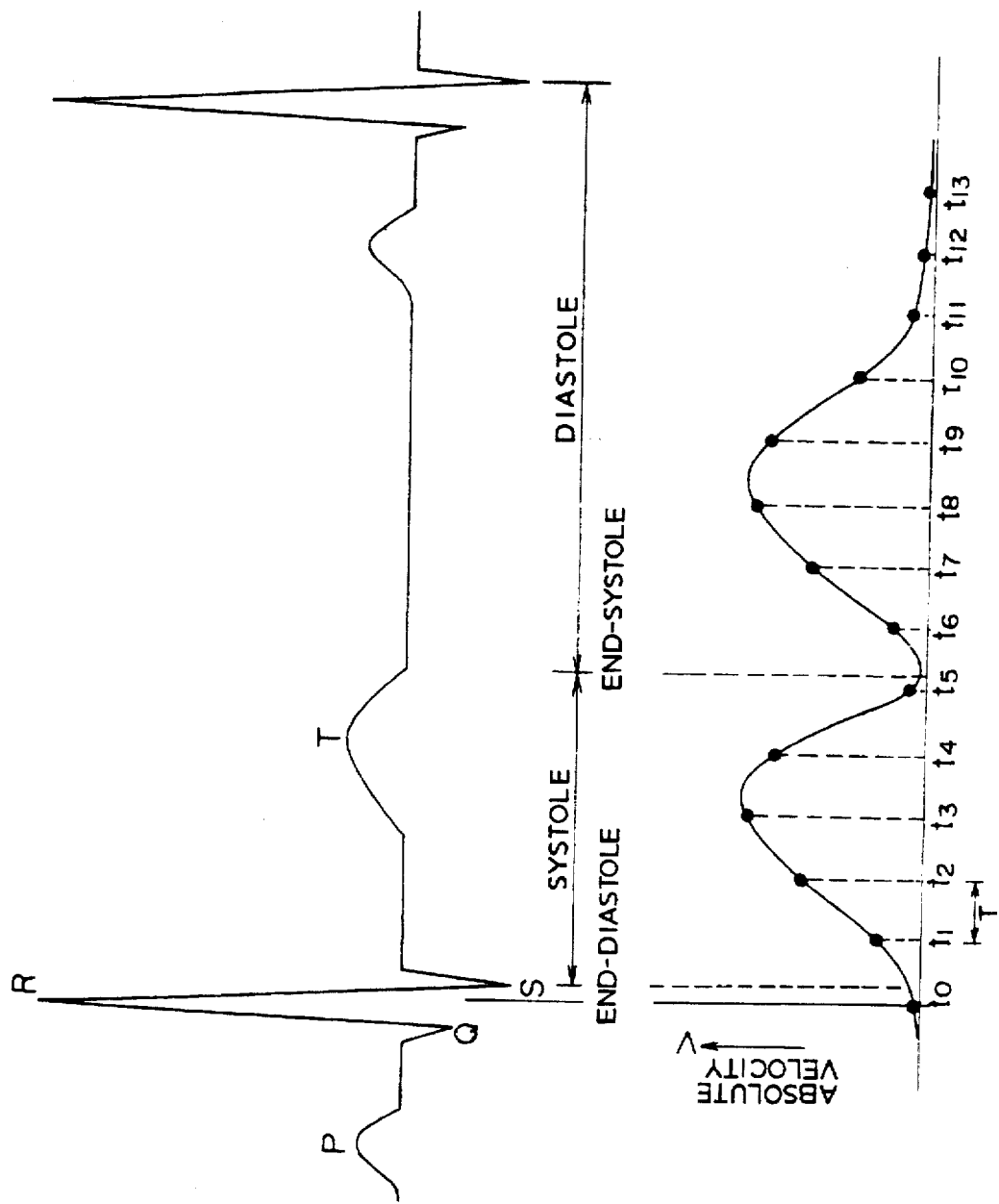
FIG. 46 is a graph showing change in absolute value of movement velocity of a cardiac muscle.
Figure 47:
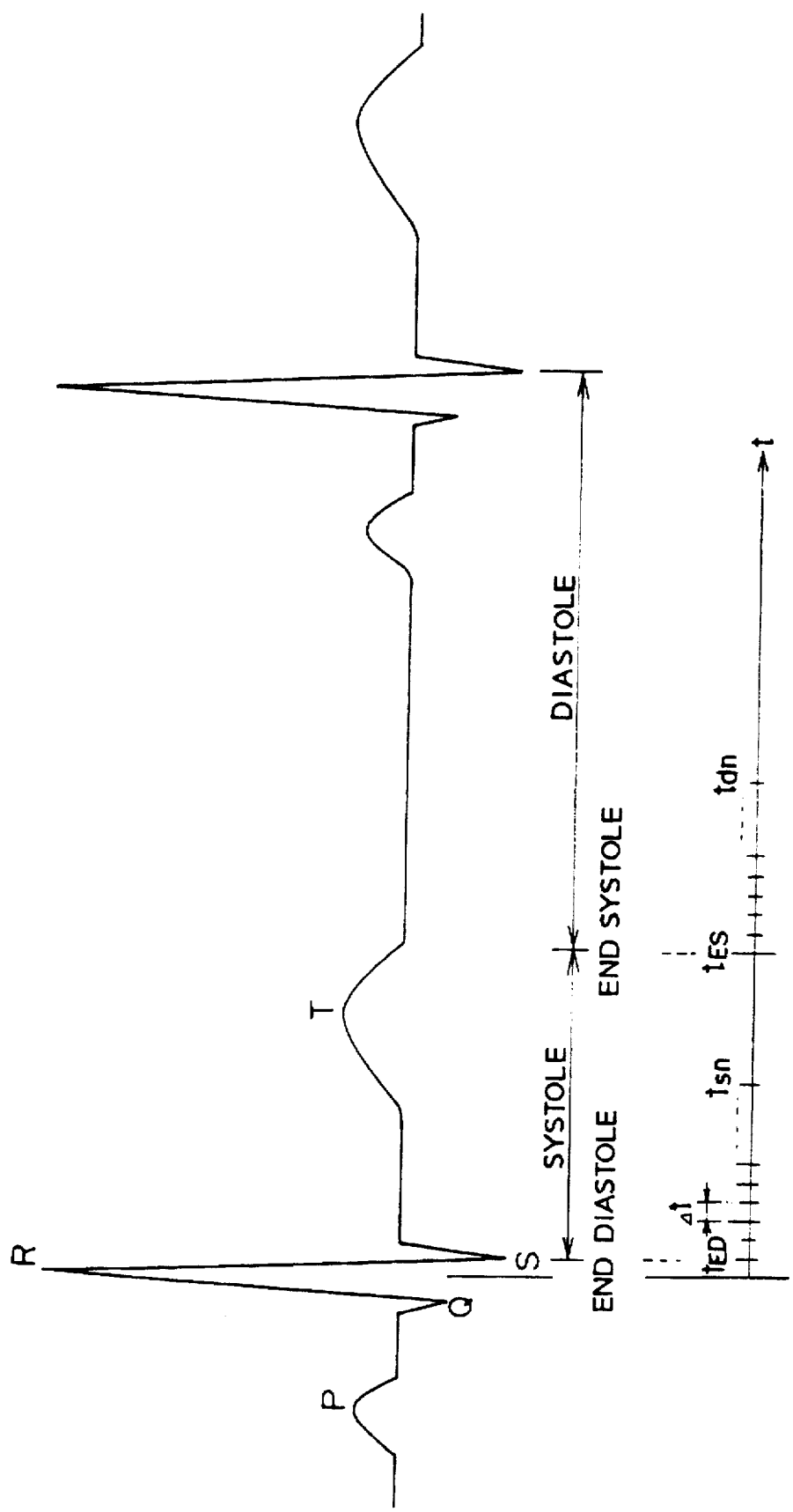
FIG. 47 is a graph showing analysis in movement timings of a cardiac muscle.

FIG. 46 represents changes in absolute values of movement velocity of a cardiac muscle at its certain sampling volume. As shown therein, a time when a given basic event in a cardiac cycle (R-wave) occurs is set to be zero and the velocity varies according to a systole and diastole periods. From the appearance time (t=0) of the R-wave, the timings analyzer 56 calculates systole-period time phases $t_{sn}$ and distole-period timings $t_{dn}$ as follows (refer to FIG. 47):

$$t_{sn} = n \cdot \Delta t \text{ or } t_{sn} = t_{ED} + n \cdot \Delta t,$$

where n=0, 1, 2, . . . , $t_{ED}$ is a time of end-diastole and Δ t is a divided time. Also, $$t_{dn} = n \cdot \Delta t \text{ or } t_{dn} = t_{ES} + n \cdot \Delta t$$

where n=0, 1, 2, . . . , $t_{ES}$ is a time of end-systole; and Δ t is a divided time. The above calculation for $t_{sn}$ and $t_{dn}$ will be done every sampling volume.

Figure 48:
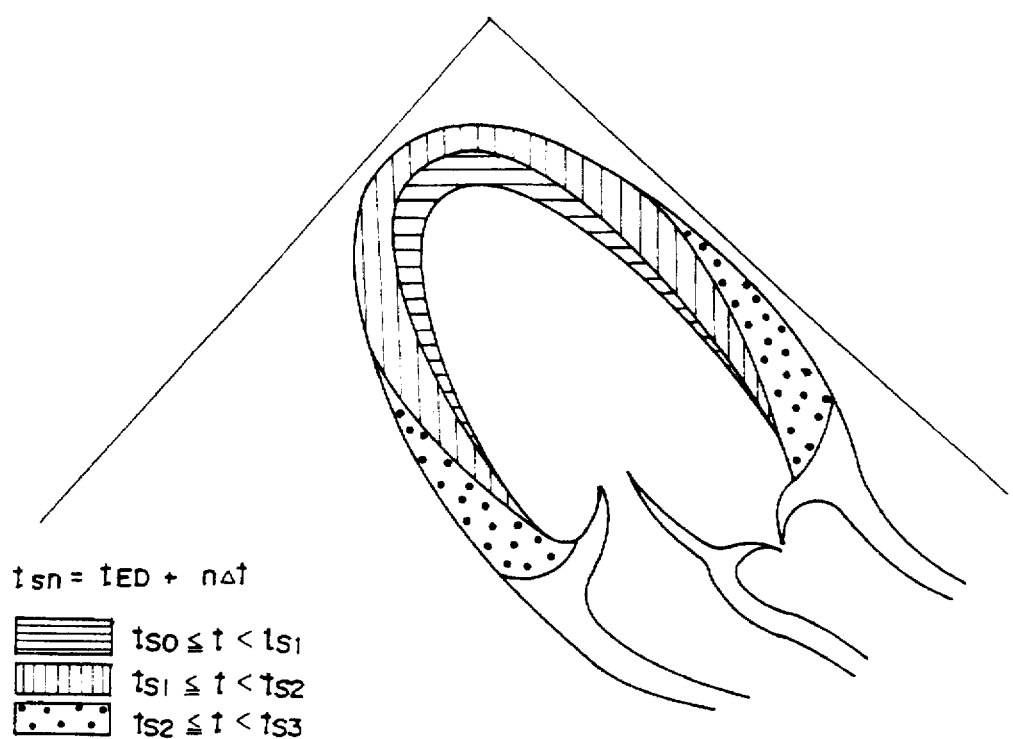
FIG. 48 is an image showing analysis in movement timings of a cardiac muscle.
Figure 49:
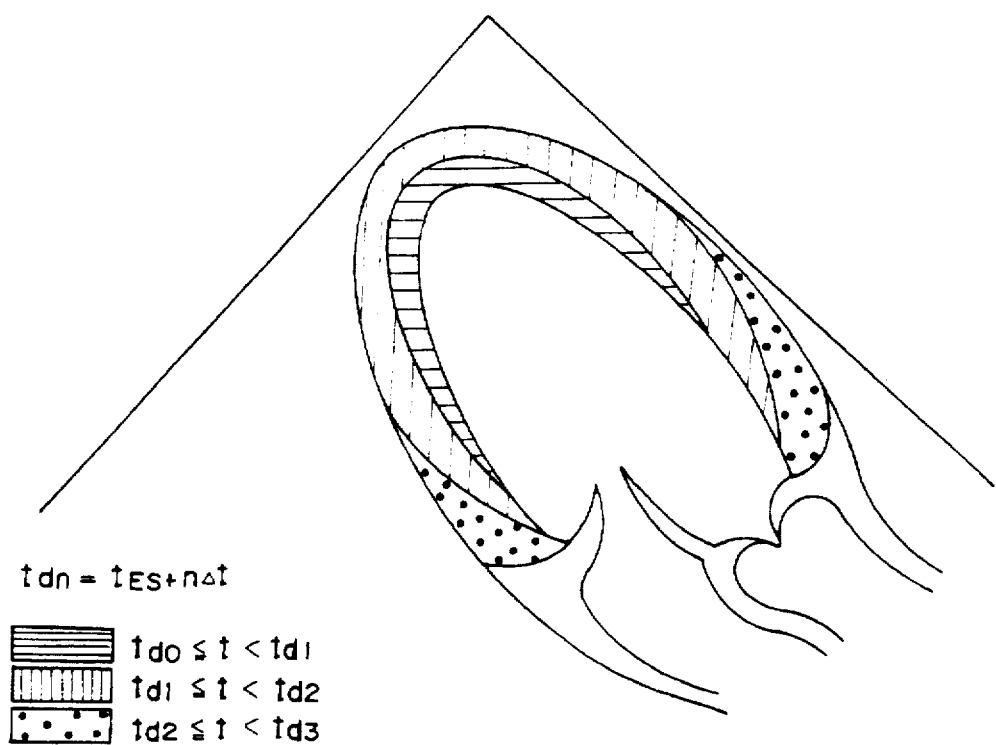
FIG. 49 is another image showing analysis in movement timings of a cardiac muscle.

And the analyzer 56 calculates, using the calculated data of $t_{sn}$ and $t_{dn}$, the differences in time when velocity (or acceleration) reaches a certain value (or its maximum value) every sampling volume, and produces data of color or brightness corresponding to the calculated time differences, the data being sent to the image data synthesizer 18. This gives two-dimensional images of the time difference shown in FIGS. 48 and 49, for instance. In FIG. 48, the differences in time when the velocities at each sampling volume position in a systole period reach a given value are shown in a manner such that they are classified into three categories divided by threshold values of $t_{s0}$, $t_{s1}$, $t_{s2}$, and $t_{s3}$ and are colored or brightened correspondingly to those categories. Also in FIG. 49, the time differences of these in a diastole period are shown in the same way.

Further, on the basis of the above analyzed results, one of the following items (i) to (v) will be highlighted with different color or brightness from other parts:

(i) a region corresponding to a specified time difference, (ii) a region whose contraction starts at the earliest time, (iii) a region whose contraction starts at the latest time, (iv) a region whose expansion starts at the earliest time, and (v) a region whose expansion starts at the latest time.

The highlighting will be demanded from the color processing circuit of the DSC 24 using a lookup table prestored therein.

This provides various information with respect to timings of movement at local positions of a cardiac muscle.

The present embodiment has been explained such that the the movement timings are analyzed every heart beat. Reading and analyzing the velocity data of a plurality of heart beats from the frame memory 25 permits the cardiac timing analyzer 56 to calculate the mean values of the above results over a plurality of heart beats, thus providing two-dimensional images of time differences based on the mean values. Still, data of time differences between the appearance time of an event in a previous cardiac cycle and that in the present cardiac cycle are also possible to be two-dimensionally displayed. Still further, normal heart beats and abnormal heart beats such as cataplectic cardiac dysrhythemia are distinguishable one from the other, and in regard to the above-mentioned analyzing items, two images in those heart beat conditions can be displayed at the same time on the same screen.

Now, an influence on analysis of movement timings caused by differences in ultrasonic beam scan directions and a countermeasure against it will be discussed.

In an ultrasonic diagnosis apparatus using an electrical sector method, it is common to repeat scans from the right to left or from the left to right in one-way direction as shown in FIG. 50A or 50B, so that one tomographic image is formed. This scan method can also be applied to the present invention.

However, when the above scan method is used for determining the appearance times of events in a cardiac cycle, it is necessary to take into account the influence by difference in scan directions.

Velocity data obtained at each sampling volume are discrete in time and a time $t_{m,n}$ at which each velocity data is collected at each sampling volume position on each scan line is given by, as the appearance time of the R-wave is zero, $$t_{m,n} = (m-1+n/N)T \quad (5),$$

where m: ultrasonic frame number (m=1, 2, 3, . . . j  n: scanning line number (n=1, 2, 3, . . . j  N: total number of the scanning lines in one frame; and T: scan period between frames.

As apparent from the expression (5), between the two times at which echo data are each collected on both the rightmost and leftmost scanning lines in one frame; there is a time difference $$t_{m,N} - t_{m,1} = (1-1/N)T$$

where the right side is approximately equal to T. Accordingly, $$t_{m,N} - t_{m,1} = T \quad (6).$$

To handle all data obtained for the time difference as data at a time mT, it is required that the scan period T be fully shorter than time resolution necessary to analyze movement timings of a cardiac muscle at its local points; otherwise a problem will occur. The above time difference also arises between times at which data are collected on both the scanning lines at the rightmost and leftmost sides, respectively, with the scanning line moved from the right to left and from the left to right.

To reduce the time difference, there are two ways: one way is that the scan period T itself is reduced, the other is that the time difference is corrected.

For the former, there are several ways which have been known and adopted in a conventionally-used ultrasonic tomographic diagnosis apparatus and Doppler diagnosis apparatus, which are also applicable to the present invention. Accordingly, the latter will be discussed below.

(i) In case that a time when the velocity (or acceleration) reaches a given value is determined. Suppose that the given value is $V_{TH}$ and velocities at a sampling volume on the n-th scanning line in the m-th frame and the "m−1"-th frame are $V_{m,n}$ and $V_{m+1,n}$, respectively. When the velocities $V_{m,n}$ and $V_{m+1,n}$ first accomplish, from a time at systole start or diastole start, a relation of $$V_{m,n} \leq V_{TH} \leq V_{m+1,n},$$

a time $t_{TH,n}$ when the velocity reaches $V_{TH}$ is given by linear approximation as follows:

$$t_{TH,n} = t_{m,n} + \{(V_{TH}-V_{m,n})/(V_{m+1,n}-V_{m,n})\} \cdot (t_{m+1,n}-t_{m,n})$$

Inserting the expression (5) into the above gives $$t_{TH,n} = \{(m-1+n/N)+(V_{TH}-V_{m,n})/(V_{m+1,n}-V_{m,n})\} \cdot T \quad (7)$$

Here, it is assumed that the magnitude of movement velocities of a cardiac muscle increase in a monotone fashion in the systole start or diastole start and velocity changes in a rather short range of time T is possible to be linearly approximated. The above correction will be carried out by the cardiac timing analyzer 56.

(ii) In case that a time when the velocity (or acceleration) reaches its maximum value is determined.

It is likely that the movement velocity of a cardiac muscle in one cardiac cycle will quantitatively be represented as in FIG. 46. In the figure, when the velocity curve is sampled at a period T (i.e. scan period between ultrasonic frames) to calculate the times when the velocity reaches its maximum, the times become $t_3$ (=3T) in the systole period and $t_8$ (=8T) in the diastole period. However, as understood even from the curve, the true maximum times does not lie at the times $t_3$ and $t_8$, but lie between $t_3$ and $t_4$ in the systole period and between $t_8$ and $t_9$ in the diastole period, respectively. In other words, as time resolution is T in figure 46 and a time error is within ±T, this leads to much trouble when the period is long.

Thus, a way to reduce the time-detection errors will be proposed. This way is such that, if scanning is repeated every heart beat on the basis of R-waves, the start of the timing measured from points of R-waves is step by step deviated every heart beat to sample velocity data over several heart beats, and times at the maximum velocities are determined every systole/diastole period.

One practical example is shown in FIGS. 51A to 51D. This shows that the start timing is deviated every T/4 and the sampling is done over four heart beats. Namely, if the deviation value of each time is Δt, each start timing is Δt=0, T/4, 2T/4, 3T/4 for sampling the velocity data. As a result, times at the maximum velocities are $t_{1,3}$ (=3×(¼)×T) or $t_{2,3}$ (=3×(¾)×T) in the systole period and $t_{2,8}$ (=-(¾)×T) in the diastole period, and an improved time resolution and time error are T/4 and ±T/4, respectively.

The above improved way is on the assumption that a velocity curve has very little change every heart beat. The trigger signal generator 41 is in charge of such deviation control of the start timing.

Further, in the above improved way, to simplify the explanation, the time difference between scanning lines in one frame, which has been mentioned, was not taken into account. If such time difference being taken into consideration, theoretical calculation of times at maximum velocities will be as follows:

$$t_{B,m,n} = \{m-1+n/N+(B-1)/L\}T \qquad (8)$$

wherein L: the number of heart beats (L=4 in FIG. 51), and B: a heart beat number (=1, 2, 3, ... L)

A ninth embodiment will now be explained according to FIGS. 52 and 53. The present embodiment is to perform phase analysis of movement velocities of a cardiac muscle.

Figure 52:
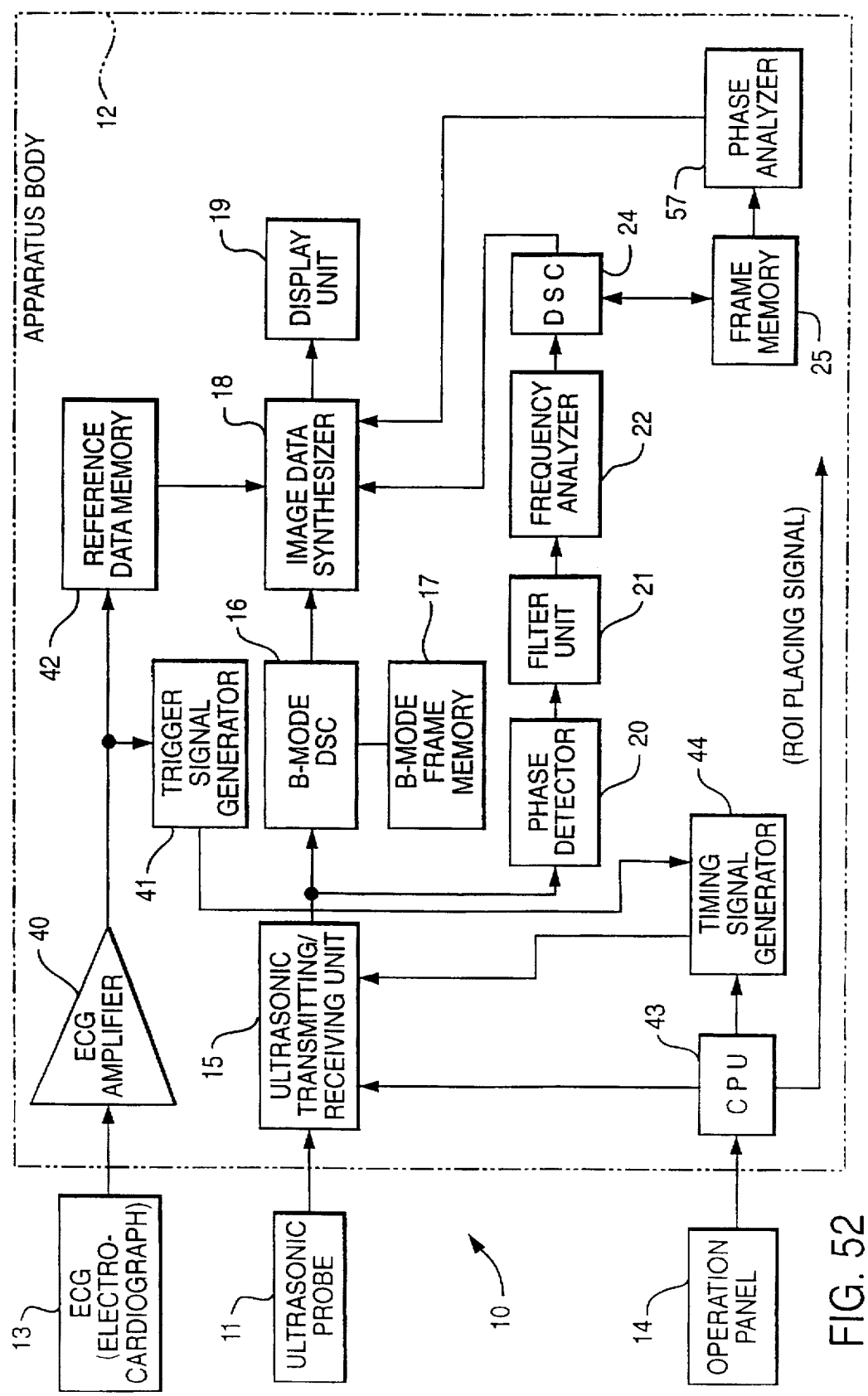
FIG. 52 is a block diagram showing an ultrasonic diagnosis apparatus of a ninth embodiment.

In an apparatus 10 in FIG. 52, there provided is a velocity phase analyzer 57 arranged at the output of the frame memory 25, the analysis results from the analyzer 57 being sent to the image data synthesizer 18.

The velocity phase analyzer 57, which contains a computer in which a predetermined program is prestored, reads the movement velocity data for one heart beat from the frame memory 25, analyzes phases of a movement velocity by means of the following procedure, and calculates the phase or amplitude of the n-th frequency of the velocity.

The procedure of phase analysis is as follows.

Figure 53:
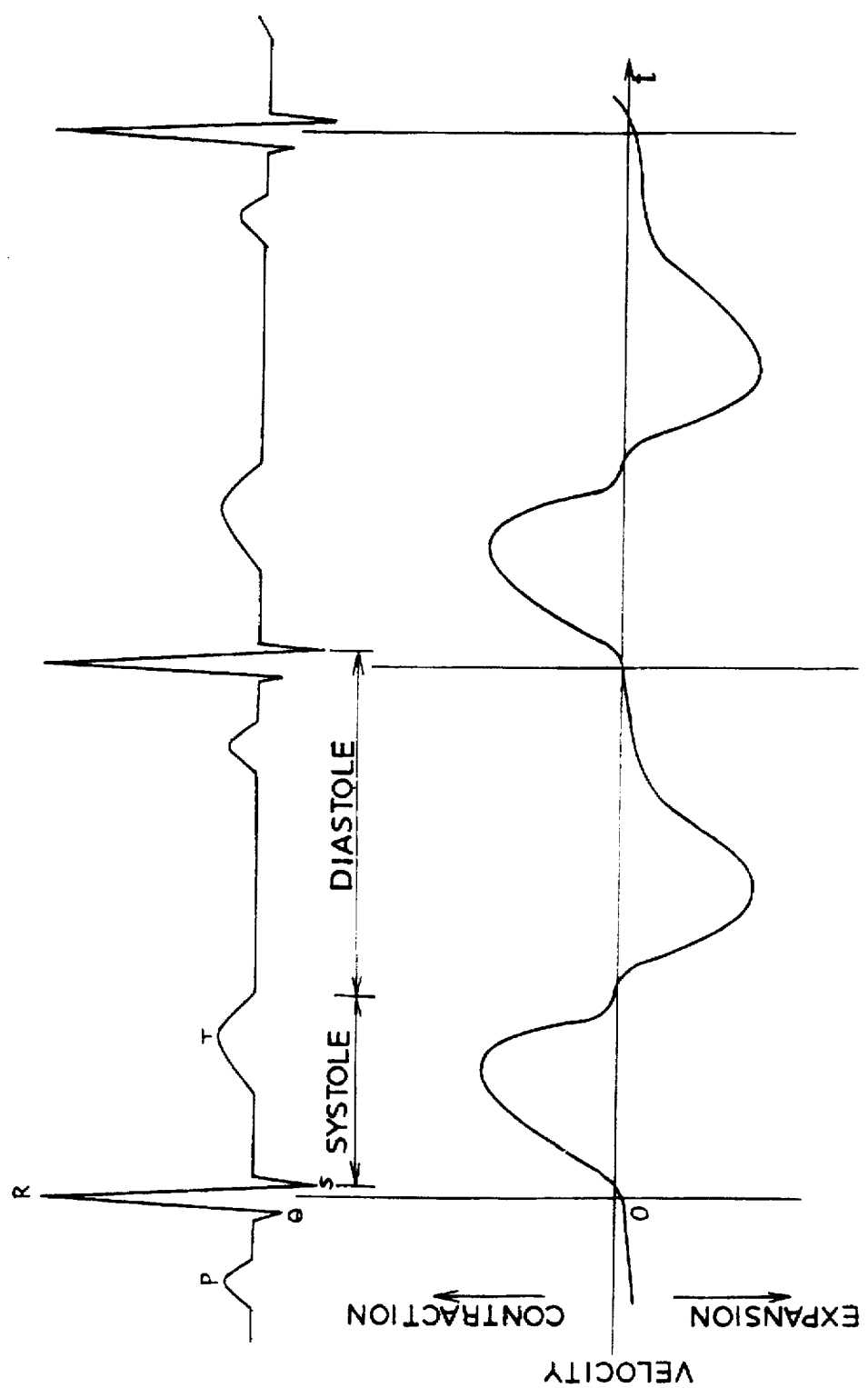
FIG. 53 shows a result of phase analysis in velocity.

Since the contraction of a heart is periodic, a movement velocity curve, which is exemplified in FIG. 53, can be regarded as a periodic function whose one period $T_0$ is defined by an interval of two R-waves on an electocardiogram. The Fourier series of the velocity curve is given by $$y(t) = A_0 + \sum_{n=1}^{\infty} \{a_n \cdot \cos(2\pi n f_0 t) + b_n \cdot \sin(2\pi n f_0 t)\}$$

wherein $f_0$: basic frequency; n: n-th frequency; and t=mT. Still, $$f_0 = 1/T_0 = 1/MT,$$

where m: ultrasonic frame number (m=1, 2, 3, ... M); M: the number of frames for one heart beat; and T: the scan period between ultrasonic frames. Thus, $$y(mT) = A_0 + \sum_{n=1}^{\infty} \{a_n \cdot \cos(2\pi nm/M) + b_n \cdot \sin(2\pi nm/M)\}$$

where $a_n$, $b_n$, and $A_0$ are each given by $$a_n = \frac{2}{M} \cdot \sum_{m=1}^{\infty} \{y(mT) \cdot \cos(2\pi nm/M)\}$$

$$b_n = \frac{2}{M} \cdot \sum_{m=1}^{\infty} \{y(mT) \cdot \sin(2\pi nm/M)\}$$

$$A_0 = \frac{1}{M} \cdot \sum_{m=1}^{M} Vm$$

Vm represents a velocity in a frame number m.

When the amplitude and phase of the n-th frequency are An and Pn, $$An = \sqrt{a_n^2 + b_n^2} \qquad (9)$$

$$Pn = \tan^{-1}\left(\frac{b_n}{a_n}\right) \qquad (10)$$

are given and y(mT) is represented by $$y(mT) = \frac{1}{M} \sum_{m=1}^{M} Vm + \sum_{n=1}^{\infty} \left\{ A_n \cdot \cos\left(\frac{2\pi nm}{M} - Pn\right) \right\} \qquad (11)$$

The phase determined by the expression (10) shows a time phase at a local point at the start of contraction and the amplitude determined by the expression (9) shows contractility of the local point.

In this way, Fourier transform of a velocity curve at each sampling volume gives the phase angle and amplitude of the n-th frequency at the volume in a systole. The phase angle data and amplitude data at all the sampling volumes are sent to the image data synthesizer 18 with changed color or brightness according to the amplitude. As a result, on the display unit 19, the phase angles and amplitudes of the n-th frequency at all the sampling points are superimposed on a B-mode image. The display of the phase angles is identical to the time display described in the movement timing analysis of movement and the display of the amplitudes is identical to the holding display of maximum velocities mentioned before. Therefore, quantitative analysis is possible in a systole, so that how long a certain local point delays in starting contraction than other local points can be shown quantitatively.

A tenth embodiment will now be explained according to FIGS. 54 to 63. An ultrasonic diagnosis apparatus of the present embodiment is to obtain the foregoing different types of movement information (that is, velocity, acceleration, movement timing information, and phase-analyzed information) and to measure a wide variety of physical values and statistic values on the movement information.

Figure 54:
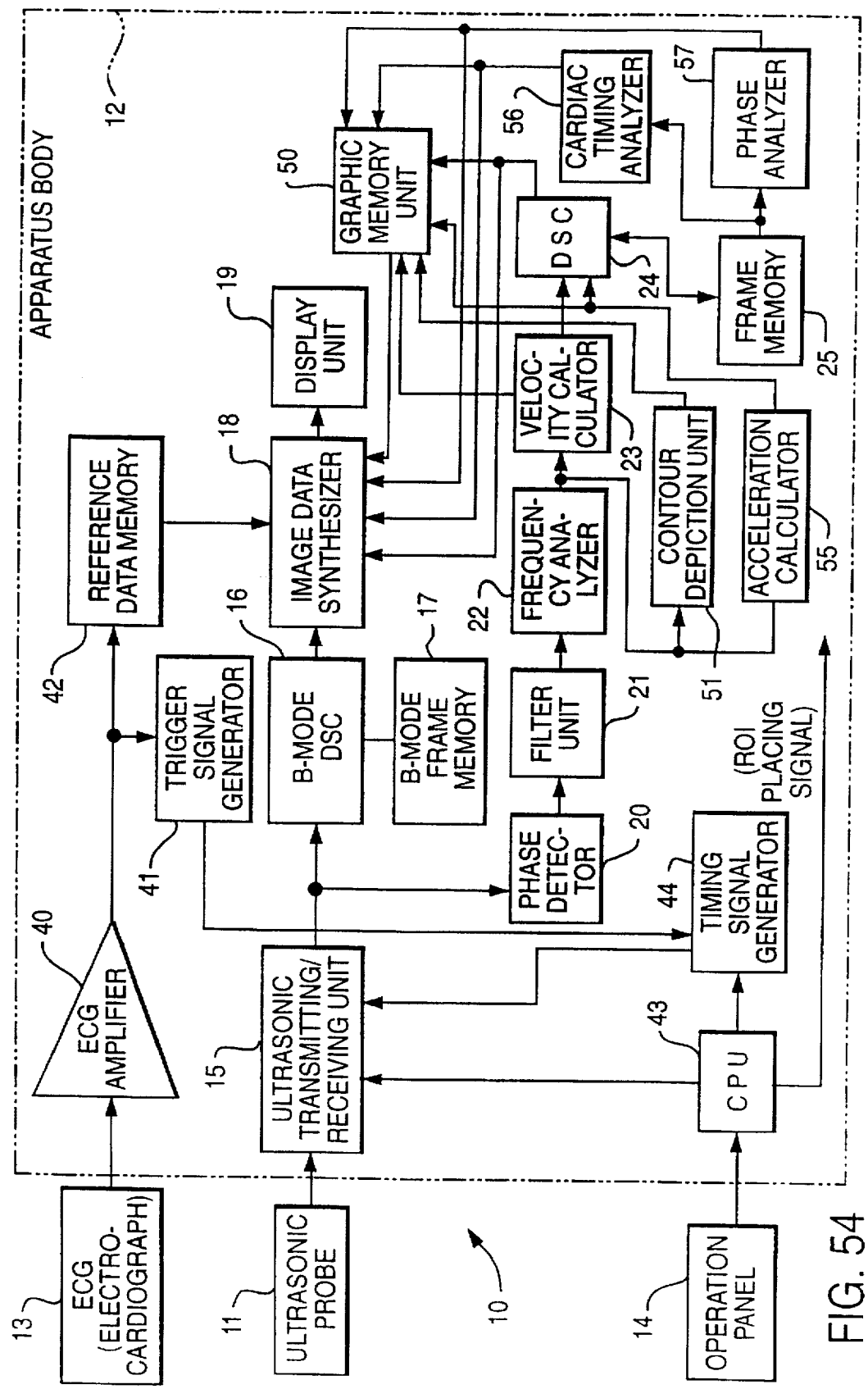
FIG. 54 is a block diagram showing an ultrasonic diagnosis apparatus of a tenth embodiment.

In an apparatus 10 in FIG. 54, at the output of the frequency analyzer 22, provided are the velocity calculator 23, contour depiction unit 51 and acceleration calculator 55. The outputs of the velocity calculator 23 and acceleration calculator 55 are sent to the DSC 24 and the outputs of the velocity calculator 23 and contour depiction unit 51 are sent to the graphic memory unit 50. At the read-out side of the frame memory 25, there are the cardiac timing analyzer 56 and velocity phase analyzer 57 and their outputs are sent to both the graphic memory unit 50 and image data synthesizer 18, to both of which supplied are the output data from the DSC 24. The graphic data from the graphic memory unit 50 are to be sent to the memory data synthesizer 18 to be superimposed on a B-mode tomographic image data.

Measurement functions of each type are as follows.

(i) velocity

The physical and statistic values concerning the velocity are carried out by the operation panel 14, CPU 43, velocity calculator 23, contour depiction unit 51, and graphic memory unit 50. So, in this case, it is possible to omit the acceleration calculator 55, cardiac timing analyzer 56 and velocity phase analyzer 57.

Placing a ROI (region of interest) through the operation panel 14 permits velocity data in vector quantity (absolute velocities) at the sampling volume positions within the ROI of each frame to be read from the frame memory 25. On the basis of the velocity data of each frame, different values are calculated for display on the display unit 19, together with a color velocity mapping image. A value to be measured can be selected by an operator through the operation panel 14.

Figure 55:
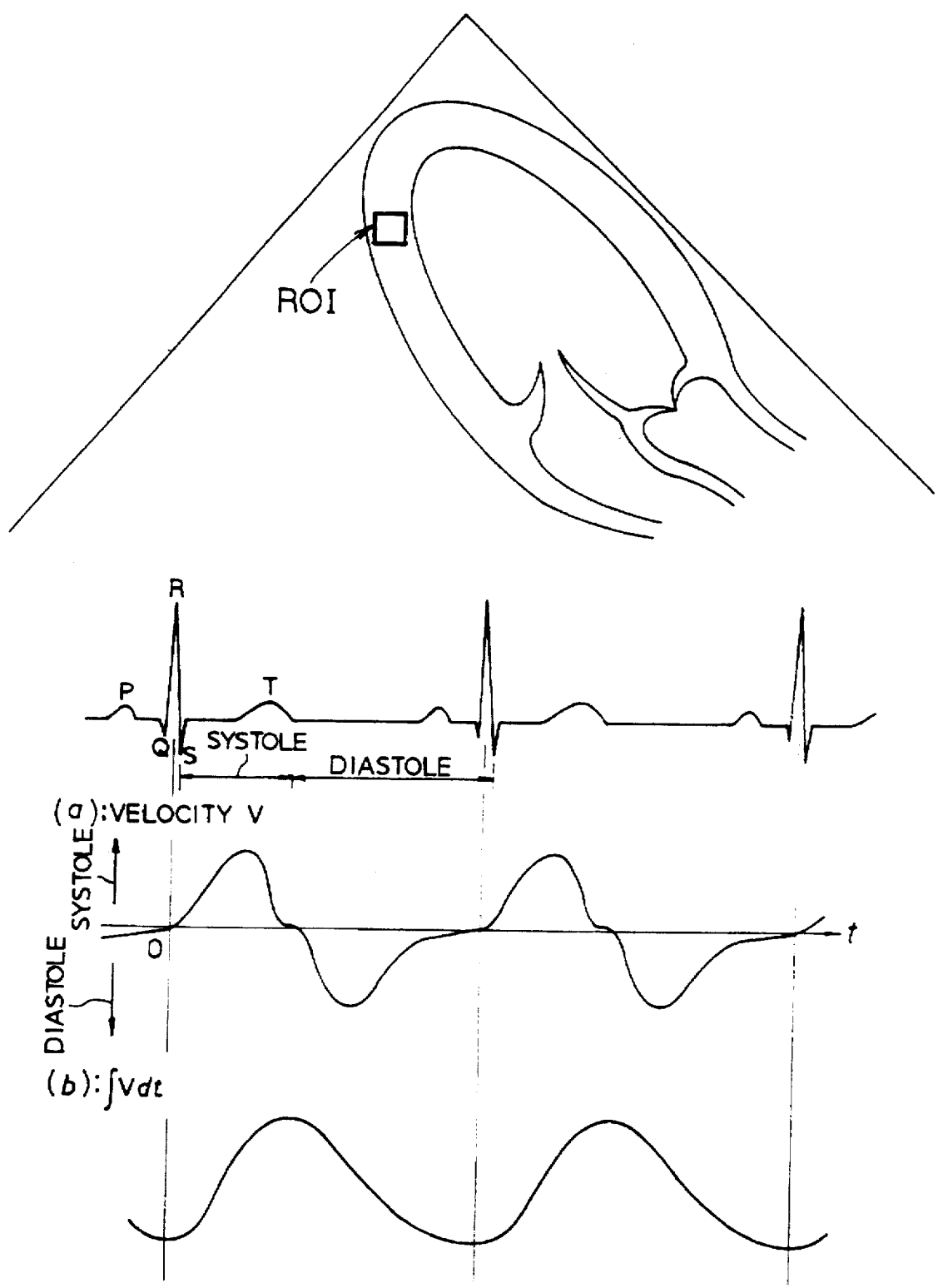
FIG. 55 shows a measurement result of a value related to a movement velocity.

For instance, in response to the selection, a mean velocity, a maximum velocity, or those integral values are calculated and displayed as shown in FIG. 55. In the figure, one curve (a) represents a mean velocity or maximum velocity changes in systole and diastole periods over time; the other (b) represents changes in integral value for either one of them. In such a case of FIG. 55, only one curve (a) or (b) can be displayed. A real-time color velocity image changes every moment, thus sometimes causing a situation in which understanding changes over elapsed time is difficult. But the measurement and display of the changing curve (a) or/and (b) over measurement time can get around such a drawback.

Further, for the velocity data of each frame within the placed ROI, the position or small region of the maximum velocity (or the center of gravity in a color display region within the ROI) of each frame is calculated and its position can be displayed as shown in FIG. 56 with a marker (refer to the crosses in the figure). Also a locus of the marker made for one cardiac cycle (refer to a line connecting a plurality of crosses) can be displayed, thus making it easy to recognize of directions of contraction and expansion.

Still further, for the velocity data of each frame within the placed ROI, the area of color displaying region can be computed and its curve over elapsed time can be displayed as shown in FIG. 57. This embodiment is such that the curves in systole periods represent changes in area of red or red-related color within the ROI; those in diastole periods represent changes in area of blue or blue-related color within the ROI.

Still further, for the velocity data of each frame within the placed ROI, the vector of a mean velocity is calculated and the locus of the vector for one cardiac cycle is displayed as shown in FIG. 58, on which the vector locus at an end-diastole is depicted as its one aspect. The vector locus will be in real time changed as shown in FIGS. 59A to 59F, that is, from the locus in a systole start to that at an end-diastole. This makes it easy to visually understand the directions of contraction and expansion of a region of interest.

Figure 60:
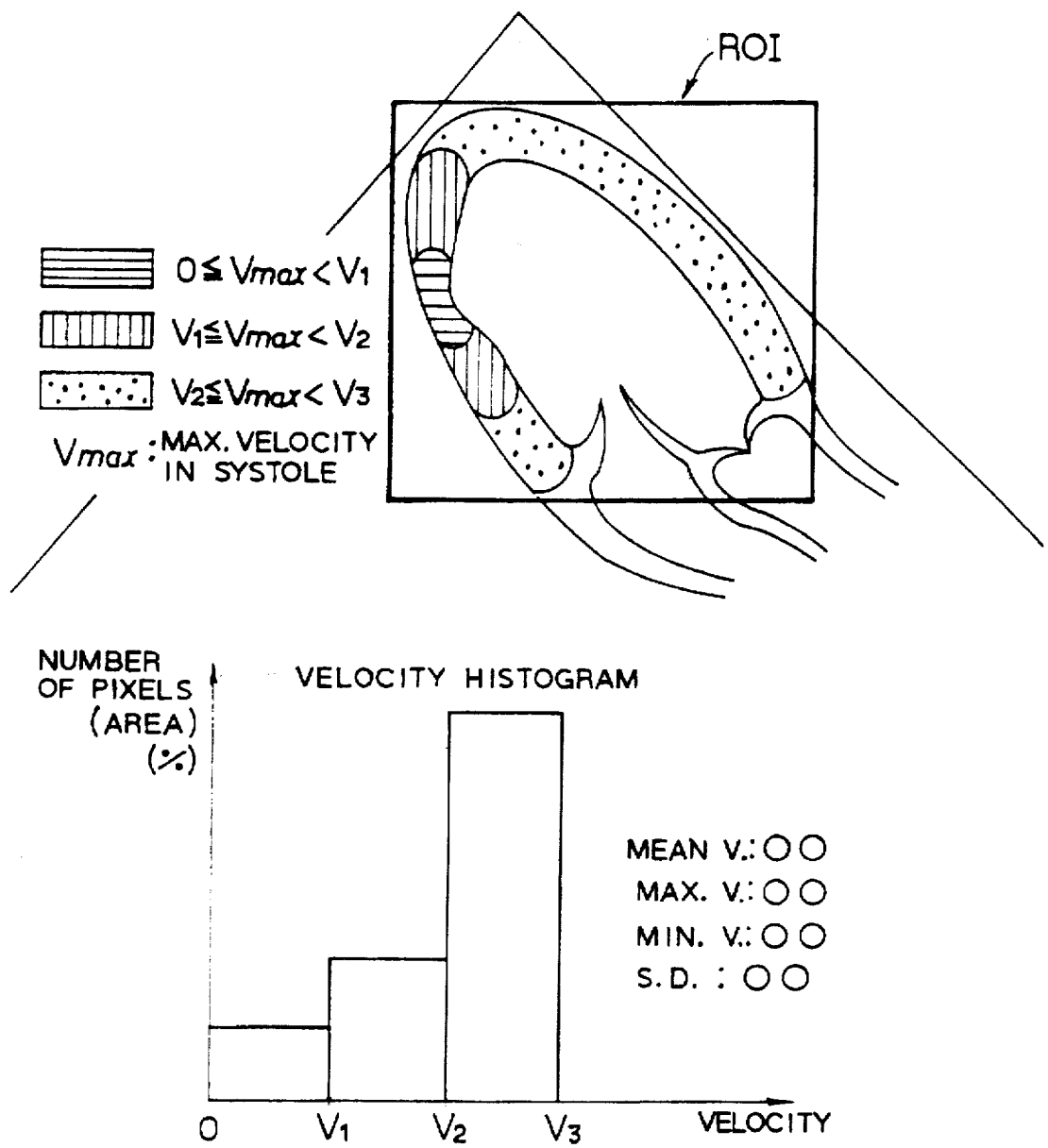

On the other hand, in case that maximum holding display is done as explained in the second embodiment, the above measurement and display will be available. For instance, color display regions within a placed ROI are calculated and displayed. Still, velocity histogram within a placed ROI is calculated, and its mean velocity, maximum velocity, minimum velocity, standard deviation and so on are calculated for displaying those as shown in FIG. 60.

Figure 61:
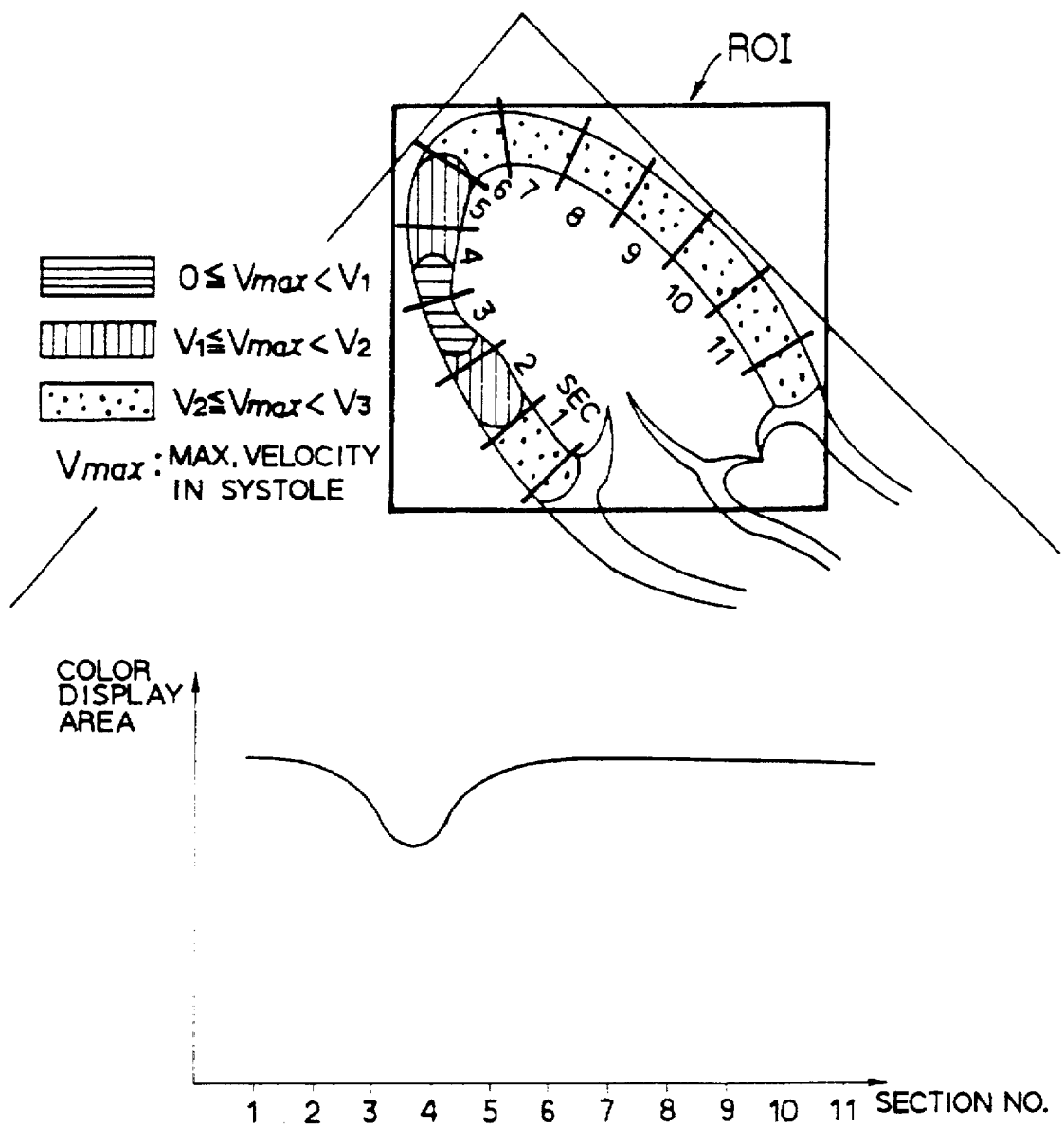

Further, another display is that first the color display region within a ROI is divided, like FIG. 61, into a plurality of small sections by segments, and then for every section, color areas (or, numbers of pixels) are calculated to display a curve shown therein. In this case, sections of velocities can be specified for graphing the corresponding color areas to the sections.

Moreover, using the aforementioned automatic trace will permit a color display region to be traced at its inner contour line LNin (or outer contour line). And it follows that changes over time in the area (or cross section of a left ventricle) surrounded by the traced contour line are calculated and displayed. Also calculated and displayed at the same time, when the contour line approximates an ellipse, are changes over time in diameters of its major and/or minor axes. FIG. 62 represents a time curve of the cross-section area of a left ventricle, the cross section being surrounded by the contour line LNin of an endocardium.

(ii) acceleration

The physical and statistic values concerning the acceleration are carried out by the operation panel 14, CPU 43, acceleration calculator 55, contour depiction unit 51, and graphic memory unit 50. So, in this case, it is possible to omit the velocity calculator 23, cardiac timing analyzer 56 and velocity phase analyzer 57.

In this case, one can also place a ROI through the operation panel 14 and perform the equivalent measurements to the velocity for the region within the ROI. Measured data are obtained by replacing the velocity data in measurement (i) with acceleration data. This should enhance analysis methods for movement of a cardiac muscle and a blood vessel wall.

(iii) cardiac timing

The physical and statistic values concerning the cardiac timing are carried out by the operation panel 14, CPU 43, velocity calculator 23, contour depiction unit 51, graphic memory unit 50 and cardiac timing analyzer 56. So, in this case, it is possible to remove the acceleration calculator 55 and velocity phase analyzer 57.

Figure 63:
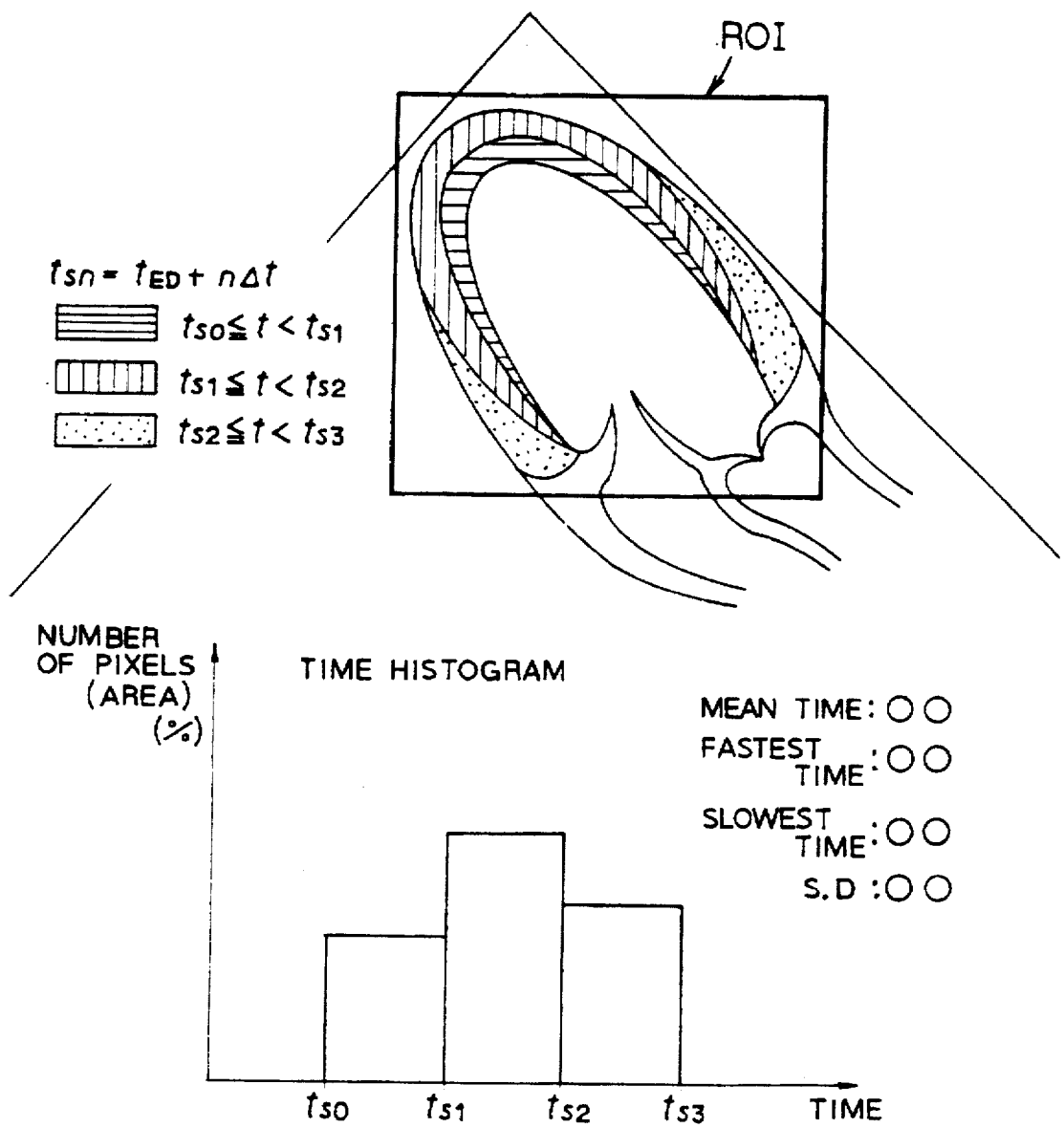
FIG. 63 represents a measurement result of movement timings.
Figure 64A:
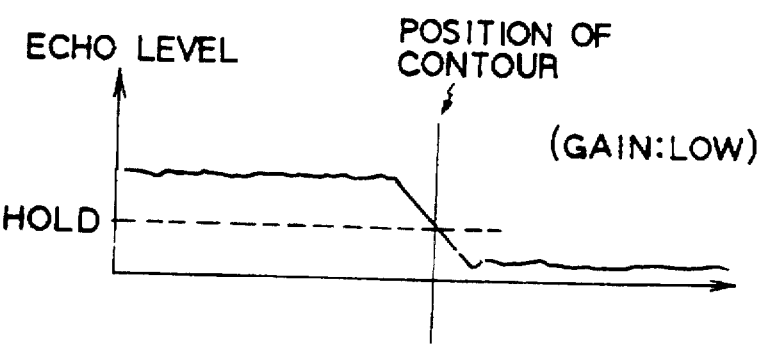
FIGS. 64A and 64B show a prior art by which a threshold is set for automatic trace.
Figure 64B:
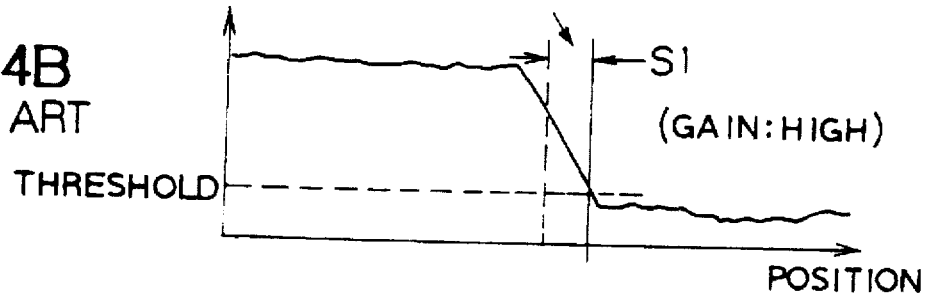

First, a ROI is placed, as shown in FIG. 63, on a color image through the operation panel 14. A time histogram is then calculated for the area surrounded by the ROI, and on the basis of the time histogram data, calculated are time-related data including a mean time, fastest time, slowest time, and standard deviation of times. These calculation results can be displayed together with the color velocity image, as shown in FIG. 63 (the figure shows an image at a time phase in a systole).

(iv). phase analysis

The physical and statistic values concerning the phase analysis for changes in time of a movement velocity are carried out by the operation panel 14, CPU 43, velocity calculator 23, contour depiction unit 51, graphic memory unit 50 and velocity phase analyzer 57. So, in this case, the acceleration calculator 55 and cardiac timing analyzer 56 may be removed.

Also a ROI is first placed on an image. Then calculated and displayed is a phase angle histogram of the n-th frequency within the ROI, including a mean angle, maximum angle, minimum angle, and standard deviation. The phase histogram of the first frequency are obtained by replacing the time data in the time histogram of the movement timing mentioned above with phase angle data. Also, calculated and displayed together with a color velocity image is an amplitude histogram of the n-th frequency within the ROI, including a mean amplitude, maximum amplitude, minimum amplitude, and standard deviation. The amplitude histogram of the first frequency are analogous to the velocity histogram explained in the item of velocity.

The advantages of the above-mentioned embodiments are as follows. First, a movement velocity in an ultrasonic beam of a cardiac muscle and a blood vessel wall and their absolute velocities are calculated (or estimated) for displaying, by color and in real time, those velocities in different ways. In addition, on the basis of the movement velocity, calculated are acceleration, movement timings, phase-analyzed information of the velocity change for color display in different modified ways. This provides in real time quantitative information of movement. Still, the contour lines of a cardiac muscle are also displayed on a color (two-dimension) movement image of it. An endocardium and epicardium can be automatically traced, increasing remarkably trace accuracy, reproducibility and improving operation efficiency of diagnosis as compared with the conventional manual trace. Moreover, there is no deviation of contour lines due to the conventional automatic trace method mentioned earlier.

In consequence, for movement of a cardiac muscle and a blood vessel wall, it is possible to obtain quantitative, precise and various movement data in a short time. Therefore, the apparatus is preferable to, for example, detection of local deteriorated portions in contraction ability in ischemic cardiodisease, objective diagnosis of left ventricle expansion disorders, and detection of positions and extent of abnormal paries movement in a conducting system of the heart.

Furthermore, a wide range of measurement is incorporated to provide much processed information on the basis of data of a color movement velocity image, increasing its flexibility and optional functions.

Still, a signal actually detected from an object being examined is only an ultrasonic echo signal with Doppler shift and the other movement-related data are calculated or estimated from the echo signal, thus retaining almost the same size and construction of the apparatus as an ultrasonic Doppler-type blood flow measuring apparatus already used.

On one hand, although the above second to tenth embodiments have been focused on the cardiac muscle as a diagnostic object in motion, the wall of a blood vessel may also be the object, which makes it possible to detect arterial sclerosis at local portions of a blood vessel wall and its quantitative condition. Further, there are some other ways of display: velocity or acceleration information of a cardiac muscle and a blood vessel wall is superimposed on an M-mode image, and velocity information of a cardiac muscle and a blood vessel wall is superimposed on its M-mode image and its contour is depicted, which makes it possible a real time, automatic trace of an endocardium or epicardium.

In the embodiments of the present invention, analog and digital electronic circuits can be used to compose exclusive processors or units on condition that they retain a enough real time property. Also, those processors and units can use software processing.

Figure 69:
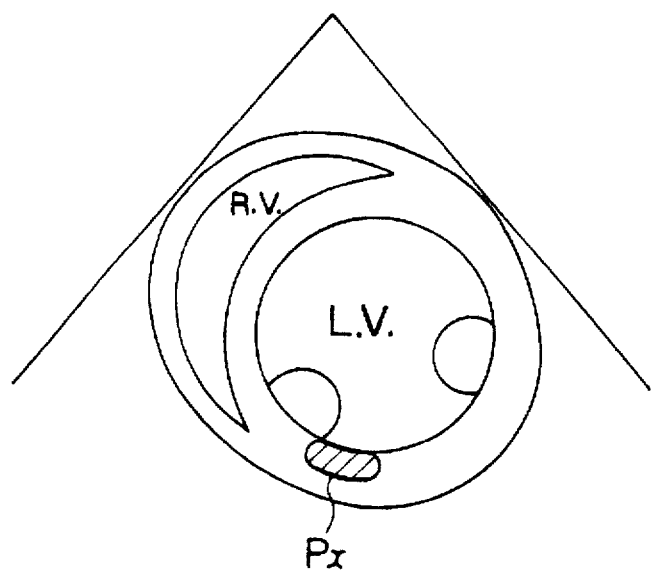
FIG. 69 pictorially shows a deteriorated portion of paries movement of a cardiac muscle.
Figure 70:
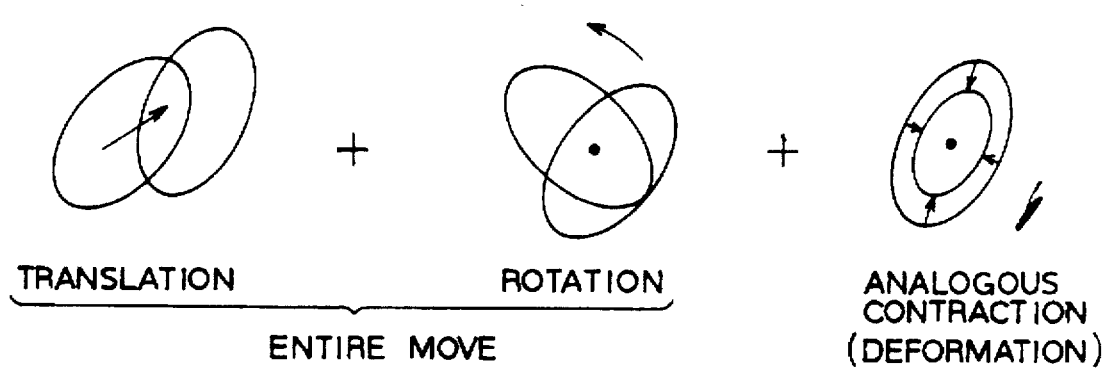
FIG. 70 pictorially explains translation, rotation, and analogous contraction of a cardiac muscle.

An eleventh embodiment will now be explained according to FIGS. 65 and 69.

The present embodiment relates to an ultrasonic diagnosis apparatus utilizing a diagnosis method called "a stress echography".

Figure 65:
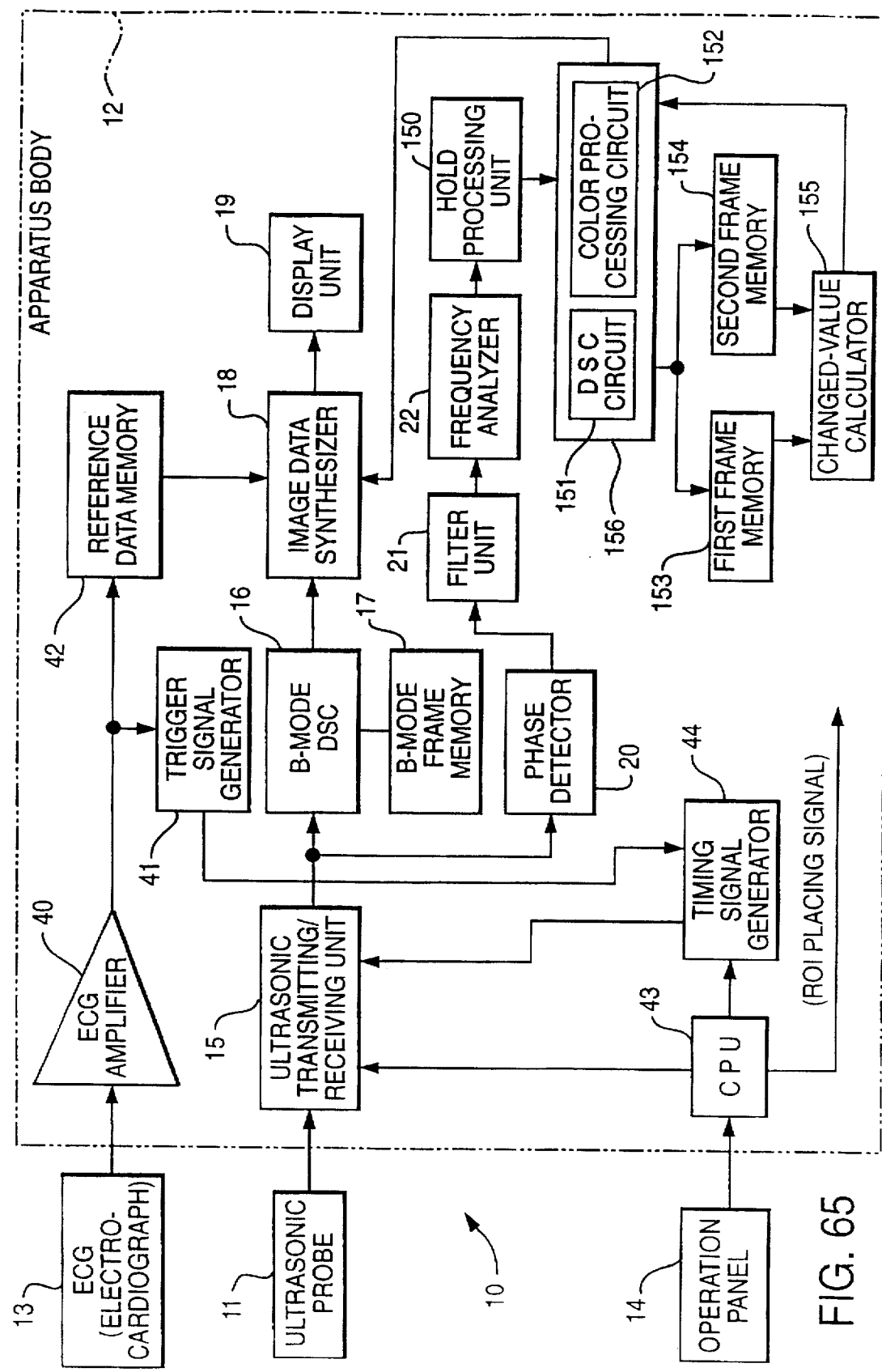
FIG. 65 is a block diagram showing an ultrasonic diagnosis apparatus of an eleventh embodiment.

An ultrasonic diagnosis apparatus 10 shown in FIG. 65 has a hold processing unit 150, a color Doppler DSC 156, a first and second frame memories 153 and 154, and a changed-value calculator 155, all of which are disposed between the frequency analyzer 22 and the image data synthesizer 18.

The analysis results of Doppler frequencies in the frequency analyzer 22 are sent to the next hold processing unit 150 to be stored temporarily therein. The hold processing unit 150 has a function of holding maximums of velocities in a systole period at each sapling volume (pixel) every heart beat.

The stored data in the unit 150 will then be sent to the DSC circuit 156 having a DSC 151 for converting scan systems and a color processing circuit 152 having a lookup table to color velocity data. As a result, the converted and colored velocity data are outputted from the DSC 156 to the image data synthesizer 18.

The DSC circuit 151 is to select some of appropriate heart beats before a stress such as jogging is given to a patient, calculate maximum contraction velocities Vmax(0,x,y) at each pixel (forming a two-dimensional coordinate (x,y)) during the selected heart beats, and store the maximum contraction velocities Vmax(0,x,y) in the first frame memory 153. Then, with the patient given a stress, the DSC circuit 151 will also calculate maximum contraction velocities every heart beat, pick up the maximum contraction velocities Vmax(n,x,y) of each pixel at the n-th heart beat, and store them in the second frame memory 154.

Then the changed-value calculator 155 will read the data Vmax(0,x,y) and Vmax(n,x,y) from the first and second frame memories 153 and 154, calculating one of the following three changed-values as a parameter of the stress echography.

$$Vmax(n,x,y)/Vmax(0,x,y) \quad (12a)$$

$$Vmax(n,x,y)/Vmax(0,x,y) \quad (12b)$$

$$(Vmax(n,x,y)-Vmax(0,x,y))/Vmax(0,x,y) \quad (12c)$$

The changed-value thus-calculated is sent to the color processing circuit 152, in which the value data are colored according to its absolute values and positive/negative signs (the direction of a change in velocity between frames). The colored changed-value data are sent, via the image data synthesizer 18, to the display unit 19 for display. The image displayed thereon is updated every heart beat, since the hold processing unit 150 is so.

Suppose that changed-values are calculated by the formula (12c) and their magnitudes are displayed with changed brightness and their positive and negative signs are displayed in red and blue, respectively. When a patient shows a normal paries movement of a cardiac muscle before stressing, stressing allows the heart to increase its pumping capacity, the contraction force being displayed in red. In contrast, when myocardial ischemia is induced by the application of the stress and paries movement is deteriorated at local positions, the positions will turn into blue. Thus it is easy to distinguish the myocardial ischemia positions from other normal portions.

In case that a patient has a deteriorated paries movement portion before stressing and recovery of contraction ability is examined by drugs and so on, a region at which the contraction force has been recovered is shown in brighter red, thereby showing that vaibility still remains therein. On the other hand, if the contraction force has not been recovered in a portion Px shown in FIG. 69, for example, the portion Px is shown in darker red, black or blue depending on the values of the velocities, thus showing that the portion Px has totally been sphacelous.

In this way, the conditions of a cardiac muscle are displayed understandably and accurately before and after stressing. This provides real-time and high-accuracy diagnosis.

A twelfth embodiment of the present invention will then be explained according to FIGS. 66 to 69.

Figure 66:
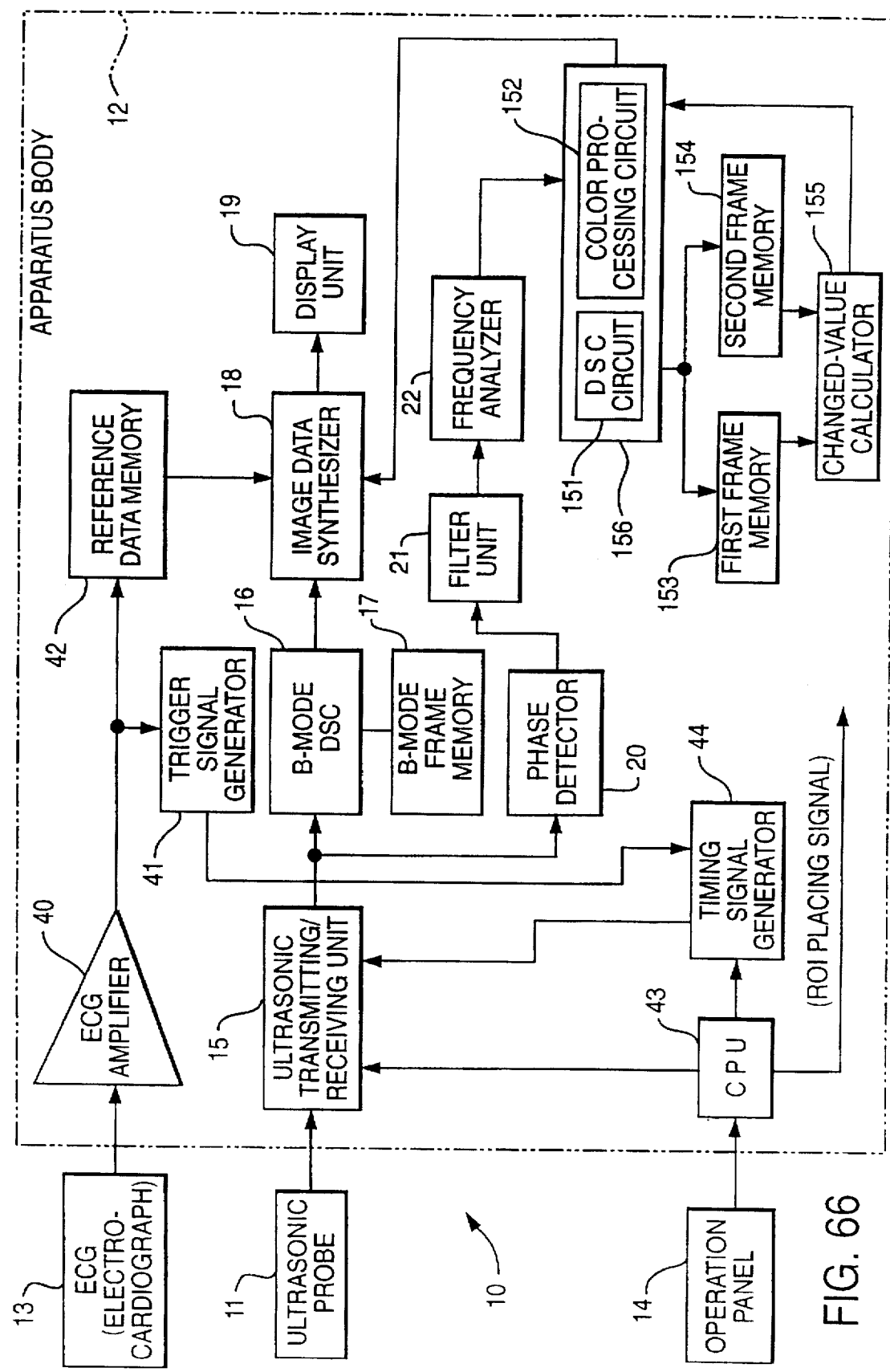
FIG. 66 is a block diagram showing an ultrasonic diagnosis apparatus of a twelfth embodiment.

The present embodiment will also utilize a stress echography, but the hold processing unit 151 in FIG. 65 is not required. Such a whole constrcution is illustrated in FIG. 66.

The DSC circuit 151 is to select some of appropreate heart beats before stressing, calculate movement velocities V(0, m0,x,y) and cardiac cycles T0 (R-R intervals) at their heart beats at each pixel (forming a two-dimensional coordinate (x,y)), every frame, during the selected heart beats, and store those data in the first frame memory 153. The variable m0 is the frame number of an ultrasonic scan counted from a referential R-wave on an electrocardiogram before stressing. Then, with the patient given a stress, the DSC circuit 151 will also calculate movement velocities and cardiac cycles Tn every heart beat, pick up the velocities V(n,m1,x,y) of each pixel at the n-th heart beat, and store them in the second frame memory 154. The variable m1 shows the frame number of an ultrasonic scan counted from a referential R-wave on an electrocardiogram under stressing.

Then the changed-value calculator 155 will read the data V(0,m0,x,y) and V(n,m1,x,y) from the first and second frame memories 153 and 154, calculating one of the following three changed-values as a parameter in the stress echography.

$$V(n,m1,x,y)/(V(0,m0,x,y)) \quad (13a)$$

$$V(n,m1,x,y) - V(0,m0,x,y) \quad (13b)$$

$$(V(n,m1,x,y) - V(0,m0,x,y))/V(0,m0,x,y) \quad (13c)$$

By the way, because the number of heart beats, in general, will be changed before and after stressing, care must be taken when comparing two velocities at the same cardiac timings before and under stressing periods. In the present embodiment, assuming the frame number at the n-th heart beat under stressing to be m1, the corresponding m0 to. m1 at the same cardiac timings before stressing is calculated by $$m0=m1 \times (T0/Tn) \quad (14).$$

The changed-value calculated above is sent to the color processing circuit 152, in which the value data are colored (or brightness changed) depending on its absolute values and positive/negative signs. The changed-value data thus-processed are superimposed on a B-mode two-dimensional tomographic image shown in FIG. 69. The image can be displayed in real time under stressing.

Now one example of display will be explained, which is suitalbe for comparison two images before and after stressing. This process can be done by the changed-value calculator 155 as follows.

Figure 67:
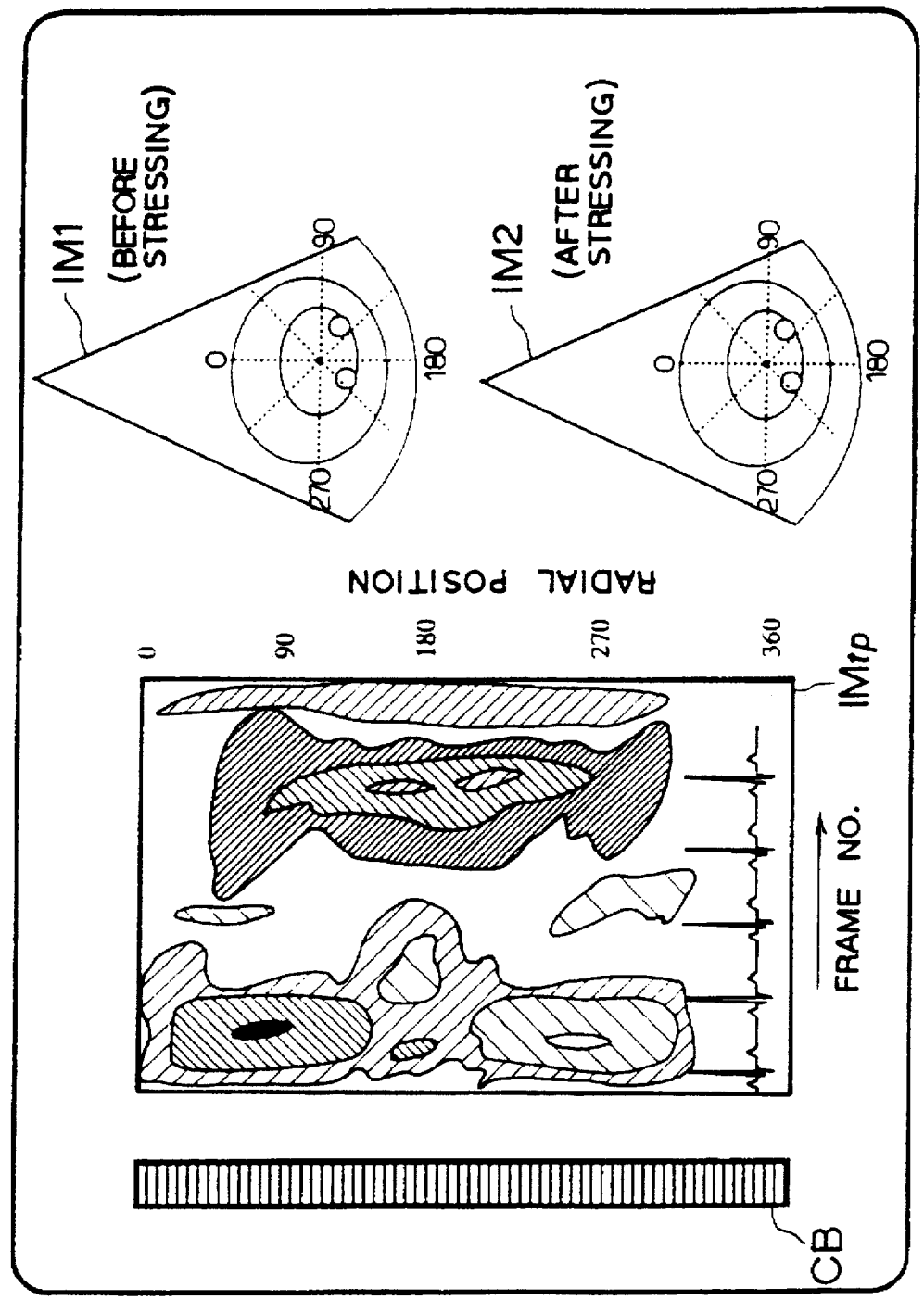
FIG. 67 is an example of stress echography image in before- and after-stressing.

Prior to stressing, the mean value of velocities is calculated on the velocities residing on each imaginary radial line extending from the center of a ventricle, the mean value data being stored in a memory pixel by pixel. The same process is repeated after a stress has been given. Then, a parameter of V2/V1, V2–V1, or (V2–V1)/V1 is calculated for every position of the radial linis, where V1is a mean value before stressing and V2 is a mean value after stressing. The calculated parameter data and original velocity data are displayed as shown in FIG. 67. In the displayed image, the two velocicy images IM1 (before stressing) and IM2 (after stressing) are compared on the same screen. Besides, its calculation results are imaged as a two-dimensional image IMtp with a referential color bar CB. The image IMtp has a longitudinal axis representing radial positions and a transverse axis representing frame numbers (i.e. elapsed times). The calculated values of the parameter are brightness-modulated on the image IMtp, but their values can also be expressed by changed colors, hue, or color tone. The color bar CB is useful for recognizing magnitudes of changed-values in velocity with referential colors or brightness.

The above display requires that the spatial positions of images be at the same positions between before- and after-stressing. One method for the positioning is that the center of gravity (or area) of an object being diagnosed is determined before and after stressing and both the centers are brought into one position.

Figure 68:
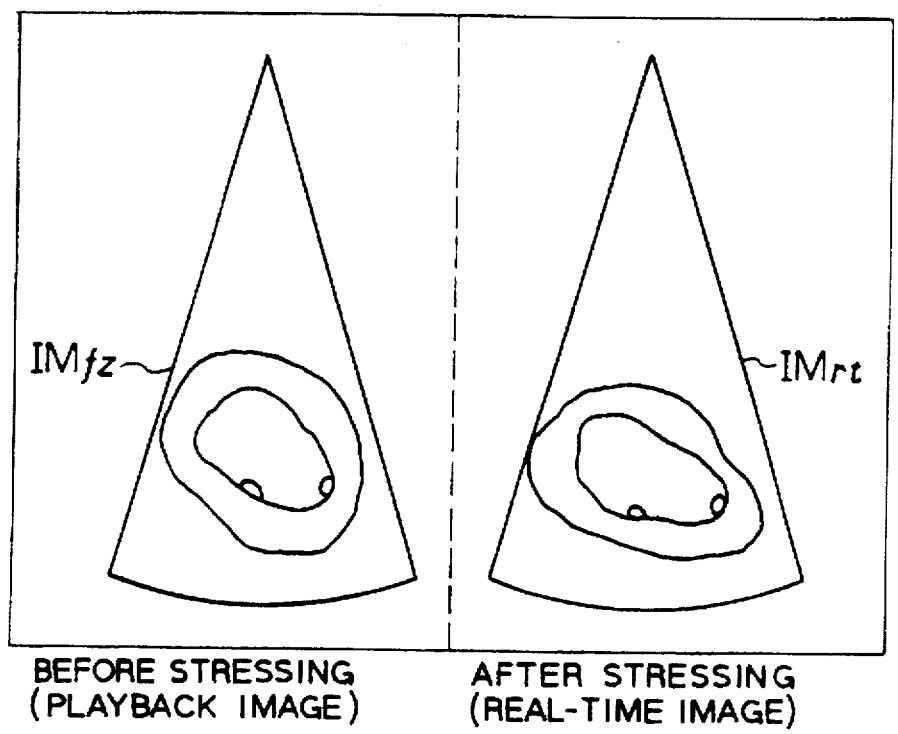
FIG. 68 pictorially shows positioning of images in before- and after-stressing.

Another spatial positioning is to use manual adjustment of an image. When after-stressing images are diagnosed as shown in FIG. 68, a doctor plays back after-stressing real-time images IMrt on one divided region of a screen (on the other divided region, a before-stressing frozen image IMfz is displayed), and select by hand one of the images IMrt so that both the images IMrt and IMfz become the same position.

In the above eleventh and twelfth embodiments, although the movement velocity of a cardiac muscle has been discussed, its acceleration may also be adopted as a parameter of the movement. In such a case, an acceleration calculator 55 described before will be arranged at the output of the frequency analyzer 22 in FIG. 65 or 66; then the output signals of the acceleration calculator 55 should be sent to the hold processing unit 150 or the DSC 156. As a result, changed-values in acceleration over a plurality of frames can be displayed in the same manner as above.

A thirteenth to a fifteenth embodiment will now be explained according to FIGS. 70 to 75, all of which relate to removal of entirely uniform movement components such as movement of translation and rotation of a cardiac muscle. These embodiments are further improvement for the variation shown in FIG. 12.

First of all, the principle of the removal will be explained, in which entirely combined (or almost entirely combined) and, uniform movement components of tissues within an objective region are to be estimated and removed from each of two-dimensional velocities. A least square method is used here as an example of cross correlation methods.

Suppose that movement of the cardiac muscle of a left ventricle are detected with a sector probe from a body surface through an ultrasonic Doppler method. It is almost true that the movement can be decomposed into two types of movement: One is analogously-changing deformity directly accompanied by a contraction and an expansion of the cardiac muscle and the other is translation and rotation of the whole cardiac muscle. This supposition is improper to a patient whose cardiac muscle deformity is large in size because of an abnormality of the cardiac muscle. But healthy hearts of men and women keep analogous shape in contraction and expansion, so the supposition can properly be adopted. Besides, it seems that the supposition can be applied to most ischemic cardiodisease patients. It is important for analysis of movement of a cardiac muscle to remove the translation and rotation added uniformly to the analogously-changing deformity.

Figure 71:
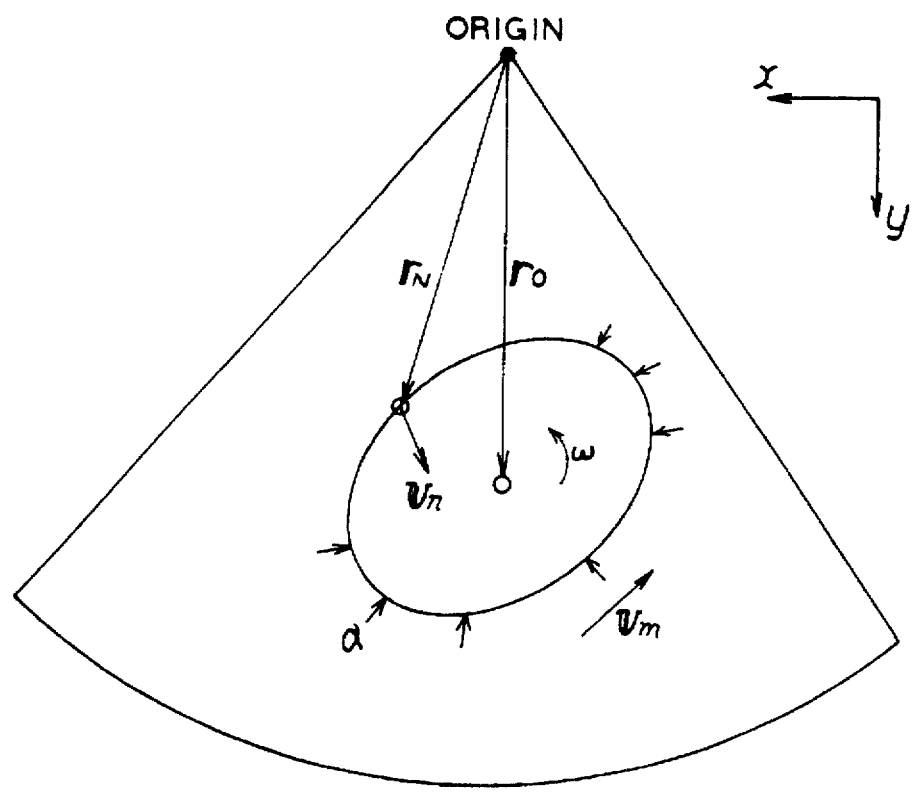
FIG. 71 is a model for analysis of movement of a cardiac muscle.

Thus, on the basis of movement velocity data of the cardial muscle of a left ventricle, its translation and rotation will be estimated. As shown in FIG. 71, it is assumed that objective movement can be decomposed into contraction and rotation (the velocity α of contraction), translation (its velocity v), and rotation (its angular velocity ω), and α, v and ω will be estimated by means of a least square method. Depending on conditions of movement of a cardiac muscle, either one of translation or rotation can be omitted. It is supposed that the center of contraction has been obtained by an appropriate means.

First, each parameter is designated as follows (see FIG. 71):

center of contraction (center of rotation); $r_0$
translation velocity; $v_m$
rotational angular velocity for $r_0$; $\omega$
contraction speed; $\alpha$
movement velocity at position of $r_N$; $v_N$, where italicized characters represent vector quantities.

Now, the followings will be supposed:

(1) the center of contraction is one point (or the entire object contracts towards one point),
(2) the centers of contraction and rotation are common, and
(3) the contour of a cardiac muscle deforms in analogous shapes when contracting, and the contraction speed is uniform for the center of contraction.

In addition, as explained above, it is supposed that the movement of a cardiac muscle is decomposed into translation, rotation and analogous contraction. A movement velocity $v_N$ at position of $r_N$ is given by the following equations (15a) and (15b):

$$v_N = v_m + \alpha \cdot e_r + \omega |r_N - r_0| e_\theta + \Delta v_N \tag{15a}$$

$$e_r = \frac{r_N - r_0}{|r_N - r_0|} \tag{15b}$$

where $e_\theta$ is a unit vector(in a clockwise direction) orthogonal to $e_r$.

In the above equations (15a) and (15b), $\Delta v_N$ is a difference component between a movement velocity of each pixel estimated with a model expressed by $v_m$, $\alpha$ and $\omega$ and a movement velocity actually observed at each pixel; it represents a local deformation that can not be explained using the model.

Then, supposing a velocity component in an ultrasonic beam, which is observed by the Doppler method, to be $v_N$, the equation (16) is given as below;

$$v_N = \frac{v_N \cdot r_N}{|r_N|} \tag{16}$$

$$= v_m \cdot \frac{r_N}{|r_N|} + \alpha \cdot \frac{(r_N - r_0) \cdot r_N}{|r_N - r_0||r_N|} +$$

$$\omega \cdot \frac{|r_N - r_0|}{|r_N|} e_\theta \cdot r_N + \frac{\Delta v_N \cdot r_N}{|r_N|}$$

Now, the following expanded expressions will be introduced.

$v_m = (v_{mx}, v_{my})$ $r_N = (x_N, y_N)$ $r_0 = (x_0, y_0)$ $e_\theta = \frac{(y_N - y_0, -x_N - x_0)}{\sqrt{(x_N - x_0)^2 + (y_N - y_0)^2}}$ (clockwise)

$\epsilon_N = \frac{\Delta v_N \cdot r_N}{|r_N|}$

Therefore, $$v_N = \frac{1}{\sqrt{x_N^2 + y_N^2}} \left\{ v_{mx} x_N + v_{my} y_N + \right. \tag{17}$$

$$\left. \frac{\alpha}{\sqrt{(x_N - x_0)^2 + (y_N - y_0)^2}} \cdot ((x_N - x_0) x_N + (y_N - y_0) y_N) + \right.$$

$$\left. \omega \sqrt{(x_N - x_0)^2 + (y_N - y_0)^2} \cdot \frac{(y_N - y_0) x_N + (x_N - x_0) y_N}{\sqrt{(x_N - x_0)^2 + (y_N - y_0)^2}} \right\} + \epsilon_N$$

Hence, $$v_N = \frac{x_N}{\sqrt{x_N^2 + y_N^2}} v_{mx} + \frac{y_N}{\sqrt{x_N^2 + y_N^2}} v_{my} + \tag{18}$$

$$\frac{(x_N - x_0) x_N + (y_N - y_0) y_N}{\sqrt{(x_N - x_0)^2 + (y_N - y_0)^2} \sqrt{x_N^2 + y_N^2}} \alpha +$$

$$\frac{(y_N - y_0) x_N - (x_N - x_0) y_N}{\sqrt{x_N^2 + y_N^2}} \omega + \epsilon_N$$

and further $$v_N = \frac{x_N}{\sqrt{x_N^2 + y_N^2}} (v_{mx} - y_0 \omega) + \frac{y_N}{\sqrt{x_N^2 + y_N^2}} (v_{my} - x_0 \omega) + \tag{19}$$

$$\frac{(x_N - x_0) x_N + (y_N - y_0) y_N}{\sqrt{(x_N - x_0)^2 + (y_N - y_0)^2} \sqrt{x_N^2 + y_N^2}} \alpha + \epsilon_N$$

Therefore, when taking $\zeta$ and $\eta$ as parameters representing a movement in which translation and rotation is combined such as:

$$\zeta = v_{mx} + y_0 \omega \tag{20}$$

$$\eta = v_{my} + x_0 \omega \tag{21},$$

the following equation (22) is given as $$v_N = \frac{x_N}{\sqrt{x_N^2 + y_N^2}} \zeta + \frac{y_N}{\sqrt{x_N^2 + y_N^2}} \eta + \tag{22}$$

$$\frac{(x_N - x_0) x_N + (y_N - y_0) y_N}{\sqrt{(x_N - x_0)^2 + (y_N - y_0)^2} \sqrt{x_N^2 + y_N^2}} \alpha + \epsilon_N$$

Then, assume that $\zeta$, $\eta$ and $\alpha$ are estimated by an appropriate means, and the results of estimation are expressed as $\zeta^*$, $\eta^*$, and $\alpha^*$, respectively. Using the parameters $\eta^*$ and $\zeta^*$ it is possible to estimate a translation component and a rotation component combined with each other.

After having removed the translation and rotation components, a contraction velocity at each pixel is given by $$U_N = \left( v_N - \frac{x_N \zeta^* + y_N \eta^*}{\sqrt{x_N^2 + y_N^2}} \right) \cdot \tag{23}$$

$$\frac{\sqrt{(x_N - x_0)^2 + (y_N - y_0)^2} \sqrt{x_N^2 + y_N^2}}{(x_N - x_0) x_N + (y_N - y_0) y_N}$$

The velocity component $U_N$ of movement of a cardiac muscle, which is obtained by removing translation and rotation components entirely and uniformly superimposed on the movement, is considered to be a true velocity of its contraction and expansion. Usually, an ultrasonic Doppler measurement depends on an incidence angle of its beam to an object, but specifying the center of contraction can correct the dependence to the beam angle.

Now there are several ways for determining the center of contraction as follows.

(1) The center of a left ventricle is determined by means of direct observation of a two-dimensional velocity image, and then a data of its center is input with a device, such as a keyboard, mouse and track ball.

(2) The contour of a left ventricle is extracted, based on a B-mode image or color Doppler image of velocity, and its center of area is determined as the center of contraction.

(3) The position determined in the ways (1) or (2) is centered and its proximate region is regarded to include the center of contraction therein. Then the least square method is applied to calculate a correlational coefficient, estimating and adopting parameters for the best correlational coefficient.

It is determined that a calculation region is on an objective organ; the region may be limited by placing a ROI thereon. Further, identification of the objective organ is based on image filters, utilizing brightness level change in a B-mode image, power mode level change in a Doppler image, or their level changing quantities.

In case that velocity data in vector quantity in a tomographic image are detected, the foregoing equation (18) is replaced by the following equations (24) and (25) and the same least square method is used for estimation of the true movement accompanied by contraction and expansion.

That is, the equation (15a) is again cited as follows. Here, each element in this equation is decomposed into components in x-axis and y-axis directions as below.

$$v_N = v_m + \alpha e_r + \omega |r_N - r_0| e_\theta + \Delta v_N$$

$e_r$ and $e_0$ are defined as $$v_N = (v_{N_x}, v_{N_y}), \quad v_m^2 = (v_{mx}, v_{my})$$
$$r_N = (x_N, y_N), \quad r_0 = (x_0, y_0)$$
$$e_x = (1,0), \quad e_y = (0,1)$$

$$e_r = \frac{r_N - r_0}{|r_N - r_0|} = \frac{(x_N - x_0, y_N - y_0)}{\sqrt{(x_N - x_0)^2(y_N - y_0)^2}}$$

$$e_0 = \frac{(y_N - y_0, x_N - x_0)}{\sqrt{(x_N - x_0)^2(y_N - y_0)^2}}$$

producing the two components $v_{N_x}$ and $v_{N_y}$ of $v_N$ as follows.

$$v_{N_x} = v_N \cdot e_x \quad (24)$$
$$= v_{mx} + \alpha \frac{x_N - x_0}{\sqrt{(x_N - x_0)^2(y_N - y_0)^2}} +$$
$$\omega(y_N + y_0) + \epsilon_{N_x}$$

$$v_{N_y} = v_N \cdot e_y \quad (25)$$
$$= v_{my} + \alpha \frac{y_N - y_0}{\sqrt{(x_N - x_0)^2(y_N - y_0)^2}} -$$
$$\omega(x_N + x_0) + \epsilon_{N_y}$$

In this case, the translation and rotation components can be estimated independently, though both of which are caused by the entire movement of a cardiac muscle.

In the present estimation, the movement model expressed by the equation (15a) is only one example. The model should be determined appropriately on the basis of an objective organ and its cross section. The least square method enables estimation of a movement component almost combined of an organ or objective tissue.

Still, the model, in which the center of contraction is supposed, is also one example for the present invention. If it is difficult to consider that the contraction is directed to one point, another appropriate model should be used.

The least square method has been used for estimating the combined movement of translation and rotation, but in case of entire translation, it is possible to estimate it, based on a mean velocity of an entire object or specified region.

Now, a thirteenth embodiment will be explained according to FIGS. 72 and 73.

Figure 72:
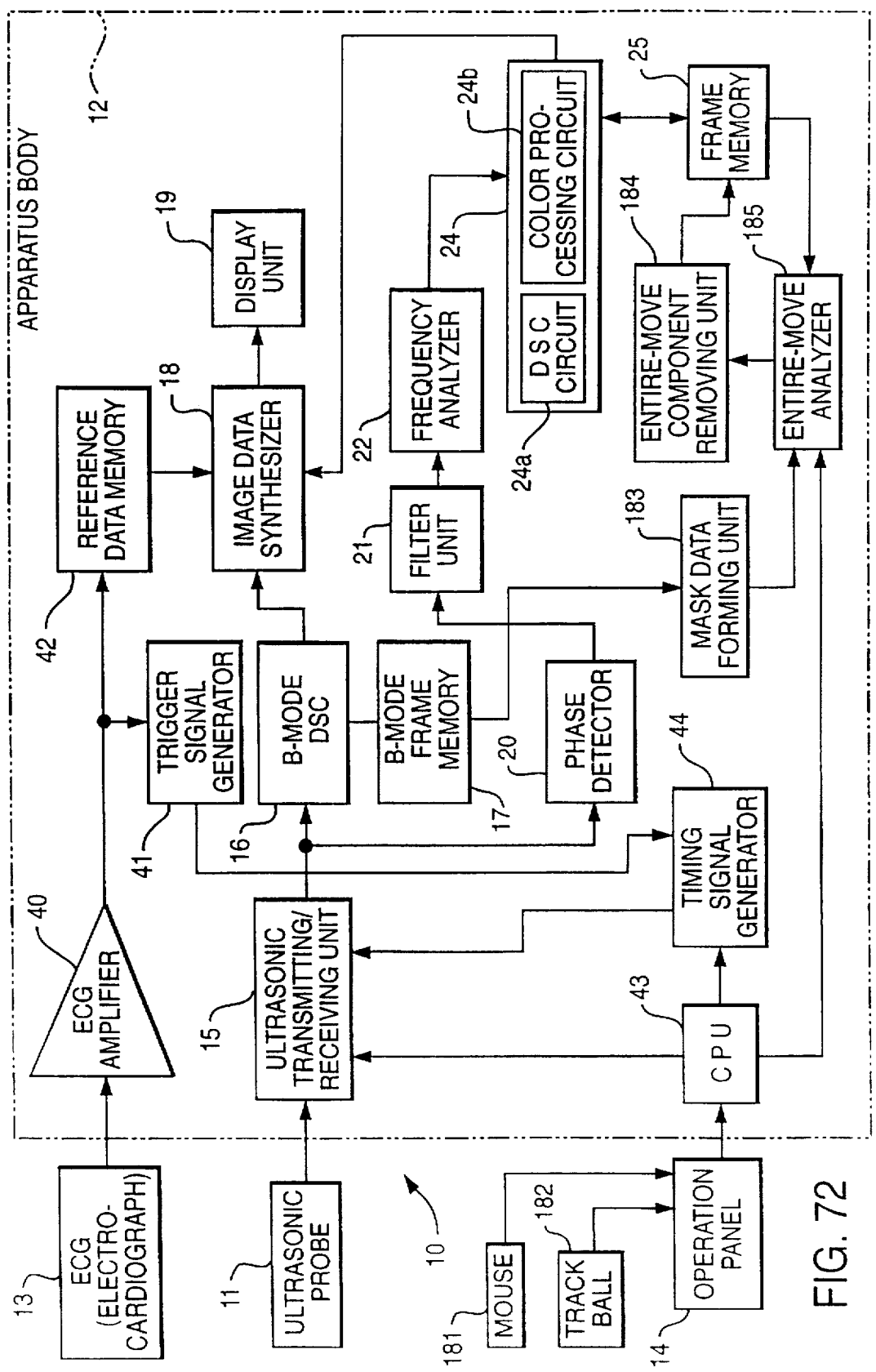
FIG. 72 is a block diagram showing an ultrasonic diagnosis apparatus of a thirteenth embodiment.

An ultrasonic diagnosis apparatus 10 shown in FIG. 72 has newly a mouse 181 and a track ball 182 connecting to the operation panel 14, so that one can place a ROI and specify a center of contraction through them.

In addition, in the apparatus 10, there are provided a mask data forming unit 183, an entire move component removing unit 184, and an entire move analyzer 185 between the B-mode frame memory 17 and the frame memory 25. But the velocity calculator is not present, and the output of the frequency analyzer 22 is directly sent to the DSC 24.

The frame memory 25 has a large memory capacity enough to store at least color velocity data in scalar quantity of one heart beat. The stored velocity data, either data of ultrasonic beam scanning or converted data to standard TV signals, can be sent to the entire move analyzer 185.

The mask data forming unit 183, which will receive B-mode data from the B-mode frame memory 17, determines the region of a cardiac muscle based on the B-mode data and forms mask data for an area other than the cardiac muscle, the mask data being sent to the entire move analyzer 185.

Determining the region of a cardiac muscle is carried out by setting a threshold to brightness level to pixels in B-mode data and adopting pixel data of level more than the threshold. In this case, since there are noises among data and speckles and low echo fields in a cardiac muscle, it is recommended to preprocess B-mode data, for instance, a median filter for noise removal and space smoothing filter for speckle removal.

Received by the entire move analyzer 185 are color velocity data from the CFM frame memory 25, mask data from the forming unit 183, and data of a ROI and a center of contraction from the CPU 43. This analyzer 185 masked the color velocity data with the mask data to determine only the region of a cardiac muscle, which prevents useless data from being taken in. Then the analyzer 185 estimates translation and rotation by using a least square method as one of cross correlation methods. The translation and/or rotation correspond to an entirely unique movement component of the present invention.

Velocity data for the least square method can obtained by one of the following procedures.

(1) Besides masking, velocity data within a ROI is used; the ROI can be placed through the operation panel.

(2) Velocity data within a ROI is culled out by appropriate means for reducing calculation.

(3) Excluded are data of a region where an angle θ between a direction of contraction toward a contraction center and a scanning beam makes approximately 90 degrees (e.g. 70 degrees<110 degrees).

In such an estimation, a center of contraction is used. One can observe a B-mode image and determine the center of a left ventricle, inputting the center of a left ventricle as data of a center of contraction through the operation panel 14. As an entire heart moves due to its beat, it is supposed that the center of a left ventricle differs frame by frame. Therefore, it is the best to determine the center of contraction for every frame using image data from the B-mode or frame memories 17 and 25.

Further, considering simplified operation will lead to another way: the center of contraction is determined for one frame at an appropriate cardiac timing selected in one cardiac cycle and the determined center is used in common to all the frames. For example, such center can be determined on a B-mode image in an end-diastole. It is also possible to determine such center of contraction on dynamic images of B-mode or color Doppler mode through a mouse etc.

The estimation by the least square method in the analyzer 185 can yield the above-mentioned parameters $\eta^*$, $\zeta^*$ for an entire move of a cardiac muscle (translation and rotation). These estimation results will then be sent to the entire move component removing unit 184, together with the original color velocity data from the frame memory 25. According to the above-said equation (23), the removing unit 184 removes those translation and (or rotation) velocity components from each of the original velocity data, calculating the true contraction velocity $U_N$. The resultant velocity data $U_N$ is returned to the frame memory 25 for replacing the stored old data with the new velocity data or for storing the new velocity data in another memory area.

In this way, two-dimensional velocity mapping data (frame data), from which the entire move has been deducted, are obtained and sent from the frame memory 25 to DSC 24. The color processing circuit 24b of the CFM DSC 24 converts the velocity data into color display data, being sent to the image data synthesizer 18.

In the color processing circuit 24b, for example, red or red-related color is given to positive contraction velocity (contraction) and blue or blue-related color to negative contraction velocity (expansion), and brightness is changed according to its magnitude. For coloring, hue, echoma and brightness can be combined in any form. Gray-scale display can also be included.

Display is carried out as follows.

(1) Raw color velocity images (without estimation mentioned above) or B-mode images are displayed in real time and data of desired frames are stored in frame memories.

(2) Then the real time images are stopped and an image of the cardiac muscle is taken from the frame memories. A calculation region and a center of contraction for each frame are determined for the above-said estimation (or, removal of entire move). After the estimation, each frame image is play back.

(3) On an image by playback, in addition to the color velocity image after the estimation, displayed together are the parameters that came out in the estimation and/or characteristic quantities of the movement resulting from an appropriate calculation (refer to FIG. 73).

According to the present embodiment, it is possible to precisely and correctly evaluate an object such as a cardiac muscle and a blood vessel wall, because of the removal of its entire movement such as translation and rotation. In addition, the displayed two-dimensional velocity map is useful in detecting and evaluating positions of abnormal contraction of a cardiac muscle.

A fourteenth embodiment will be explained according to FIG. 74. In the embodiment, a center of contraction is automatically determined.

Figure 74:
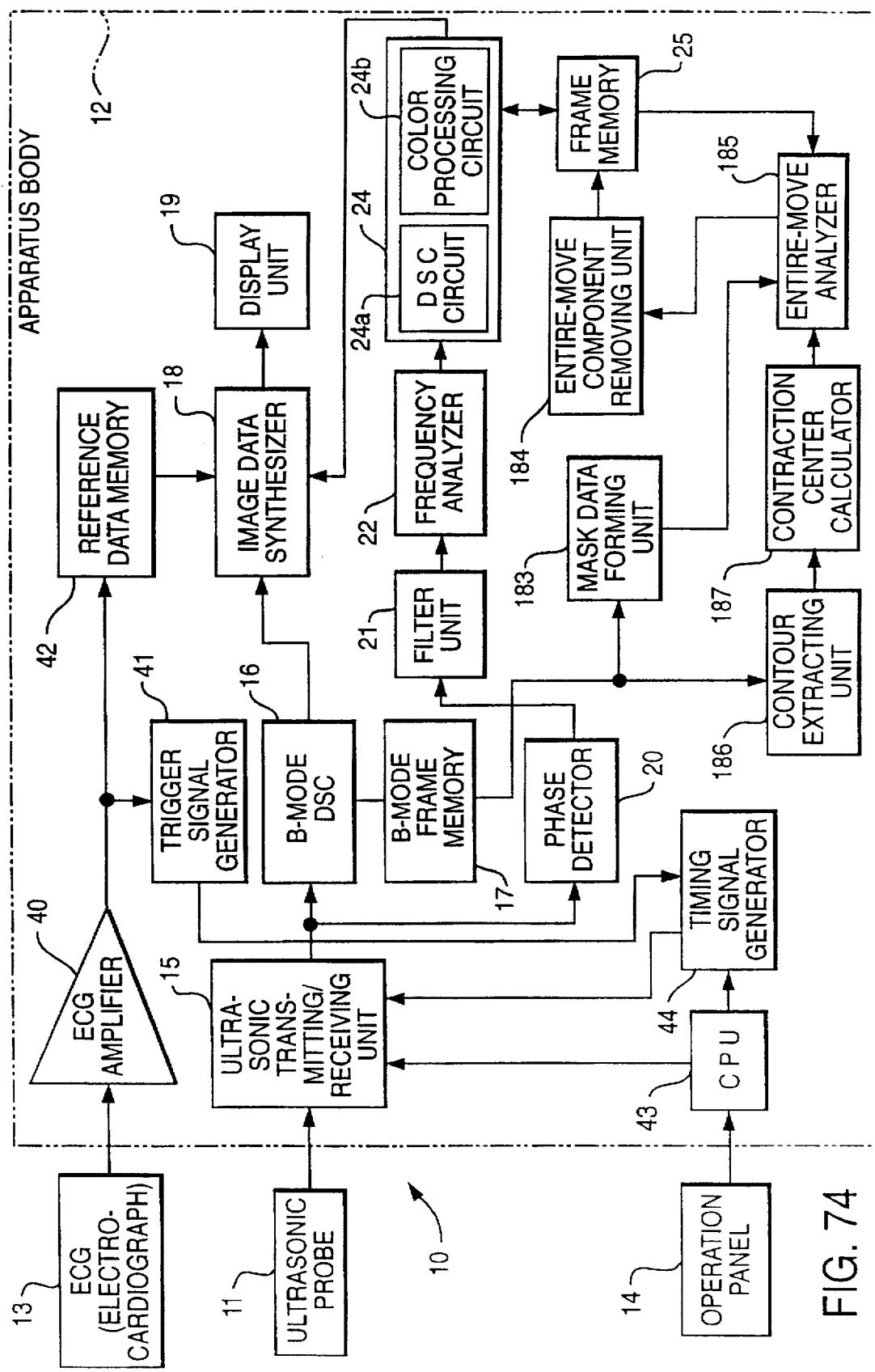
FIGS. 74 and 75 are block diagrams showing an ultrasonic diagnosis apparatus of a fourteenth and fifteenth embodiments.

In order to achieve the automatic determination, as shown in FIG. 74, a contour extracting unit 186 and contraction center calculator 187 are added to the construction of FIG. 72.

The contour extracting unit 186 is for automatically detecting the contour of a cardiac muscle from a B-mode image supplied from the B-mode frame memory 17. In detail, after removing noises and speckles, the contour of a left ventricle is detected by judging brightness level of each pixel data with a threshold. The contraction center calculator 187 is to, on the basis of the contour data, calculate the center of area of a left ventricle and to designate the center as a center of contraction.

The remaining part of FIG. 74 is the same as in FIG. 72. Therefore, in addition to the equivalent advantages to the above embodiment, automatic determination of a contraction center provides efficiency operation.

In the present embodiment, instead of the above superimposed color velocity image on the B-mode image, the velocity image can be superimposed on a contour image obtained by the contour extracting unit 186. For the entire move estimation, using the contour line makes it possible to calculate data only proximate to the endocardium or epicardium for evaluating movement.

A fifteenth embodiment will be explained according to FIG. 75. In the embodiment, movement velocities in vector quantity is given. In contrast, the previous two embodiments have detected movement velocities in ultrasonic beam directions using the widely known Doppler method.

Figure 75:
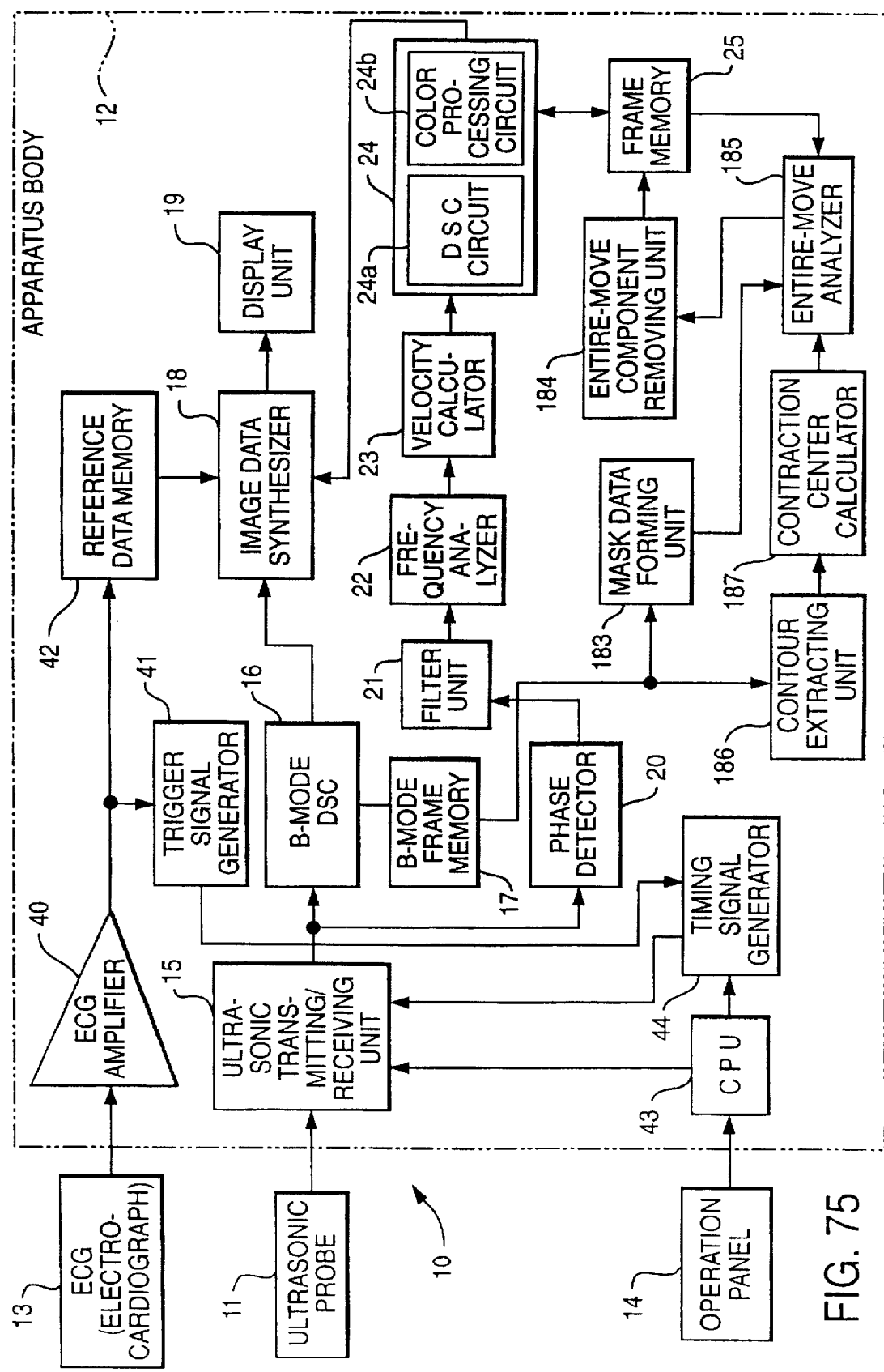

There added between the frequency analyzer 23 and DSC 24 in FIG. 75 is the velocity calculator 23 mentioned in earlier various embodiments. The velocity calculator 23 will output vector velocities, as said before, which are sent to the frame memory 25. In this case, the least square method is also applicable using the equations (24) and (25), so that it can estimate entire move of an object, that is, translation and rotation in vector quantities.

Thus, in the entire move component removing unit 184, the translation velocity vector and rotation velocity vector are deducted from the original velocity vector for every pixel, resulting velocities being sent to the DSC 24 for display.

There are variations for determining a center of contraction. That is, besides by manual and automatic setting, an appropriate plurality of regions are placed so as to include a true center which will be determined later, and a plurality of positions each lie within the regions are considered to be possible as the center. And to each region, a least square method is applied. Individual comparison of determination coefficients in calculation can decide the center of contraction for the largest one.

With regard to the estimation of the entire move, a different one from the least square method can be used; for example, if the entire move is only translation, the entire move analyzer 185 in FIG. 72 calculates a mean velocity in translation direction in an objective region or specified region and uses its result as a representative translation velocity of the object.

In the above three embodiments, the Doppler method has been used. But the detection method itself of velocity is not essential for the present invention. Another detection method such as a cross correlation method and a velocity detecting method from a B-mode image, both of which are widely known, is also preferably applicable to the present invention.

Further, the ultrasonic diagnosis apparatus in the above above embodiments can image not only a cardiac muscle but other organs and tissues such as a blood vessel wall. Also any type of ultrasonic probes can be acceptable to this apparatus.

A sixteenth embodiment will now be explained according to FIGS. 76 to 83. This embodiment to a twenty-sixth embodiment relate to improvement in display of a two-dimensional image, such as a color two-dimensional velocity image obtained in the above-said embodiments. In the sixteenth to twenty-sixth embodiments, an image displaying system of the present invention will be applied to an ultrasonic diagnosis apparatus using a Doppler technique, but it is obvious that the image displaying system is applicable to other image processing apparatus.

Figure 76:
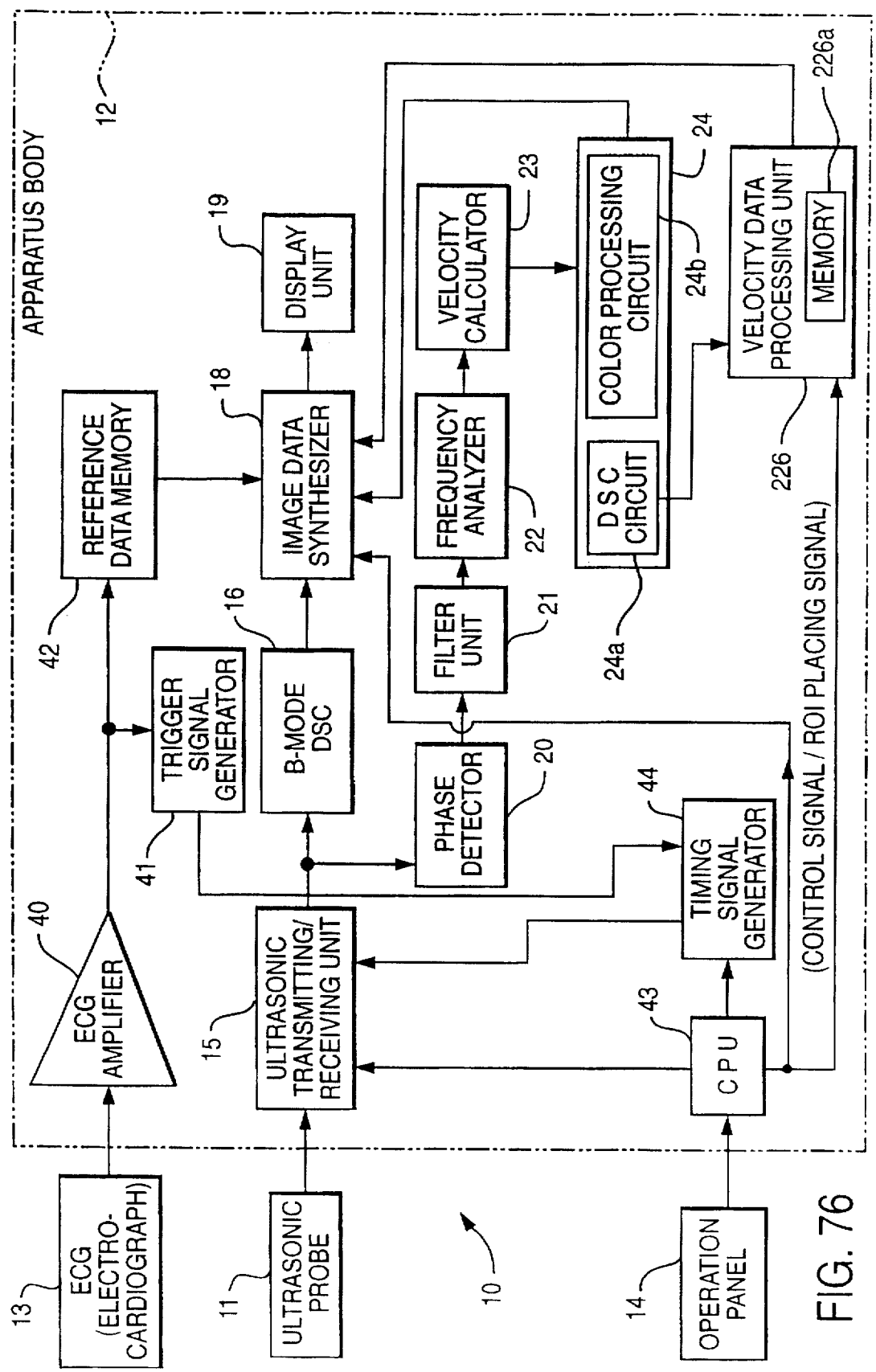
FIG. 76 is a block diagram showing an ultrasonic diagnosis apparatus of a sixteenth to twenty-sixth embodiments.

An ultrasonic diagnosis apparatus 10 according to the sixteenth embodiment will be shown in FIG. 76, in which a velocity data processing unit 226 is newly added. The diagnosis apparatus is for imaging of a cardiac muscle of a heart or a carotid arteries.

The velocity data processing unit 226, with a computer optionally performing the processing described below, processes the stored data from the frame memory of the DSC 24a into an image data consonant with the object of the present invention and outputs it to the image data synthesizer 18, in response to an instruction from the CPU 43. The processing unit 226 has a display memory 226a therein used for coordinate conversion described below.

Then, an explanation will be given as to the velocity data processing unit 226 according to FIGS. 76 to 83. With a color image of a cardiac ventricle displayed, the velocity data processing unit 226 initiates its processing shown in FIG. 77, in response to a control signal from the CPU 43.

Figure 77:
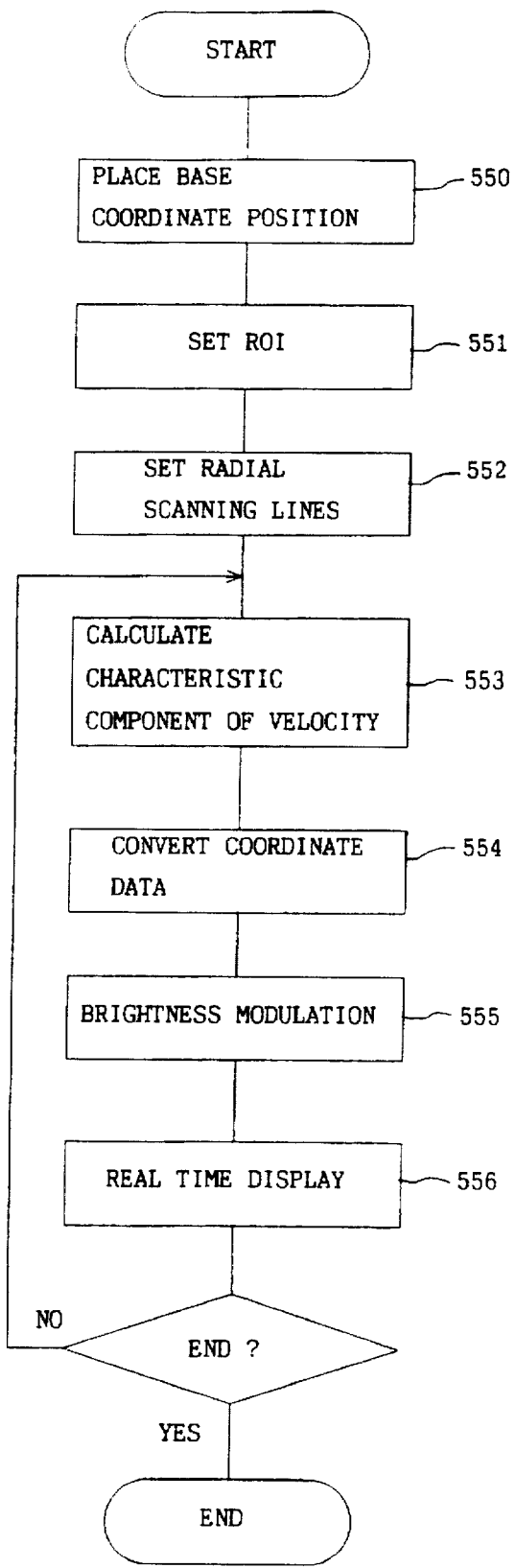
FIG. 77 is a flowchart showing a process of velocity data in the sixteenth embodiment.
Figure 78:
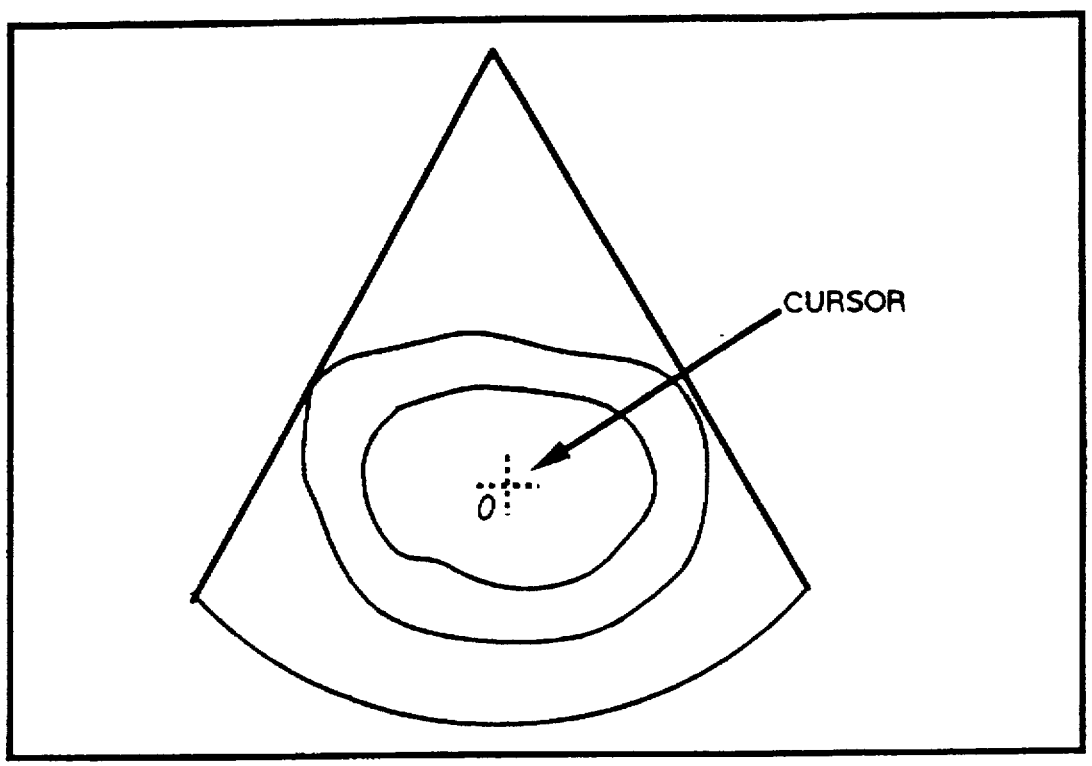
FIG. 78 explains placing of a basic coordinate point in the sixteenth embodiment.

At a step 550 in FIG. 77, an operator transfers a cursor on a heart image along its minor axes (B-mode image) on which a color Doppler image is superimposed, using a track ball on the operation panel 14, for example, as shown in FIG. 78. And a finally designated cursor position is placed as a manually set base coordinate point O(Xo, Yo). In this way, placed as the base coordinate point O is a position generally considered to be a center of gravity for a cardiac muscle on the display.

This base coordinate point O may be placed by inputting numerals through a keyboard, a coordinate value, depth and a distance in an azimuth direction.

At a step 551, set is a ROI (region of interest) based on the aforementioned base coordinate point O. That is, the velocity data processing unit 226 sets a circular ROI with a radius r centering on the based coordinate point O, as illustrated in FIG. 79. An operator can arbitrarily set the value of this radius r with a track ball, keyboard, and so forth on the operation panel 14.

At a step 552, set on the display image are scanning lines 1,2, . . . ,n each of which extends radially from the base coordinate point O(Xo, Yo), spacing equally to each other with an arbitrary angle θ which divides equally the whole angle 0–360 degrees around the base coordinate point O. An operator can optionally designate the division number of scanning line 1, . . . ,n, i.e. the angle θ when processing the velocity data. It also can prehold the angle θ as a fixed data in the program of the velocity data processing unit 226.

Figure 80:
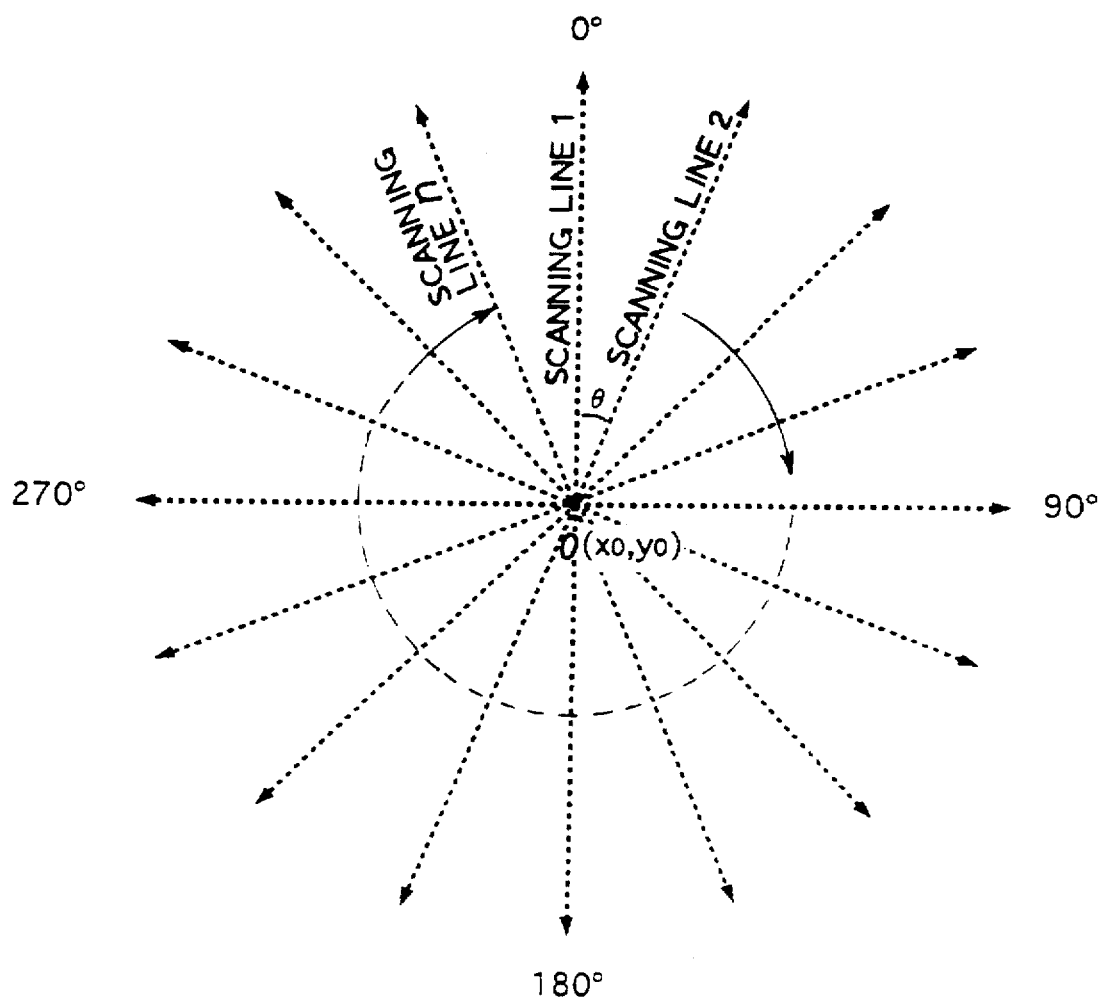
FIG. 80 shows setting of radial scanning lines in the sixteenth embodiment.
Figure 82:
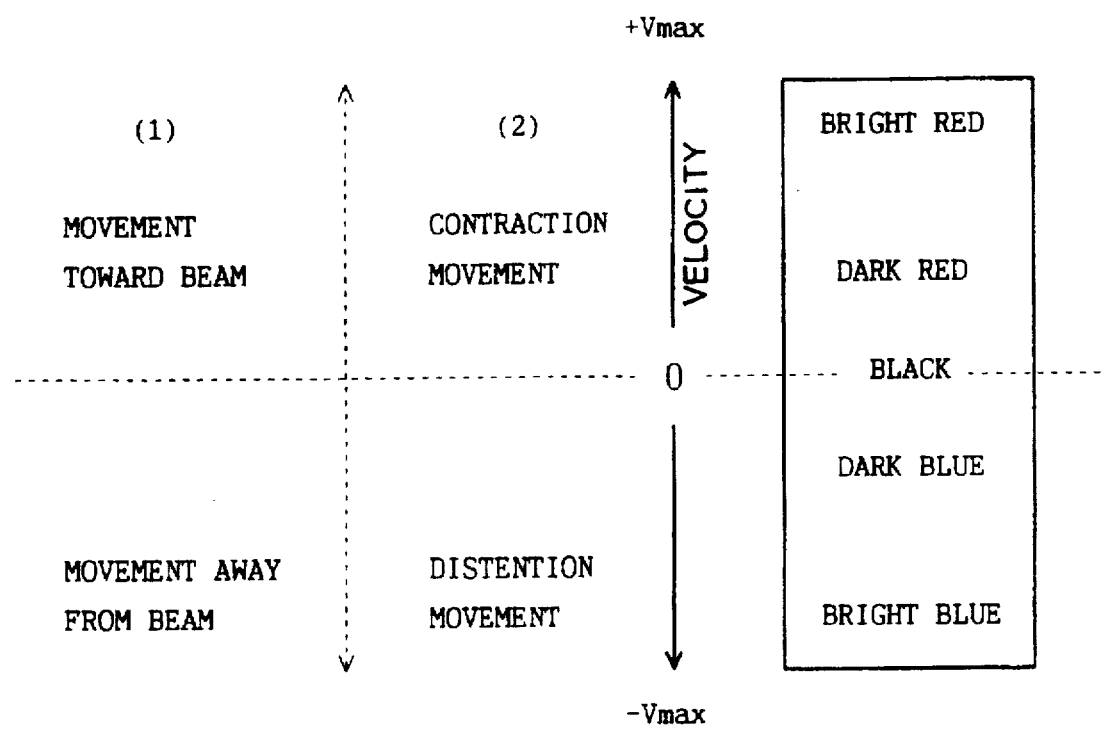
FIG. 82 shows brightness modulation in the sixteenth embodiment.

Then at a step 553, reading from the DSC circuit 24a the absolute velocity data of the cardiac muscle on the radial scanning lines 1, . . . ,n, calculated is a velocity information (characteristic component of the movement) of a mean (e.g. simple arithmetic mean) of an absolute velocity of a cardiac muscle, maximum value, minimum value, median, etc. for each of scanning lines 1, . . . ,n(cf. FIG. 80). The calculation here is executed only within a linear range (calculation region) from the origin of the base coordinate point O(Xo, Yo) for each of the scanning lines, 1, . . . ,n to a destination designated by the ROI, thus excluding wasteful operation.

At a step 554, written into the display memory 226a are the results of calculation executed above. These results of calculation are the values of the arithmetic mean of the cardiac muscle absolute velocity, which are the values for a circular section centering on the base coordinate point O(Xo, Yo). FIG. 81 schematically shows the one-dimensional display memory 226a with an array n. The results of calculation performed for each of the scanning lines 1, . . . ,n are converted into the data of display memory 226a. With this procedure, converted through coordinate conversion into a linear data array are the results of calculation (mean, etc.) as information for the circular section.

Then at a step 555, the converted data array is subjected to brightness modulation corresponding to the magnitude of the velocity. The way of converting the data array to a brightness information can be divided into two; (i) the way of converting the magnitude of velocity (absolute value) only, and (ii) the way of converting the direction of movement and the magnitude of velocity. As the way (i), there are ways such as (ia) ways of changing brightness with monochrome corresponding to the magnitude of velocity, and (ib) changing color corresponding to the magnitude of velocity. On the other hand, as the way (ii), there is a way in which a direction of movement is shown with color (a movement toward an ultrasonic beam is shown with red and a movement away from an ultrasonic beam with blue, or as to a cardiac muscle, a contraction movement is shown with red and distension movement with blue) and the velocity magnitude is shown with brightness, as pictorially illustrated in FIG. 82.

This brightness modulation can be carried out parallel to the coordinate conversion (writing into a memory) of each scanning line at the step 554.

Figure 83:
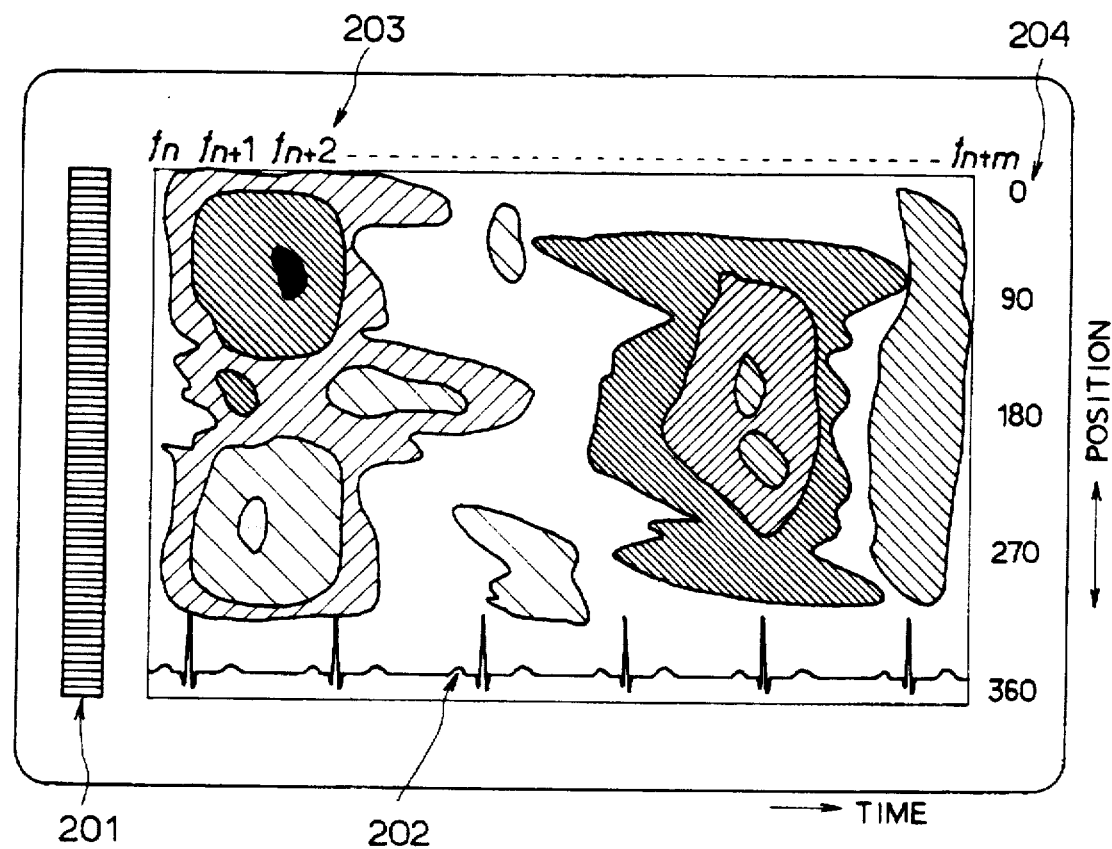
FIG. 83 is an image showing a characteristic component of movement vs. elapsed times (frame numbers) in the sixteenth embodiment.

Further at a step 556, the image data written into the display memory 226a is transmitted to the display unit 19 via the image data synthesizer 18 and is displayed in real time. There has been provided the M-mode method as a conventional measurement, in which a real-time display is made, sweeping transversely on the display the brightness change of every frame (toward a time direction) at a position of the M-mode marker, and representing along the longitudinal axis the brightness modulation data of the characteristic component (mean, etc) of the movement calculated radially, centering on the base coordinate point O(Xo, Yo). The notation in FIG. 83 is as follows: The reference numeral 201 is a bar representing color and brightness for a direction and a magnitude of movement velocity of an organ to be measured such as cardiac muscle, etc. The reference numeral 202 is a curve for ECG representation (The ECG level and the position of the curve on the display is changeable.). The reference numeral 203 is an array of codes representing that the frames from the (fn)th one to the (fn+m)th one are swept towards a transverse direction in real time (it actually is not shown on the display an operator watches). The reference numeral 204 is an annotation representing a position or angle of the radial scanning lines set centering on the base coordinate point O(Xo, Yo).

After the step 556, the processing in the velocity data processing unit 226 will be returned to the step 53 and the foregoing processing is repeated in real time.

In this way, the characteristic component (mean velocity, for instance) of the movement of a cardiac muscle for every sampling volume is calculated along the scanning lines 1, . . . ,n extending from the base coordinate point O(Xo, Yo) arbitrarily placed by the operator. The circular characteristic-component information data is converted into a linear data array and is subjected to brightness modulation. This linear data array subjected to brightness modulation is swept in real time towards a transverse axis (time axis) on the display. Consequently, the display as shown in FIG. 83 is achieved. As seen from this figure, one can easily understand how large is the velocity of each section of the cardiac muscle (i.e. the position of scanning lines) at a certain time. For instance, one can easily observe that a certain section (i.e. a certain position in the longitudinal axis on the display) has a velocity smaller than that of the others.

A seventeenth to twenty-sixth embodiments of the present invention partially different from the previous example will be explained based on FIGS. 84 to 95.

A seventeenth embodiment is explained, referring to FIG. 84. This example relates to another way of placing the base coordinate point O. The velocity data processing unit 226 performs the following processing at the step 550 when it runs a series of processing illustrated in FIG. 77. That is, first an operator places a several coordinate points P1, . . . ,P1 at the peripheries of an organ such as cardiac muscle regarding the image currently displayed, using a track ball on the operation panel 14. Then, the velocity data processing unit 226 calculates a center of gravity of polygon which takes the coordinate points P1, . . . ,P1 as its vertex. It also designates the gravity center position as the base coordinate point O(Xo, Yo). This gravity center position is determined through calculation with the equations given below.

$$X_0 = \frac{1}{6S} \sum_{i=1}^{m} (X_i Y_i - X_{i+1} Y_i)(X_i + X_{i+1})$$

$$Y_0 = \frac{1}{6S} \sum_{i=1}^{m} (X_i Y_i - X_{i+1} Y_i)(Y_i + Y_{i+1})$$

where m is the number of contour points array inputted, Xi and Yi (i=1,2, . . . ,m) are the coordinates of the base contour points array, and Xm+1=X1, Ym+1=Y1. Furthermore, S is an area of polygon whose vertexes are the contour points and given by an equation below.

$$S = \frac{1}{2} \sum_{i=0}^{m} (X_i Y_{i+1} - X_{i+1} Y_i)$$

Figure 85:
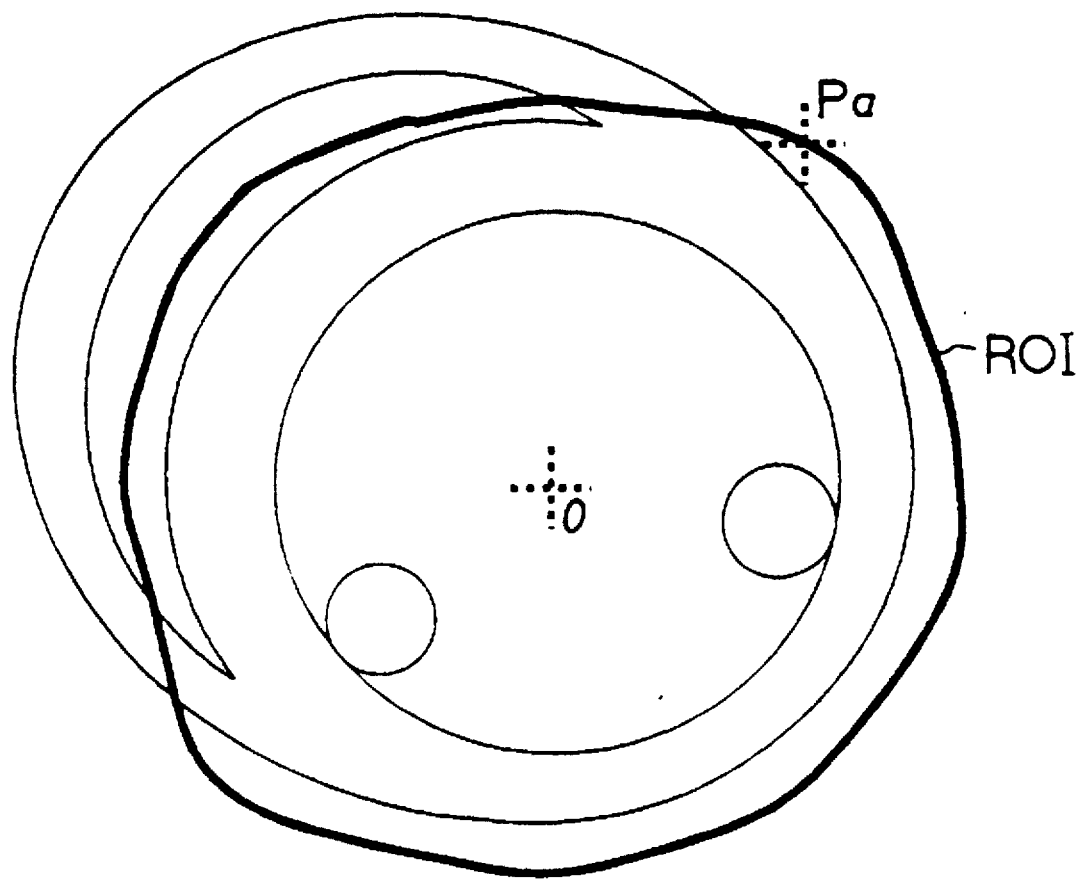
FIG. 85 explains placing of a ROI in the eighteenth embodiment.

An eighteenth embodiment is explained, referring to FIG. 85. This example relates to another way of setting the ROI. The velocity data processing unit 226 performs the following processing at the step 551 when it runs a series of processing illustrated in FIG. 77. That is, first an operator draws an arbitrary locus including an arbitrary coordinate points Pa and confining an endocardium, using a track ball. Then, the velocity data processing unit 226 sets it as a designated ROI.

Figure 86:
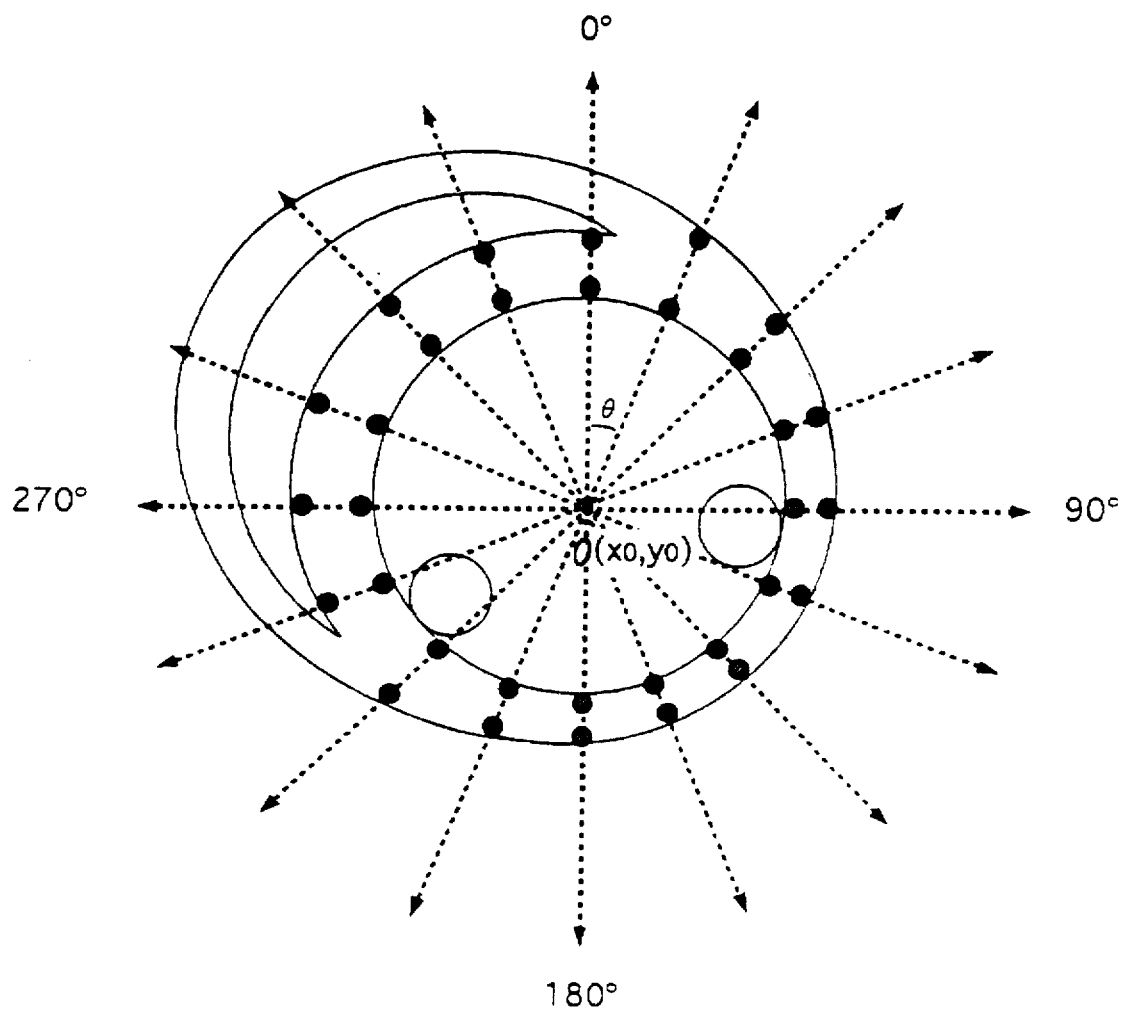
FIG. 86 shows calculation of a characteristic component of movement for radial scanning lines in the nineteenth embodiment.

A nineteenth embodiment is explained, referring to FIG. 86. This example relates to another way of calculating the characteristic component of movement. The velocity data processing unit 226 performs the following processing at the step 553 when it runs a series of processing illustrated in FIG. 77. That is, first it detects the position of endocardium and epicardium for every scanning line centering on the base coordinate point O(Xo, Yo), identifying a monochromatic image value with a predetermined threshold, for example. It subsequently calculates a mean, maximum value, minimum value, median, etc. of the absolute velocity only for the positions of endocardium and epicardium and determines an appropriate characteristic component (mean, for example). It does not calculate concerning the sections except for the positions of endocardium and epicardium so as to expedite the processing.

A twentieth embodiment is explained, referring to FIG. 87. This example relates to still another way of calculating the characteristic component of movement as in the nineteenth example. The velocity data processing unit 226 performs the following processing at the step 553 when it runs a series of processing illustrated in FIG. 77. That is, first it calculates a mean, maximum value, minimum value, median, etc. of the velocity information for every scanning line centering on the base coordinate point O(Xo, Yo). It further puts together into one group a preselected plurality of adjacent scanning lines and determines a representative of characteristic component (a mean, maximum value, minimum value, median, etc. of the velocity) for every group. This representative eventually becomes a characteristic component representing a radial calculation range 1,2, . . . as shown in FIG. 87. Here, the coordinate conversion and brightness modulation are carried out as in the previous sixteenth example. With these procedures, one can divide a thick and circular section centering on the base coordinate point O(Xo, Yo), into the predetermined number of blocks and can visually grasp the movement of the individual block.

Figure 88:
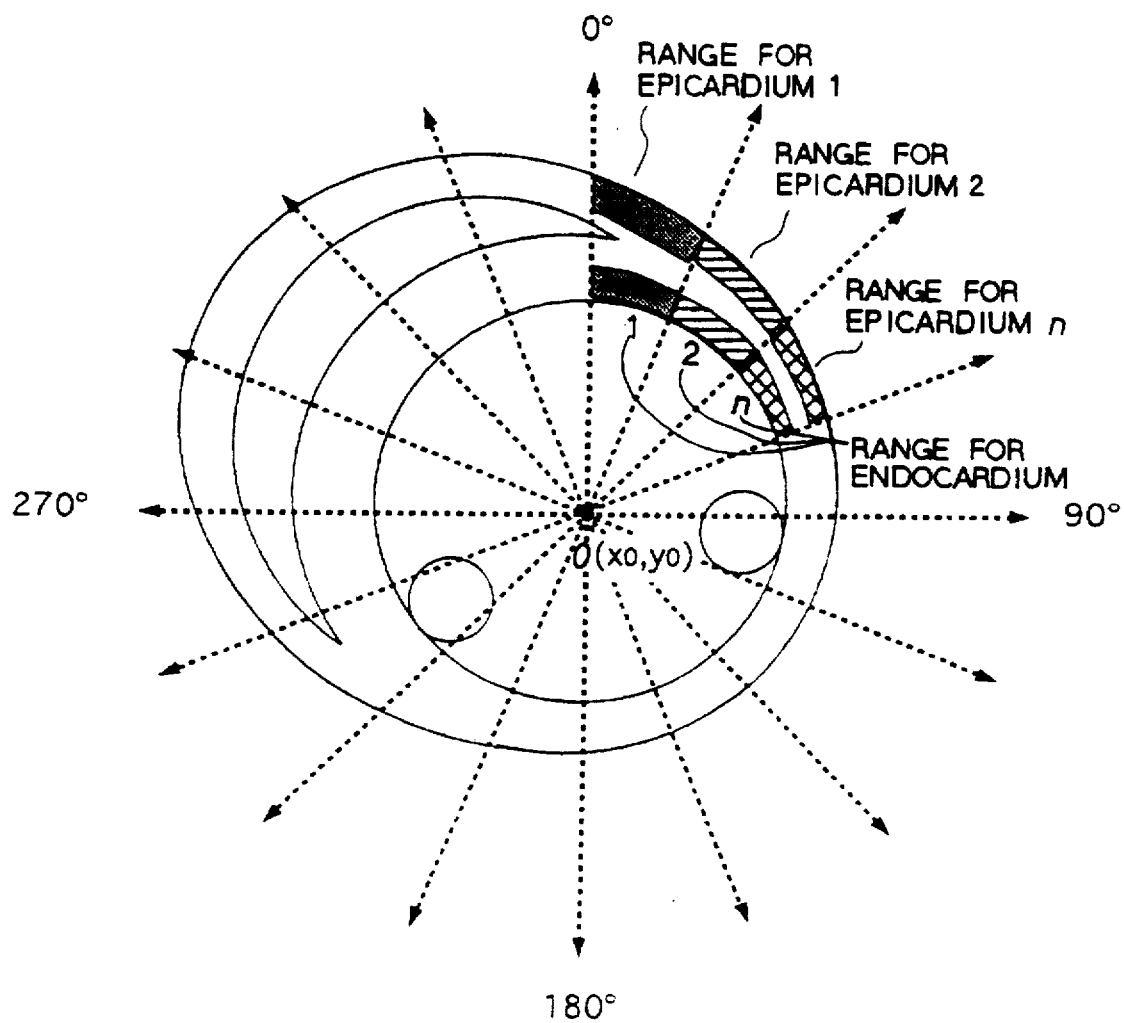
Figure 89:
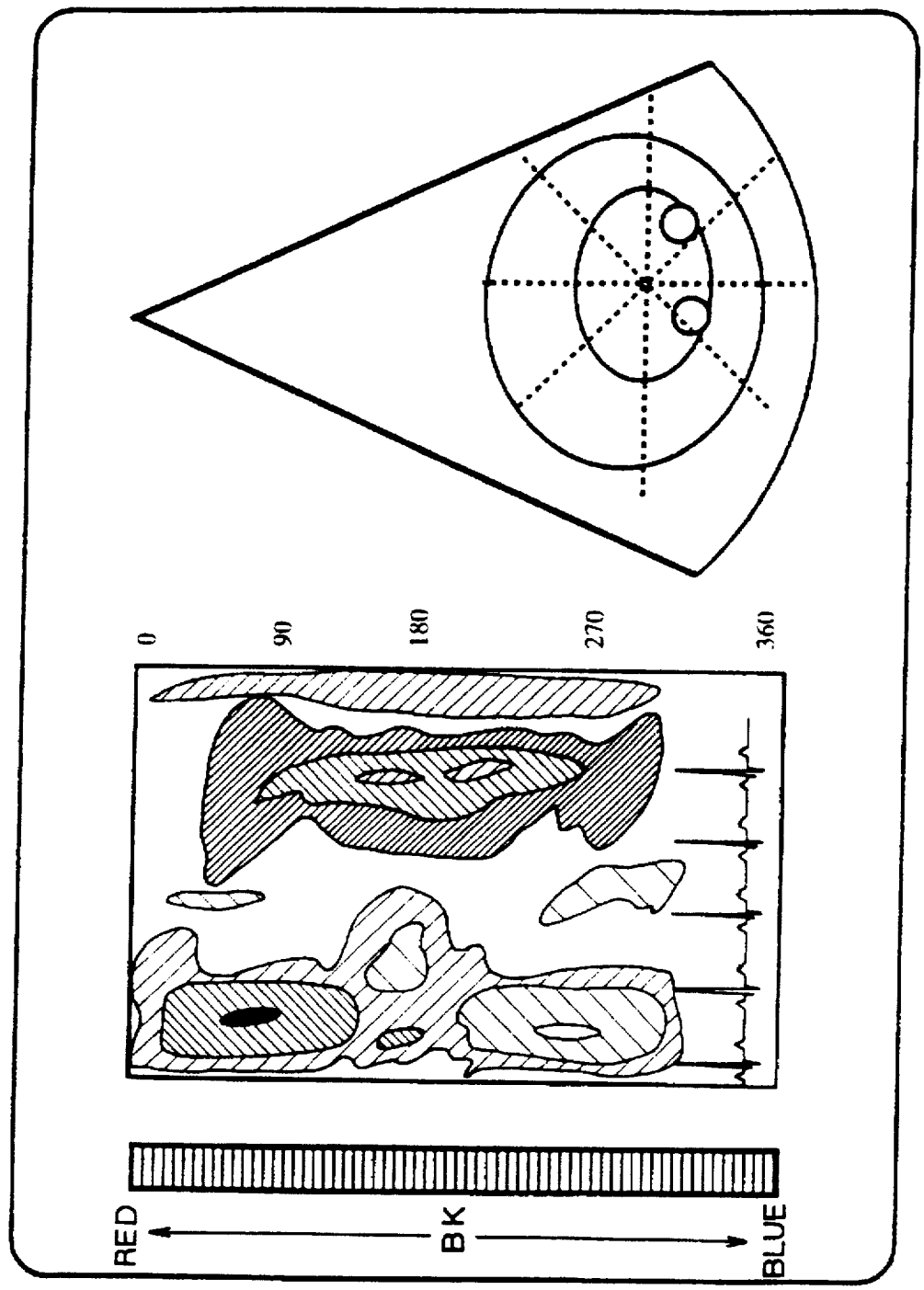
FIGS. 89 and 90 are image examples in the twenty-second and twenty-third embodiments.

A twenty-first embodiment is explained, referring to FIG. 88. This example relates to still another way of calculating the characteristic component of movement as in the previous two examples. The velocity data processing unit 226 performs the following processing at the step 553 when it runs a series of processing illustrated in FIG. 77. That is, first on a heart image along its minor axis, it detects the position of endocardium and epicardium for every scanning line centering on the base coordinate point O (Xo, Yo), with a predetermined threshold processing, for example. It subsequently calculates a mean, maximum value, minimum value, median, etc. of the absolute velocity only for the positions of endocardium and epicardium and determines an appropriate characteristic component (mean, for example). It does not calculate concerning the sections except for the positions of endocardium and epicardium. It further puts together into one group a preselected plurality of adjacent scanning lines and determines a representative of characteristic component for every group and for each position of endocardium and epicardium. This representative of each scanning line group is subjected to the coordinate conversion and brightness modulation as in the sixteenth example. With these procedures, the fast calculation becomes possible and one can divide a circular section centering on the base coordinate point O(Xo, Yo) into the predetermined number of blocks and can visually grasp the movement of the individual block.

Figure 90:
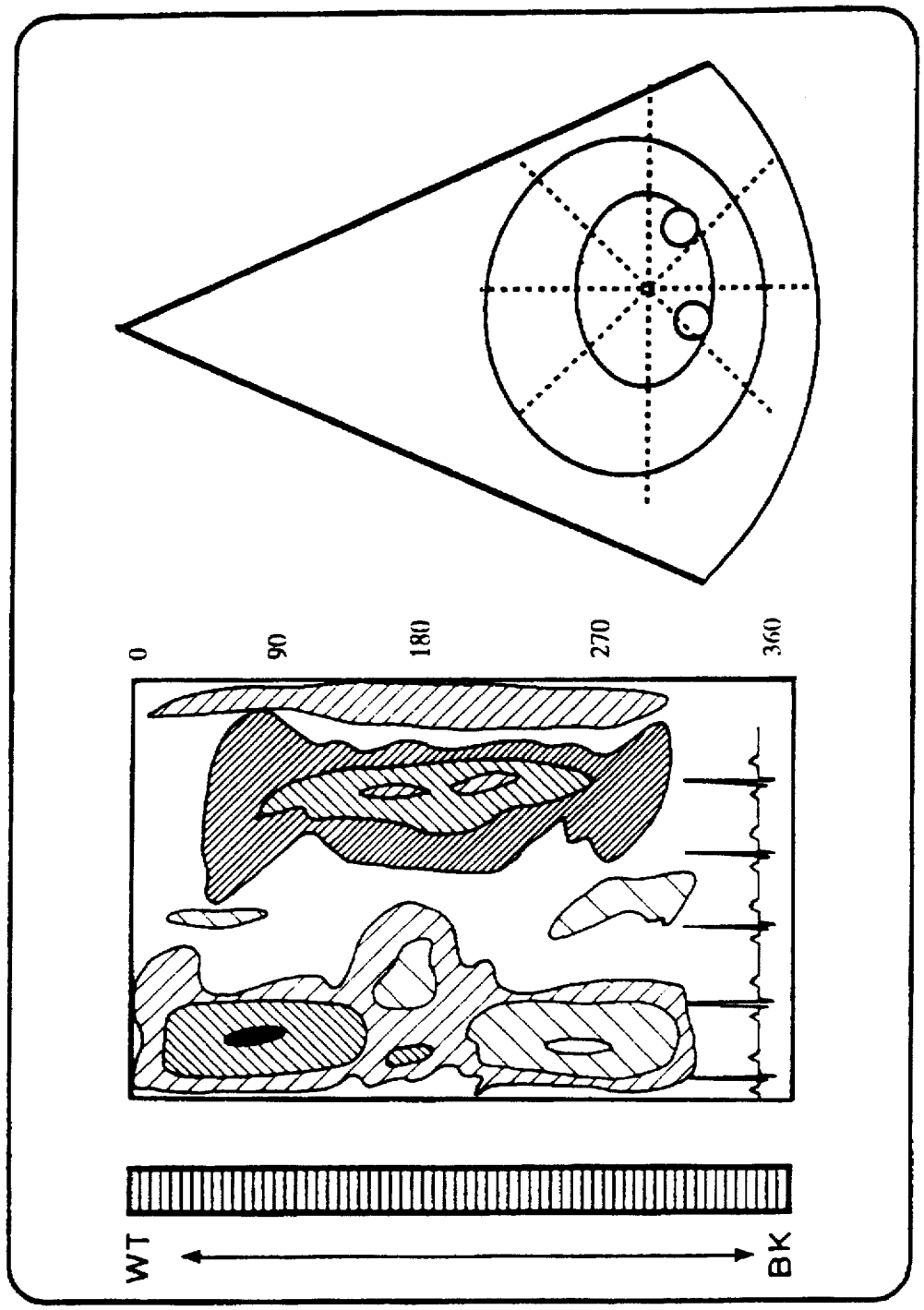
Figure 91:
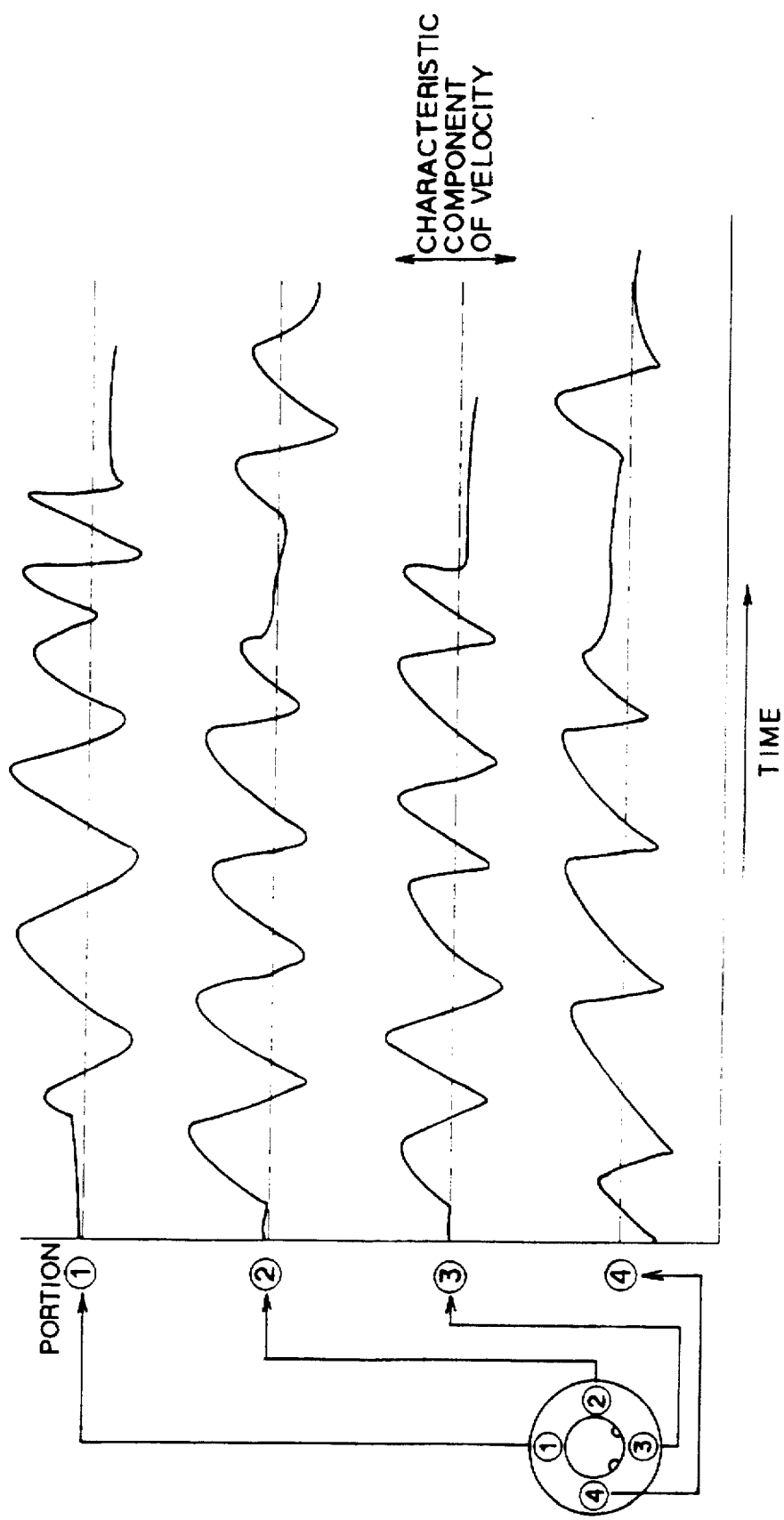
FIGS. 91A and 91B explain a characteristic component of movement for radial portions in the twenty-fourth and twenty-third embodiments.

A twenty-second and twenty-third embodiments are explained, referring to FIGS. 90, 91A, and 91B. These examples are accomplished with a display instruction at the step 556 in FIG. 77 and the processings at the velocity data operating unit 226 and at the image data synthesizer 18. The example of display shown in FIG. 90 related to the twenty-second example simultaneously represents a B-mode tomographic image and/or color Doppler image along with a time-chaging image of the characteristic component above-identified in FIG. 83. On the other hand, the example of display shown in FIGS. 91A and 91B related to the twenty-third example represents a time-changing image of the characteristic component with a gray scale (monochromatic brightness modulating image), employing a monochromatic brightness modulation in the velocity data processing unit 226 instead of the color-base brightness modulation as above-mentioned. This display further simultaneously can represent a B-mode tomographic image and/or color Doppler image.

As explained above, the present invention provides a diagnosing apparatus much effective than the conventional ones, in which one can easily judge a time difference between a normal section and an abnormal section at the systole and diastole in the myocardial ischemia, myocardial disease, etc. or the displacements and velocity differences of endocardium and epicardium.

The diagnosis explained in the above examples are also effective to a carotid artery or other moving organs, thus being applicable to a wide range of diseases. In addition, since there is no need to impose an electric stimulation or exercise load to a heart, eliminated is a patient's disgust.

Furthermore, the instance with a more developed idea will be explained referring to the following twenty-fourth to twenty-sixth examples.

Figure 92:
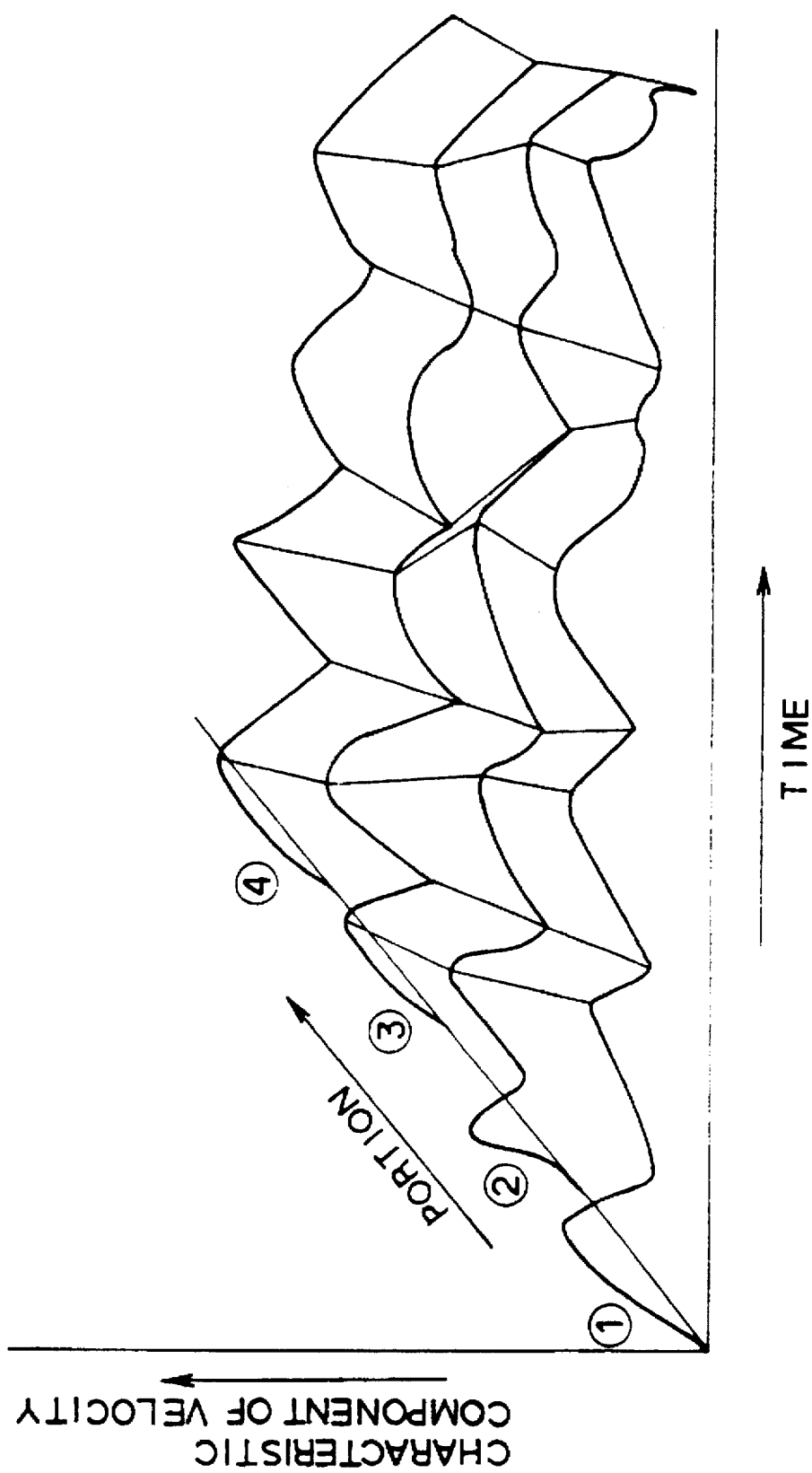
FIG. 92 is an image of 3-D wire frame display in the twenty-fourth embodiment.

A twenty-fourth embodiment is explained, referring to FIGS. 91A, 91B, and 92. The way of display is improved in this example. As mentioned above, each of a radially arranged section is set (the radially extending scanning lines or the radially arranged blocks defined by these scanning lines: the number of sections in FIG. 91A)=4: exemplified as 1–4, and the movement characteristic component for each of these sections are determined as in FIG. 91B. The velocity data processing unit 226 reforms these characteristic components in real time into the data capable of three-dimensional wire frame display and transmits these image data to the display unit 19. Thus, as shown in FIG. 92, displayed is the image with three-dimensional wire frame display (in the same figure, the depth direction shows a position of each section). Therefore, one can easily and visually understand the movement with this wire frame display.

Figures 93A, 93B:
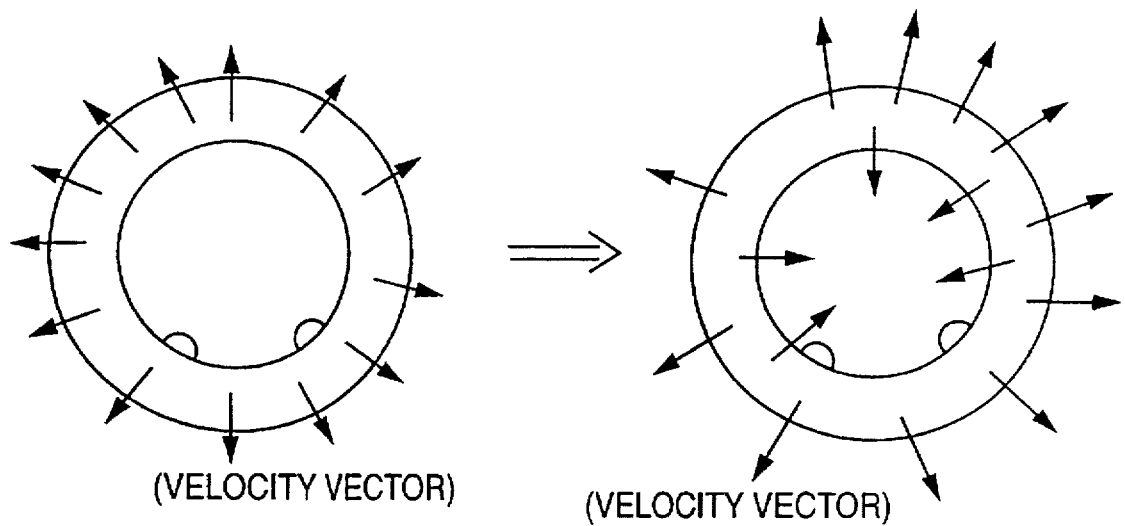
FIGS. 93A and 93B explain velocity vectors in the twenty-fifth embodiment.
Figure 94:
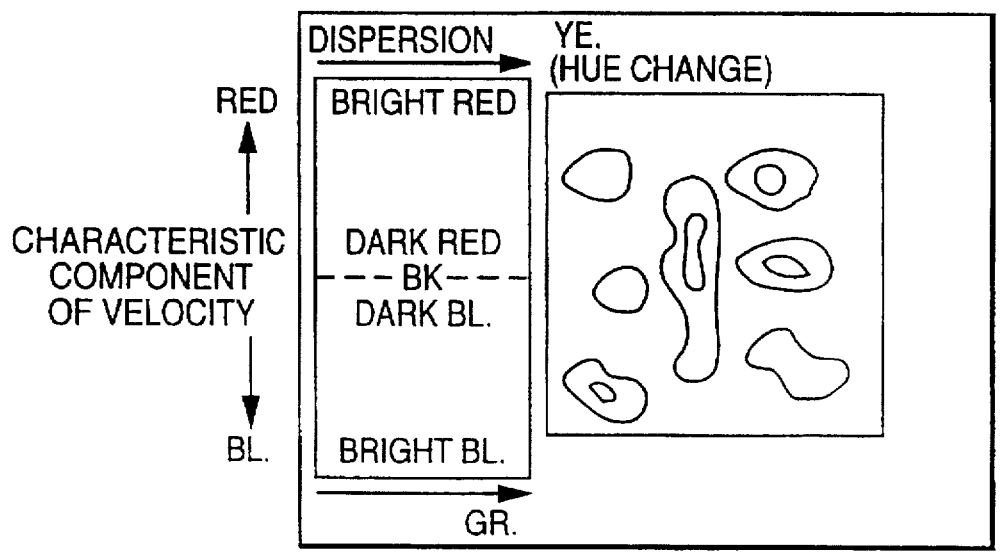
FIG. 94 is an image taking velocity dispersion into account me display in the twenty-fifth embodiment.

A twenty-fifth embodiment Is explained, referring to FIGS. 93A, 93B and 94. Considered is a variation of the velocity vector as well as a component related to the movement velocity itself as the above-mentioned characteristic component. The heart not only repeats a systole and diastole simultaneously at each time as shown in FIG. 93A but shows a movement at a certain section reverse to a whole motion, thus disturbing a motion velocity vector with generating the complicated movement. Hence, the velocity data processing unit 226 not only colors the calculated characteristic component such as a mean velocity, but calculates a variation of the movement velocity vector for every section, colors it differently (e.g. with yellow or green) and displays these image data at the display unit 19 (cf. FIG. 94). Consequently, a radial section with a greater variation, for example is displayed with a mean velocity using red or blue having a color tone greater than that of yellow or green. Therefore, one can obtain much movement information on a single display with this excellent diagnosing apparatus.

Figure 95:
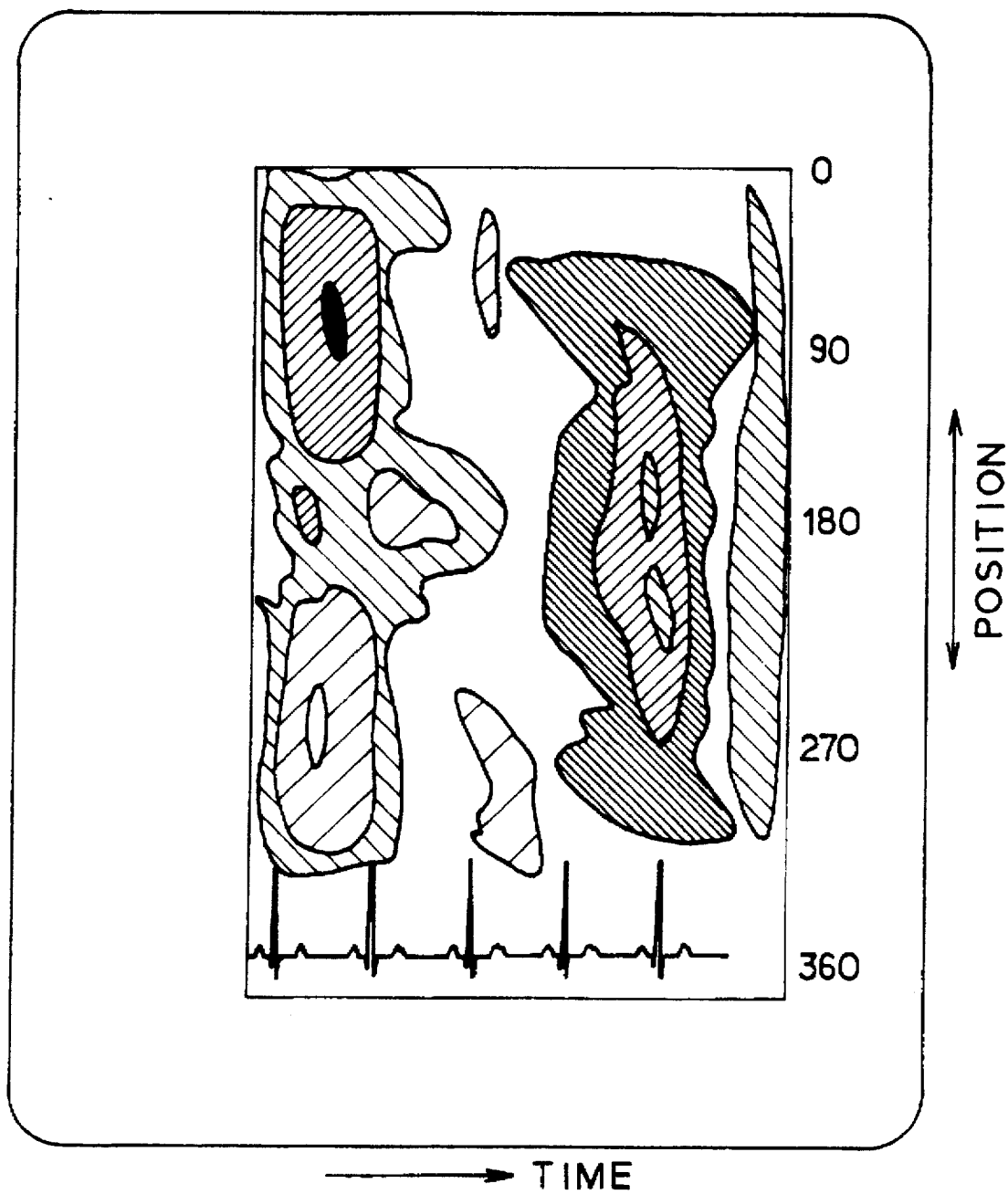
FIG. 95 is an acceleration vs. elapsed times in the twenty-sixth embodiment.

A twenty-sixth embodiment is explained, referring to FIG. 95. Considered as a characteristic component is a variation of the acceleration of the movement in each radial section. The velocity data processing unit 226 calculates a mean movement velocity of the each section (the radially extending scanning line section or radially arranged block section) on the heart minor axis. Then, it determines a velocity difference of each section (acceleration of the movement) between the mean velocity of that section and the mean velocity of that one or a few frames ago (the velocity of which is stored in memory and renewed successively after processing). This acceleration is a characteristic component in this example and is calculated in a step corresponding the step 553 in the flow chart of FIG. 77. This acceleration is subjected to brightness modulation concerning monochrome or a predetermined coloring, as in the above case of the characteristic component of the mean velocity. Consequently, obtained is the two-dimentional display as shown in FIG. 95, in which the transverse axis represents time, the longitudinal axis represents a radial calculation POSITION and the magnitude of the acceleration is represented with a degree of brightness.

According to the present apparatus, when the organs are normal, the brightness is low over the whole two-dimensional modulated image without a local part of large acceleration. However, when there is an abnormal portion, such portion is represented with a locally high brightness. Thus, since the acceleration is used as a characteristic component representing an organ movement, enlarging the selective range of the characteristic component, one is able to view the organ movement diversifiedly and make an overall diagnosis.

What I claim is:

1. An image displaying system in which data of two-dimensionally mapped velocities of movement of a tissue in a cross section of an object being examined are provided frame by frame, the system comprising:

means for specifying a point in the data of two-dimensionally mapped velocities of each frame and for providing parameters denoting a plurality of angular positions extending radially from said specified point in said data of two-dimensionally mapped velocities;

means for converting frame by frame the data of two-dimensionally mapped velocities of each frame into image data of movement of the tissue in accordance with said specified point and said parameters denoting said radial lines; and means for displaying a plurality of image data produced over the plurality of frames as a more than one-dimensional image including two axes, one axis corresponding to an elapsing-time order over the plurality of frames and the other axis representing values of the image data along at least one of said radial lines extending from said specified point.

2. The image displaying system of claim 1, further comprising:

means for setting a region to be calculated in the data of the two-dimensionally mapped velocities of each frame in accordance with the specified point; and means for calculating frame by frame data of a characteristic component of movement of the tissue from the data of two-dimensionally mapped velocities within the region set to be calculated, the data of the characteristic component being the image data and being provided to the converting means.

3. The ultrasonic diagnosis apparatus of claim 2, wherein the characteristic-component calculating means is means for calculating, as the data of the characteristic component, one of data of an average velocity, maximum velocity and minimum velocity of movement of the tissue within the region to be calculated on the basis of the data of two-dimensionally mapped velocities.

4. The ultrasonic diagnosis apparatus of claim 2, wherein the characteristic-component calculating means has a means for calculating the data of the characteristic component added to which are data of variation of velocities of movement of the tissue on the basis of the data of two-dimensionally mapped velocities within the region to be calculated.

5. The ultrasonic diagnosis apparatus of claim 2, wherein the characteristic-component calculating means is means for calculating, as the data of the characteristic component, data of acceleration movement of the tissue in the region to be calculated on the basis of the data of two-dimensionally mapped velocities.

6. The ultrasonic diagnosis apparatus of claim 2, wherein the region to be calculated is formed by a predetermined scope set in association with each of the plurality of angular positions.

7. The ultrasonic diagnosis apparatus of claim 2, wherein the region to be calculated is formed by a radially-extending and ring-like range set in association with the plurality of angular positions and positioned around the specified point.

8. An ultrasonic diagnosis apparatus having a scanning means for receiving an echo signal via an ultrasonic probe by ultrasonically and frame by frame scanning,
a cross section of an object being examined, the cross section including a tissue, the apparatus comprising:
means for calculating frame by frame data of two-dimensionally mapped velocities of movement of the tissue in the cross section on the basis of the echo signal;
means for setting a base coordinate point in the data of two-dimensionally mapped velocities;
means for setting a region to be calculated in association with a plurality of lines extending radially from the base coordinate point the in the data of two-dimensionally mapped velocities of each frame;
means for calculating frame by frame data of a characteristic component of movement of the tissue from the data of two-dimensionally mapped velocities within the region to be calculated;
means for converting frame by frame the data of the characteristic component of movement into a plurality of image data of movement of the tissue in accordance with parameters denoting a plurality of angular positions extending radially from the base coordinate point within the region in the data of two-dimensionally mapped velocities; and
means for displaying the image data produced over the plurality of frames as a more than one-dimensional image including two axes, one axis corresponding to an elapsing-time order over the plurality of frames and the other axis representing values of the image data.

9. The ultrasonic diagnosis apparatus of claim 8, wherein the displaying means comprises means for computing a magnitude and a direction of movement of each of the image data of movement, and means for performing not only brightness modulation for each of the image data in compliance with the magnitude but also assignment of different color tones to each of the image data depending on whether the direction is toward or away from the base coordinate point.

10. The ultrasonic diagnosis apparatus of claim 8, wherein the displaying means comprises means for computing a magnitude and a direction of movement of each of the image data, and means for converting each of the image data component moving to the base coordinate point and the velocity component moving in to either one of gray scale display data or color display data depending on whether the direction is toward or away from the base coordinate point.

11. The ultrasonic diagnosis apparatus of claim 8, wherein the displaying means comprises means for computing a magnitude and a direction of movement of each of the image data of movement, and means for assigning different color tones to each of the image data depending on whether the direction is toward or away from the ultrasonic probe of the scanning means.

12. The ultrasonic diagnosis apparatus of claim 8, wherein the displaying means comprise means for computing a magnitude and a direction of movement of each of the image data of movement, and means for converting each of the image data to either one of gray scale display data or color display data depending on whether the direction is toward or away from the ultrasonic probe.

13. The ultrasonic diagnosis apparatus of claim 8, wherein the displaying means comprise means for computing a magnitude and a direction of movement of each of the image data of movement, and means for forming wire frame display data from the image data of movement.

14. The ultrasonic diagnosis apparatus of claim 13, wherein the wire frame display data consists of a three-dimensional image data including a first axis corresponding to the elapsing-time order over the plurality of frames, a second axis representing values of the image data, and a third axis representing radially-located examination portions reflecting the radially extended lines.

15. The ultrasonic diagnosis apparatus of claim 8, wherein the region to be calculated is formed by a predetermined scope set on each of the plurality of the lines.

16. The ultrasonic diagnosis apparatus of claim 8, wherein the region to be calculated is formed by a radially-extending and ring-like range set on the plurality of lines and positioned around the base coordinate point.

17. The ultrasonic diagnosis apparatus of claim 16, wherein the base coordinate point setting means has a means for enabling the base coordinate point to be set in either one of an automatic setting mode or a manual setting mode.

18. The ultrasonic diagnosis apparatus of claim 17, wherein the region setting means is provided with a means for designating a region of interest around the base coordinate point with centering on the base coordinate point, the region of interest corresponding to the region to be calculated.

19. The ultrasonic diagnosis apparatus of claim 18, wherein the region of interest designating means is a means that designates a circular region of interest with an arbitrary radius as the region to be calculated.

20. The ultrasonic diagnosis apparatus of claim 19, wherein the circular region of interest includes two concentric circles sharing the base coordinate point as a co-center and the region to be calculated has its radial direction designated by the two circles.

21. The ultrasonic diagnosis apparatus of claim 18, wherein the region of interest designating means is a means that designates a region of interest with an arbitrary shape formed by connecting a plurality of points positioned in the data of the two-dimensionally mapped velocities.

22. The ultrasonic diagnosis apparatus of claim 8, wherein the characteristic-component calculating means is means for calculating, as the data of the characteristic component, one of data of an average velocity, maximum velocity and minimum velocity of movement of the tissue within the region to be calculated on the basis of the data of two-dimensionally mapped velocities.

23. The ultrasonic diagnosis apparatus of claim 8, wherein the characteristic-component calculating means has a means for calculating the data of the characteristic component added to which are data of variation of velocities of movement of the tissue on the basis of the data of two-dimensionally mapped velocities within the region to be calculated.

24. The ultrasonic diagnosis apparatus of claim 8, wherein the characteristic-component calculating means is means for calculating, as the data of the characteristic component, data of acceleration movement of the tissue in the region to be calculated on the basis of the data of two-dimensionally mapped velocities.

* * * * *

UNITED STATES PATENT AND TRADEMARK OFFICE
CERTIFICATE OF CORRECTION

PATENT NO. : 5,701,897
DATED : December 30, 1997
INVENTOR(S) : Akihiro SANO

It is certified that error appears in the above-indentified patent and that said Letters Patent is hereby corrected as shown below:

Claim 10, Column 45, lines 46-47, delete "component moving to the base coordinate point and the velocity component moving in".

Claim 12, column 45, line 58, "comprise" should read --comprises--.

Claim 13, column 46, line 2, "comprise" should read --comprises--.

Signed and Sealed this

Eleventh Day of August 1998

Attest:

BRUCE LEHMAN

Attesting Officer

Commissioner of Patents and Trademarks